US012611299B2

(12) United States Patent
Kalfa et al.

(10) Patent No.: US 12,611,299 B2
(45) Date of Patent: Apr. 28, 2026

(54) TRANSCATHETER DILATABLE BIOSTABLE POLYMERIC STENTED VALVED TUBE PROSTHESIS

(71) Applicant: THE TRUSTEES OF COLUMBIA UNIVERSITY IN THE CITY OF NEW YORK, New York, NY (US)

(72) Inventors: David Kalfa, Long Island, NY (US); Jeffrey W. Kysar, New York, NY (US); Jonathan B. Russ, New York, NY (US); Richard L. Li, Holmdel, NJ (US); Abigail R. Herschman, Brooklyn, NY (US); Haim Waisman, New York, NY (US); Vijay Vedula, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 890 days.

(21) Appl. No.: 17/481,013

(22) Filed: Sep. 21, 2021

(65) Prior Publication Data

US 2022/0000613 A1 Jan. 6, 2022

Related U.S. Application Data

(63) Continuation-in-part of application No. PCT/US2020/024082, filed on Mar. 21, 2020.
(Continued)

(51) Int. Cl.
*A61F 2/24* (2006.01)

(52) U.S. Cl.
CPC .......... *A61F 2/2418* (2013.01); *A61F 2/2433* (2013.01); *A61F 2210/0057* (2013.01);
(Continued)

(58) Field of Classification Search
CPC ........ A61F 2/24; A61F 2/2409; A61F 2/2418; A61F 2/2412; A61F 2/243; A61F 2/2433;
(Continued)

(56) References Cited

U.S. PATENT DOCUMENTS 8,062,355 B2    11/2011   Figulla et al.
8,075,611 B2    12/2011   Millwee et al.
(Continued)

FOREIGN PATENT DOCUMENTS

WO          2009026563 A1      2/2009
WO          WO-2020073056 A1 *   4/2020   ........... A61F 2/2418
WO          WO-2023196150 A1 *  10/2023   ............. A61F 2/243

OTHER PUBLICATIONS

Emani SM, et al. Concept of an expandable cardiac valve for surgical implantation in infants and children. J Thorac Cardiovasc Surg. Dec. 2016;152(6):1514-1523.
(Continued)

*Primary Examiner* — Seema Mathew
(74) *Attorney, Agent, or Firm* — BakerHostetler

(57) ABSTRACT

A transcatheter dilatable valve tube prosthesis is provided including a tubular member capable of plastic deformation from a first dimension to a second dimension; a valve component having a plurality of leaflets. The valve component is capable of expansion from the first dimension to the second dimension, and the valve component is secured to an interior portion of the tubular member by an elastomeric glue at two circumferential portions defining an annular cavity therein. An expandable stent is positioned in the annular cavity between the valve component and the tubular member.

29 Claims, 59 Drawing Sheets

Related U.S. Application Data

(60) Provisional application No. 63/121,155, filed on Dec. 3, 2020, provisional application No. 62/928,400, filed on Oct. 31, 2019, provisional application No. 62/821,676, filed on Mar. 21, 2019.

(52) U.S. Cl.
CPC ... *A61F 2240/004* (2013.01); *A61F 2250/001* (2013.01); *A61F 2250/0082* (2013.01)

(58) Field of Classification Search
CPC ...... A61F 2220/0025; A61F 2210/0076; A61F 2220/005; A61F 2220/0075; A61F 2002/30448
See application file for complete search history.

(56) References Cited

U.S. PATENT DOCUMENTS

| | | | | |
|---|---|---|---|---|
| 8,454,686 | B2 | 6/2013 | Alkhatib | |
| 8,808,237 | B2 | 8/2014 | Thielen et al. | |
| 9,011,524 | B2 | 4/2015 | Eberhardt | |
| 9,675,483 | B2 | 6/2017 | Pacetti et al. | |
| 11,744,702 | B1 * | 9/2023 | Shahriari | A61F 2/2418 |
| | | | | 623/2.17 |
| 12,004,948 | B2 * | 6/2024 | Hofferberth | A61F 2/2433 |
| 2008/0114452 | A1 * | 5/2008 | Gabbay | A61F 2/2412 |
| | | | | 623/2.17 |
| 2009/0036970 | A1 * | 2/2009 | Ma | A61F 2/91 |
| | | | | 623/1.35 |
| 2011/0265329 | A1 | 11/2011 | Mathison | |
| 2013/0253642 | A1 | 9/2013 | Brecker | |
| 2014/0094905 | A1 | 4/2014 | Bonhoeffer et al. | |
| 2014/0277368 | A1 * | 9/2014 | Castaneda | A61F 2/07 |
| | | | | 623/1.13 |
| 2015/0142100 | A1 * | 5/2015 | Morriss | A61F 2/2409 |
| | | | | 623/2.4 |
| 2016/0038283 | A1 | 2/2016 | Divekar et al. | |
| 2016/0175096 | A1 | 6/2016 | Dienno et al. | |
| 2016/0220367 | A1 | 8/2016 | Barrett | |
| 2017/0014228 | A1 | 1/2017 | Emani et al. | |
| 2017/0165057 | A9 | 6/2017 | Morriss et al. | |
| 2017/0189175 | A1 | 7/2017 | Justino et al. | |
| 2017/0333184 | A1 * | 11/2017 | Ryan | A61F 2/2433 |
| 2019/0110893 | A1 * | 4/2019 | Haarer | A61F 2/246 |
| 2019/0209304 | A1 * | 7/2019 | Lee | A61F 2/2475 |
| 2020/0289716 | A1 * | 9/2020 | Heffels | A61L 27/222 |
| 2020/0405480 | A1 * | 12/2020 | Rowe | A61F 2/2418 |
| 2022/0226112 | A1 * | 7/2022 | Mcveigh | A61F 2/2418 |
| 2022/0273426 | A1 * | 9/2022 | Hagaman | A61F 2/2412 |
| 2023/0000620 | A1 * | 1/2023 | Ryan | A61F 2/2436 |
| 2024/0108466 | A1 * | 4/2024 | Francis | A61F 2/2418 |
| 2024/0225675 | A9 * | 7/2024 | Spence | A61B 17/221 |
| 2025/0134657 | A1 * | 5/2025 | Garete | A61F 2/2418 |

OTHER PUBLICATIONS

Chiam PT, et al. Percutaneous transcatheter aortic valve implantation: Evolution of the technology. Am Heart J. Feb. 2009;157(2):229-42.

Bezuidenhout D, et al. Polymeric heart valves for surgical implantation, catheter-based technologies and heart assist devices. Biomaterials. Jan. 2015;36:6-25.

Schulz E, et al. Transcatheter aortic valve implantation with the new-generation Evolut R™: Comparison with CoreValve® in a single center cohort. Int J Cardiol Heart Vasc. Jul. 5, 2016;12:52-56.

Vahl TP, et al. Experimental Evaluation of a Novel Percutaneous Transseptal Catheter-Based Mitral Valve Replacement Technology. Circ Cardiovasc Interv. Sep. 2019;12(9).

Sorajja P, et al. Novel Transcatheter Mitral Valve Prosthesis for Patients With Severe Mitral Annular Calcification. J Am Coll Cardiol. Sep. 17, 2019;74(11):1431-1440.

Rodriguez-Gabella T, et al. Aortic Bioprosthetic Valve Durability: Incidence, Mechanisms, Predictors, and Management of Surgical and Transcatheter Valve Degeneration. J Am Coll Cardiol. Aug. 22, 2017;70(8):1013-1028.

Savoj J, et al. Transcatheter Double Valve-in-Valve Replacement of Aortic and Mitral Bioprosthetic Valves. Cardiol Res. Jun. 2019;10(3):193-198.

El Sabbagh A, et al. Novel Antegrade Approach to Transcatheter Aortic Valve Paravalvular Leak Closure. J Invasive Cardiol. Oct. 2019;31(10):E306-E307.

International Search Report and Written Opinion for PCT counterpart application serial No. PCT/US20/24082, dated Jun. 11, 2020, 10 pages.

* cited by examiner

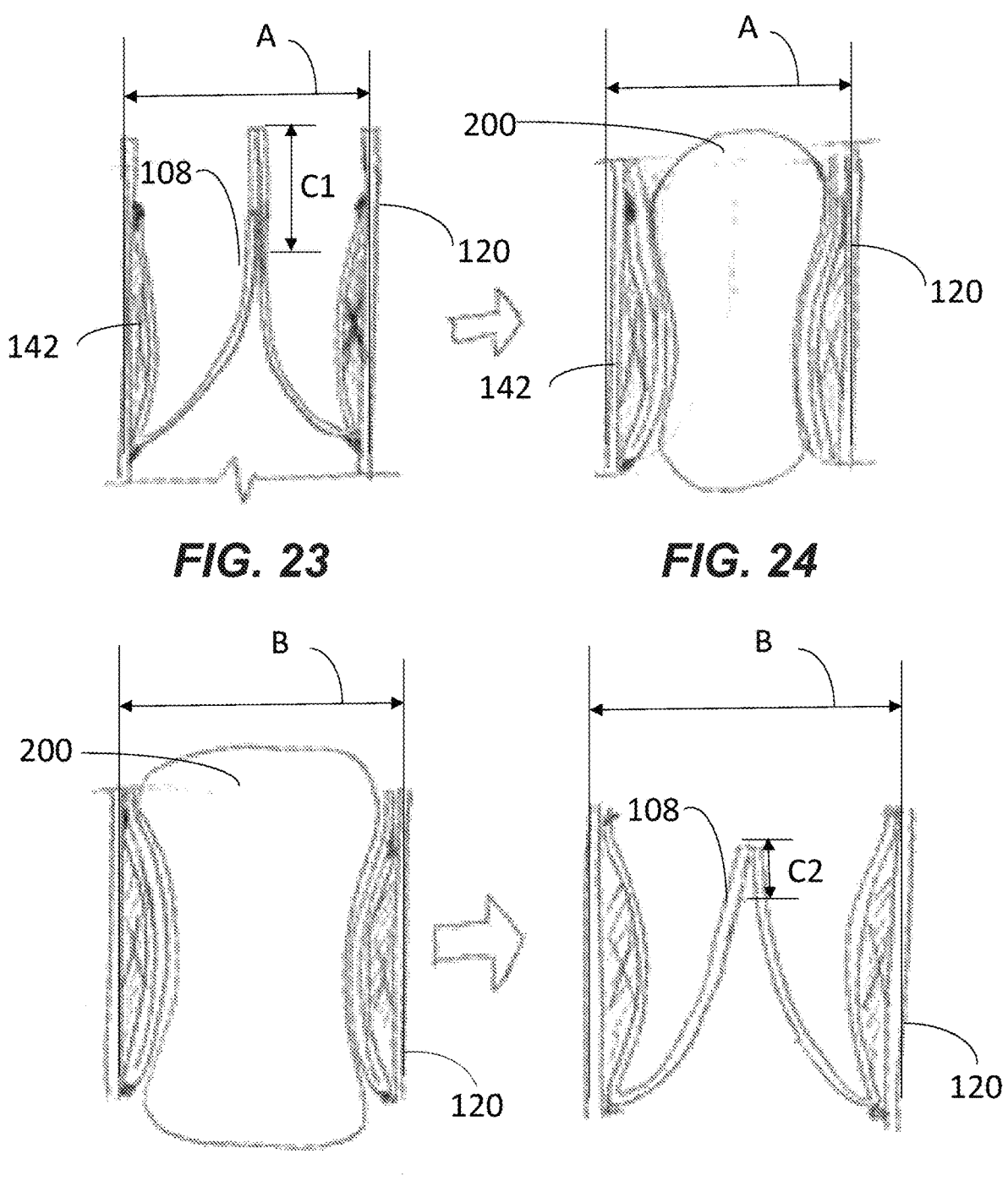
FIG. 23            FIG. 24
FIG. 25            FIG. 26

520

12.3 mm

1 Circ.
Pattern 20 mm

T

W

W

520

(a) *GF* surrogates for 316L stent

(b) *GF surrogates for L605 stent*

(a) *DF* surrogates for 316L stent

(b) *DF surrogates for L605 stent*

(a) *RF surrogates for 316L stent*

(b) *RF surrogates for L605 stent*

(a) $D_{stddev}$ surrogates for 316L stent

(b) *$D_{stddev}$ surrogates for L605 stent*

(a) *DF* vs. *GF* for 316L stent

(b) *DF* vs. *GF* for L605 stent

(a) *RF* vs. *GF* for 316L stent

(b) *RF vs. GF for L605 stent*

(a) *RF vs. DF for 316L stent*

(b) *RF* vs. *DF* for L605 stent (a) $D_{stddev}$ vs. $DF$ for 316L stent

(b) $D_{stddev}$ vs. $DF$ for L605 stent (a) $D_{stddev}$ vs. $GF$ for 316L stent

(b) $D_{stddev}$ vs. $GF$ for L605 stent (a) $D_{stddev}$ vs. $RF$ for 316L stent

(b) $D_{stddev}$ vs. $RF$ for L605 stent

(a) 6 *NCP* and 316L stent

(b) 6 *NCP* and L605 stent

(c) 7 *NCP* and 316L stent

(d) 7 *NCP* and L605 stent

(e) 8 *NCP* and 316L stent

(f) 8 *NCP* and L605 stent

(g) 9 *NCP* and 316L stent

(h) 9 *NCP* and L605 stent

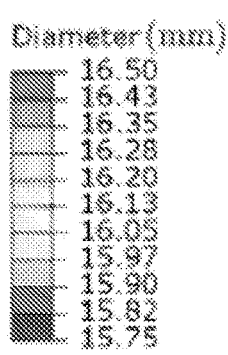
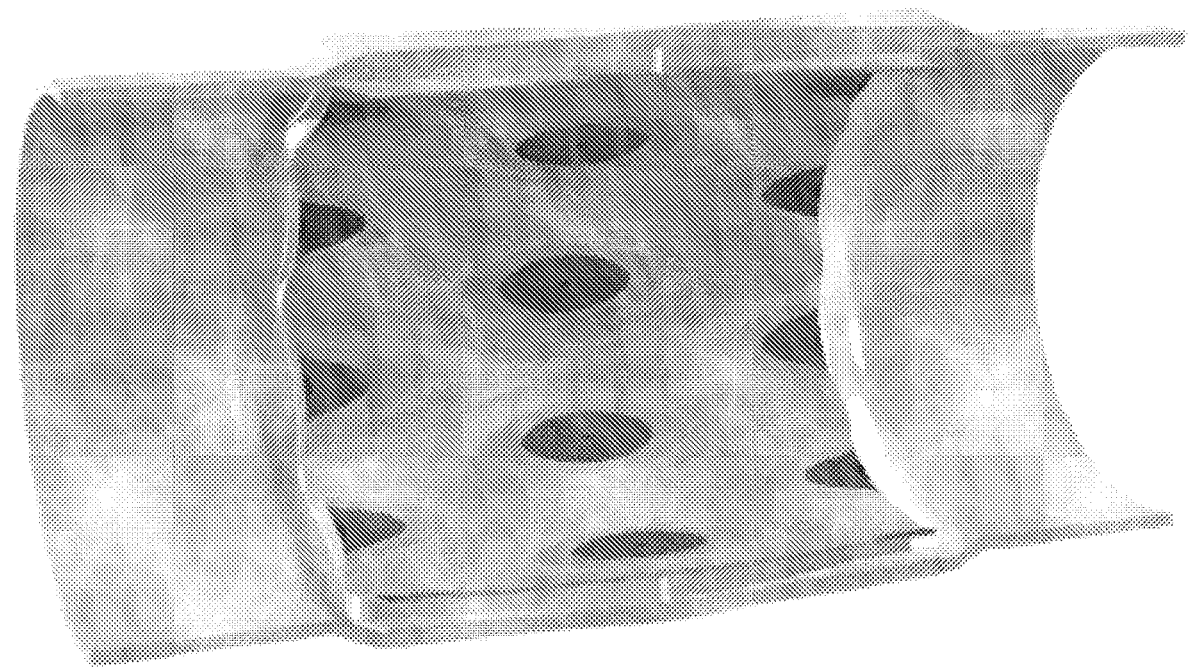
(a) Expanded diameter for 316L stent
*FIG. 53A*

(b) Expanded diameter for L605 stent (a) *DF for 316L stent*

(b) *DF for L605 stent*

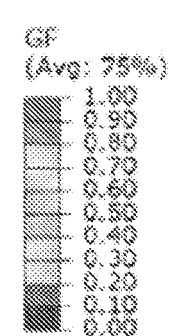
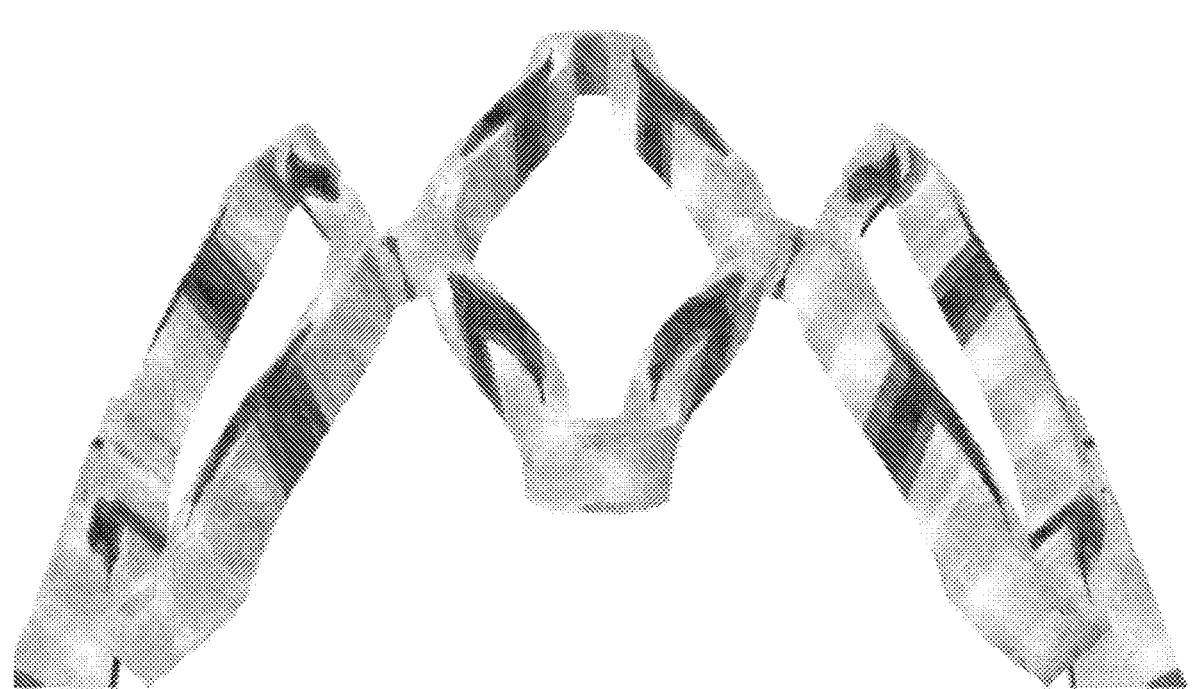
(a) *GF for 316L stent*
*FIG. 55A*

(b) *GF* for L605 stent

TRANSCATHETER DILATABLE BIOSTABLE POLYMERIC STENTED VALVED TUBE PROSTHESIS

CROSS-REFERENCE TO RELATED APPLICATIONS

This application is a continuation-in-part of PCT/US2020/024082 filed Mar. 21, 2020, which claims the benefit of priority to U.S. Provisional Application Nos. 62/821,676 filed Mar. 21, 2019 and 62/928,400 filed Oct. 31, 2019. This application also claims the benefit of priority to U.S. Provisional Application No. 63/121,155 filed Dec. 3, 2020. All of the aforementioned applications are incorporated by reference in their entirety herein.

FIELD

The disclosed subject matter describes a transcatheter dilatable biostable polymeric stented valved tube prosthesis.

BACKGROUND

Congenital heart disease (CHD) affects an estimated 40,000 children per year in the United States alone, within which an estimated 20% of cases involve abnormalities in the right ventricular outflow tract (RVOT) and may require pulmonary valve replacement.

Children with CHD who need the implantation of a valved conduit between the right ventricle and the pulmonary artery typically require between one and four open-heart reoperations before they reach adulthood. Indeed, all prostheses commercially available to replace the right ventricular outflow tract (RVOT) (including cryopreserved homografts, xenograft conduits, bioprostheses and mechanical prostheses) do not grow with the child and have serious drawbacks, such as thromboembolic complications, calcification-induced limited durability, need for anti-coagulant therapy, inflammation-related pannus formation or intraluminal proliferation of fibrotic tissue. Cryopreserved homografts need a revision surgery in 36-90% of the cases after 10 and 15 years, respectively. As a result, pediatric patients are faced with a lifelong risk of valve-related morbidity and up to 50% reduction in life expectancy.

Bioprosthetic valves implanted during transcatheter procedures are made of biological tissues prone to degeneration and calcification. Moreover, transcatheter valve implantations are not an option in children as these children have hypoplastic or absent vessels that do not allow for the percutaneous implantation of a valve.

Tissue engineering has been investigated as a possible way to create a living autologous valved conduit. Nevertheless, tissue-engineered valves have still major shortcomings such as insufficient structural stability of the leaflets and an uncontrolled balance between polymer biodegradation and extracellular matrix formation, which lead to ultimate failure of these constructs.

The development of polymeric heart valve has made advances over the past years. Their durability is now good enough to bring a child into adulthood without losing the structural integrity of the leaflets. Polymeric non-valved tubes are used extensively in pediatric surgery to reconstruct the right ventricular outflow tract (or other lesions) but these tubes are not valved and they are not designed to be expandable.

Recently, multiple computational models of heart valves incorporating the structural mechanics, fluid dynamics and the nonlinear fluid-structure coupling have been developed in an effort to increase the accuracy of the predicted response. However, there have not been any computational investigations related to in-situ expansion of a replacement valve and the effects the expansion may have on the valve performance.

What is needed is a polymeric valved tube that can be implanted surgically and then expanded to match the growth of the child in order to avoid multiple reoperations to change and upsize the valve.

SUMMARY

A transcatheter dilatable valve tube prosthesis is provided including a tubular member capable of plastic deformation from a first dimension to a second dimension; a valve component having a plurality of leaflets. The valve component is capable of expansion from the first dimension to the second dimension, and the valve component is secured to an interior portion of the tubular member by an elastomeric glue material at two circumferential portions defining an annular cavity therein. An expandable stent is positioned in the annular cavity between the valve component and the tubular member. The cavity can also be filled with elastomeric glue material, such that the stent is embedded within the glue material which fills the inside of the cavity.

In some embodiments, the tubular member is fabricated of expanded polytetrafluoroethylene (ePTFE). In some embodiments, the valve component is fabricated from a sheet of ePTFE.

In some embodiments, the first dimension is a diameter of about 12 mm and the second dimension is a diameter of about 24 mm.

In some embodiments, the plurality of leaflets define a height of coaptation and length of the free edge, wherein the height of coaptation and/or length of the free edge at the first dimension and the second dimension is sufficient to maintain of the integrity of the valve component.

In another aspect, a system for installation of a transcatheter dilatable valve tube prosthesis is provided, including a transcatheter dilatable valve tube prosthesis having a tubular member capable of plastic deformation from a first dimension to a second dimension; a valve component with a plurality of leaflets, the valve component capable of expansion from the first dimension to the second dimension, the valve component secured to an interior portion of the tubular member by an elastomeric glue at two circumferential portions defining an annular cavity therein; and an expandable stent positioned in the annular cavity between the valve component and the tubular member. The system includes a balloon catheter insertable into the transcatheter dilatable valve tube prosthesis to expand the tubular member and the valve component from the first dimension to the second dimension.

In a further aspect, a method of installing a transcatheter dilatable valve tube prosthesis in the body conduit of a patient is provided, including providing a transcatheter dilatable valve tube prosthesis including a tubular member capable of plastic deformation from a dimension to a second dimension; a valve component having a plurality of leaflets, the valve component capable of expansion from the first dimension to the second dimension, the valve component secured to an interior portion of the tubular member by an elastomeric glue at two circumferential portions defining an annular cavity therein; and an expandable stent positioned in the annular cavity between the valve component and the tubular member; inserting the transcatheter dilatable valve tube prosthesis into the body conduit of the patient; securing the transcatheter dilatable valve tube prosthesis; inserting a balloon catheter into the transcatheter dilatable valve tube prosthesis; and expanding the balloon catheter, thereby expanding the tubular member from the first dimension to the second dimension.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 23 illustrates a sectional view of the prosthetic prior to insertion of the balloon at the initial diameter.

FIG. 24 illustrates a sectional view of the prosthetic during insertion of the balloon at the initial diameter.

FIG. 25 illustrates a sectional view of the prosthetic during insertion of the balloon at the expanded diameter.

FIG. 26 illustrates a sectional view of the prosthetic after removal of the balloon at the expanded diameter.

FIG. 53A is an isometric side cross-section of the stented region of 316L stent material illustrating the spatial variation of the permanent diameter in the stented region.

FIG. 55A illustrates the spatial variation of the Goodman Fatigue metric (GF) for 316L stent material.

DETAILED DESCRIPTION

Figure 1:
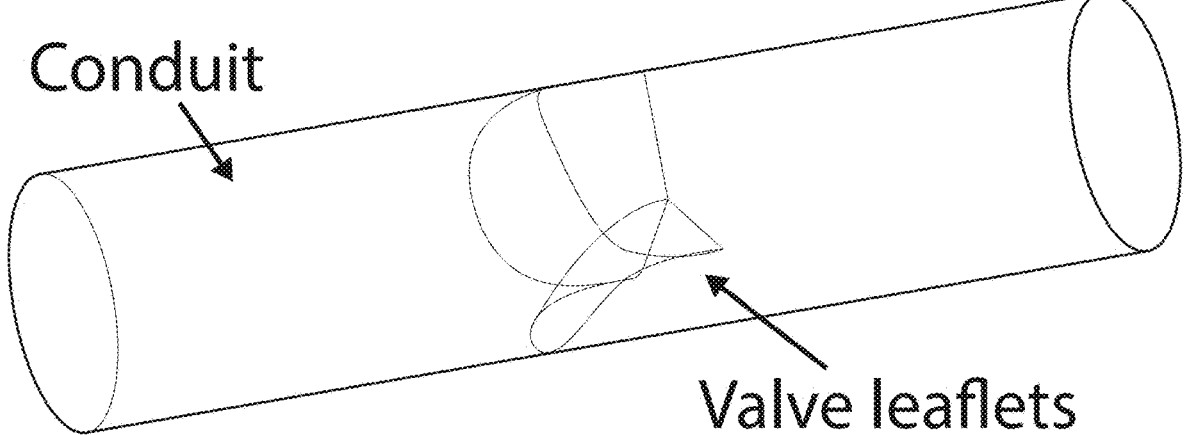
FIG. 1 is a schematic view of the prosthesis in accordance with an exemplary embodiment of the disclosed subject matter.

Reference will now be made in detail to select embodiments of the disclosed subject matter, examples of which are illustrated in the accompanying drawings. The method and corresponding steps of the disclosed subject matter will be described in conjunction with the detailed description of the system.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

As used herein and in the appended claims, the singular forms "a," "an," and "the" include plural referents unless the context clearly dictates otherwise.

In accordance with the various embodiments of the disclosed subject matter, as summarized above and as described in further detail below, there is provided systems, apparatuses and methods of manufacture and use of a transcatheter dilatable biostable polymeric stented valved tube prosthesis.

In some embodiments, the prosthesis is composed of a tubular component and a valved component. The prosthesis can also be a non valved tube only. The prosthesis is typically implanted surgically. In some embodiments, the prosthesis can be implanted percutaneously (transcatheter approach).

The prosthesis is dilated, e.g., enlarged as the patient grows, via a balloon dilation transcatheter approach from an initial diameter A to a second enlarged diameter B. Transcatheter dilation avoids the need for reoperation in children (relative restriction of the conduit related to somatic growth) and in adults (absolute restriction of the conduit related to intimal proliferation). In some embodiments, the diameter of the tube increases from a neonatal size (8 mm) to an adult size (23 mm) through one or more successive dilations. In some embodiments the tube is fabricated with enlarged diameter B and reduced to the diameter A by crimping or material compression before implantation.

Transcatheter dilation is made possible through the use of materials used in the conduit and the construction of the valve. For example, dilatable biomaterials, such as elastomeric thermoplastic polyurethanes or any other elastomeric polymers or other dilatable biomaterials can be used. In some embodiments, the device stays dilated after balloon dilation due to the plasticity of the polymers used. Alternatively, thermo-responsive or light-responsive polymer or any type of external or internal stimuli-responsive biomaterial (Ph, electric field, ultrasound). In such case, the dilation can be driven by heat or light or other stimulus. Thermo-responsive polymers useful for this application include, e.g., NIPAAm, poloxamers, poly(N-alkylacrylanide) such as poly(N-isopropylacrylamide) (PNIPAAm) (LC ST 32-37c), poly(N,N-diethylacrylamide) (PDEAAm), poly(Nvinly-caprolactam) (PVCL), poly(N-vinylcaprolactam).

The biomaterials used are biostable, and typically are not intended to be biodegradable or bioresorbable.

The construction of the valve provides for valve competence at enlarged diameters. In some embodiments, the valve is made of an extensible biomaterial, such as polyurethane or expanded polytetrafluroethylene (ePTFE), which allows the circumference of the valve to follow the increase in circumference of the tube after dilation.

In some embodiments, the design of the valved component includes an increased height of coaptation and length of the leaflet free edge which allows the valve to remain competent despite the increase of the tube diameter: the valve flattens at the time of the successive balloon dilation of heat/light-driven dilations.

In some embodiments, the device is fabricated in one or two steps, using one or more of the fabrication processes: injection molding, extrusion, dip molding, dip coating, 3D printing, electrospinning, film fabrication or any other type of fabrication process.

In some embodiments, the cohesion of the valved and tube components is achieved through, e.g., (1) a one-step monobloc fabrication process; (2) an added step involving the use of a dilatable circular continuous or discontinuous stabilization structure such as a stent, a prefractured wire-frame or annulus or any other type of stabilizing structure; (3) mechanical bonding through the use of a polymeric glue.

Example A

A plastically deforming polymeric cardiac valved conduit is provided that permanently expands to accommodate a child's growth using transcatheter balloon dilation. It is intended for the pulmonary position, but it could also be implanted in the aorta.

As illustrated in FIG. 1, the polymeric valved conduit consists of a tri-leaflet valve inside a 10 cm long conduit. It can be manufactured with various diameters from 10 mm to 22 mm, and the length can be provided to the length of conduit needed.

The conduit can be permanently expanded to a second diameter, e.g., 24 mm, using a balloon catheter. The valve leaflets may expand along with the conduit to maintain valve competency after the expansion. A portion of the leaflets may also be designed to maintain valve competency without needing to expand along with the conduit, using methods such as an increased height of coaptation, increased length of the free edge, or other geometrical designs.

The conduit material is capable of plastic (e.g., permanent) deformation, yet maintain its integrity. Exemplary biostable, elastomeric polyurethane materials for the include Carbothane AC-4075A (Lubrizol, Cleveland, Ohio) and Elast-Eon E5-325 (AorTech, Weybridge, Surrey).

Uniaxial tensile testing (Instron MicroTester 5848, Norwood, Massachusetts) was performed, and such materials exhibited a non-linear hyperelastic stress-strain response, as well as viscoelastic creep and stress relaxation behaviors. Uniaxial stretch tests (FIGS. 2-3) were performed to evaluate their ability to plastically stretch and determine their suitability as the expanding conduit material. The amount of immediate recovery was illustrated in solid line, and permanent deformation was illustrated in dotted line after 5.1× stretching.

Figure 2:
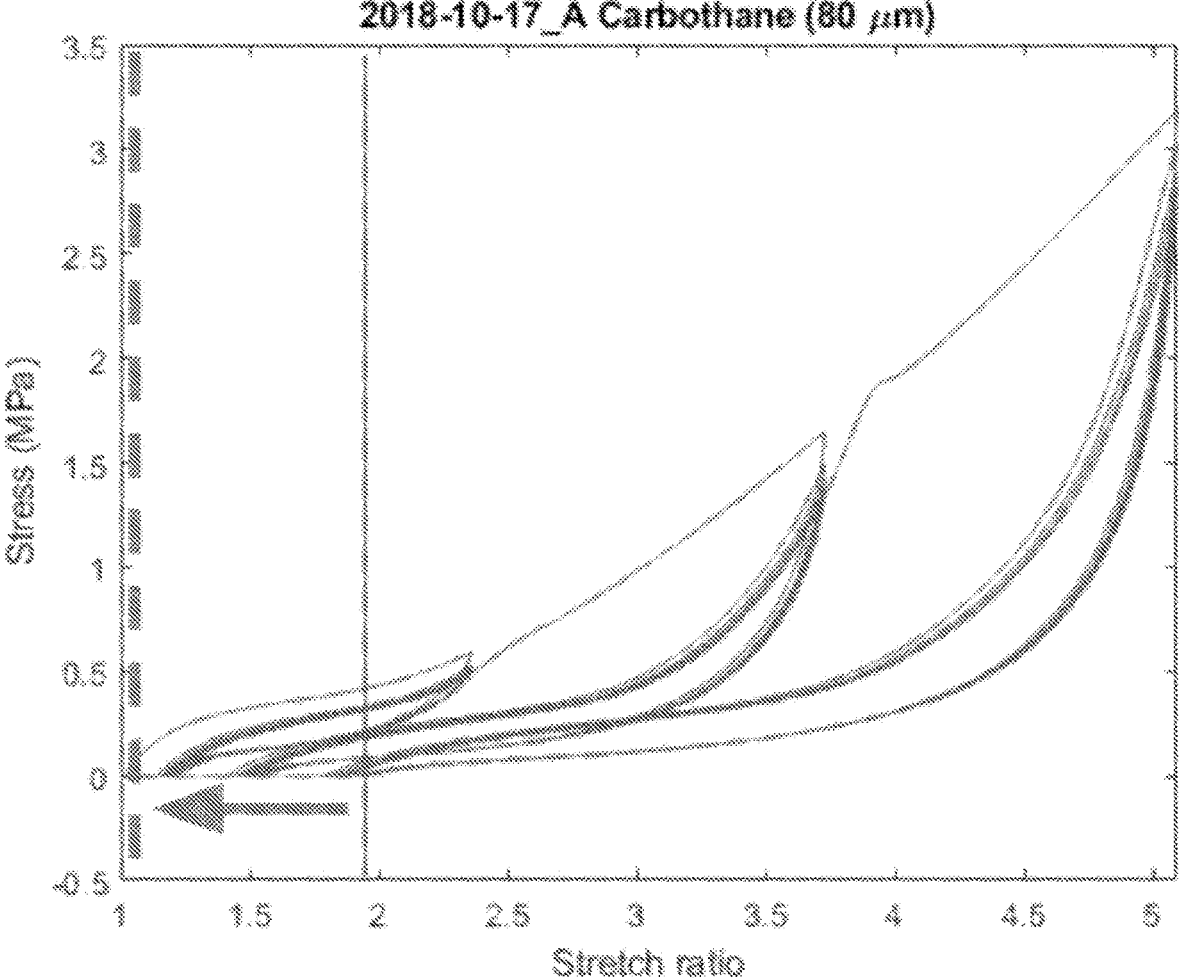
FIG. 2 illustrates uniaxial stretch tests for Carbothane indicating the amount of immediate recovery and permanent deformation after 5.1× stretching.
Figure 3:
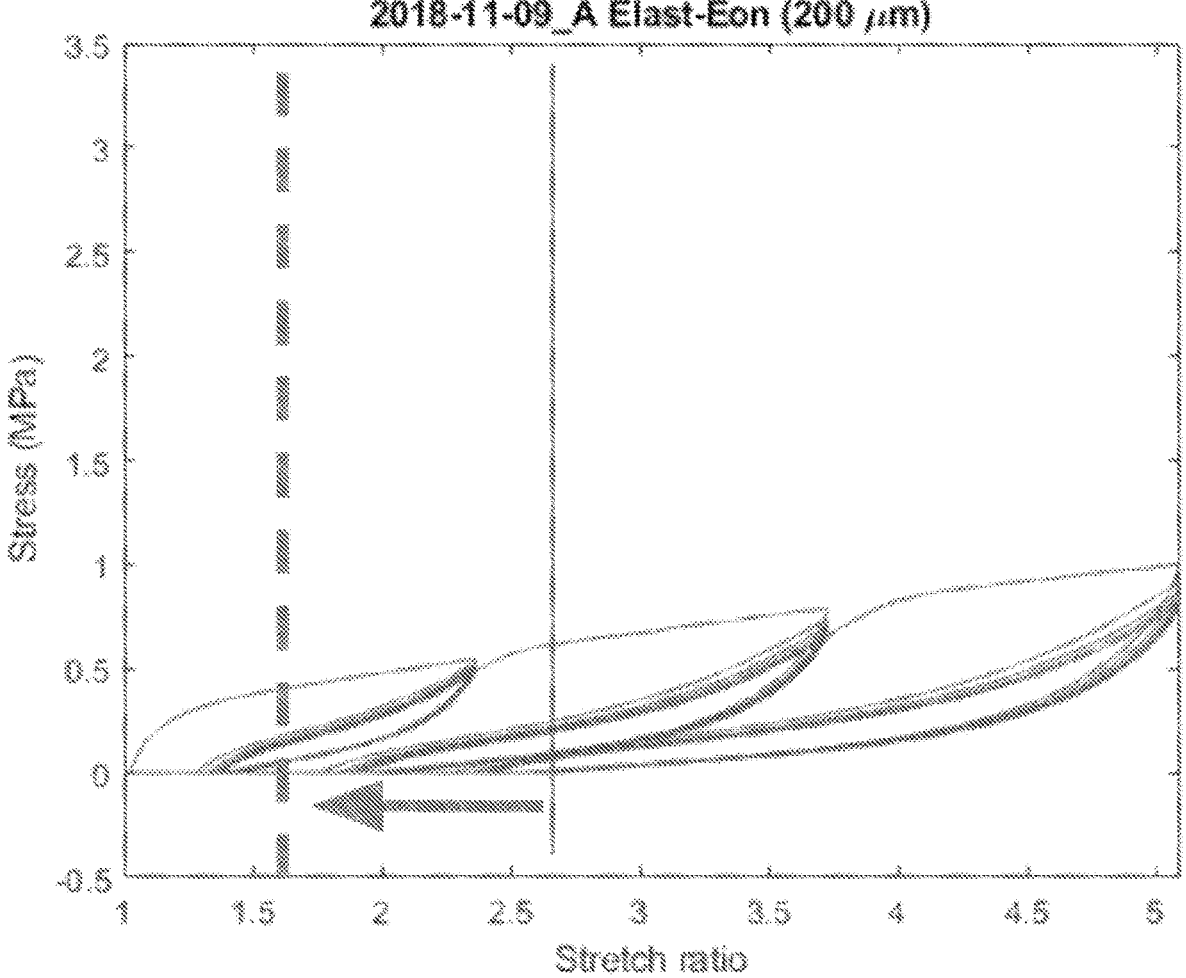
FIG. 3 illustrates uniaxial stretch tests for Elast-Eon indicating the amount of immediate recovery and permanent deformation after 5.1× stretching.
Figure 29:
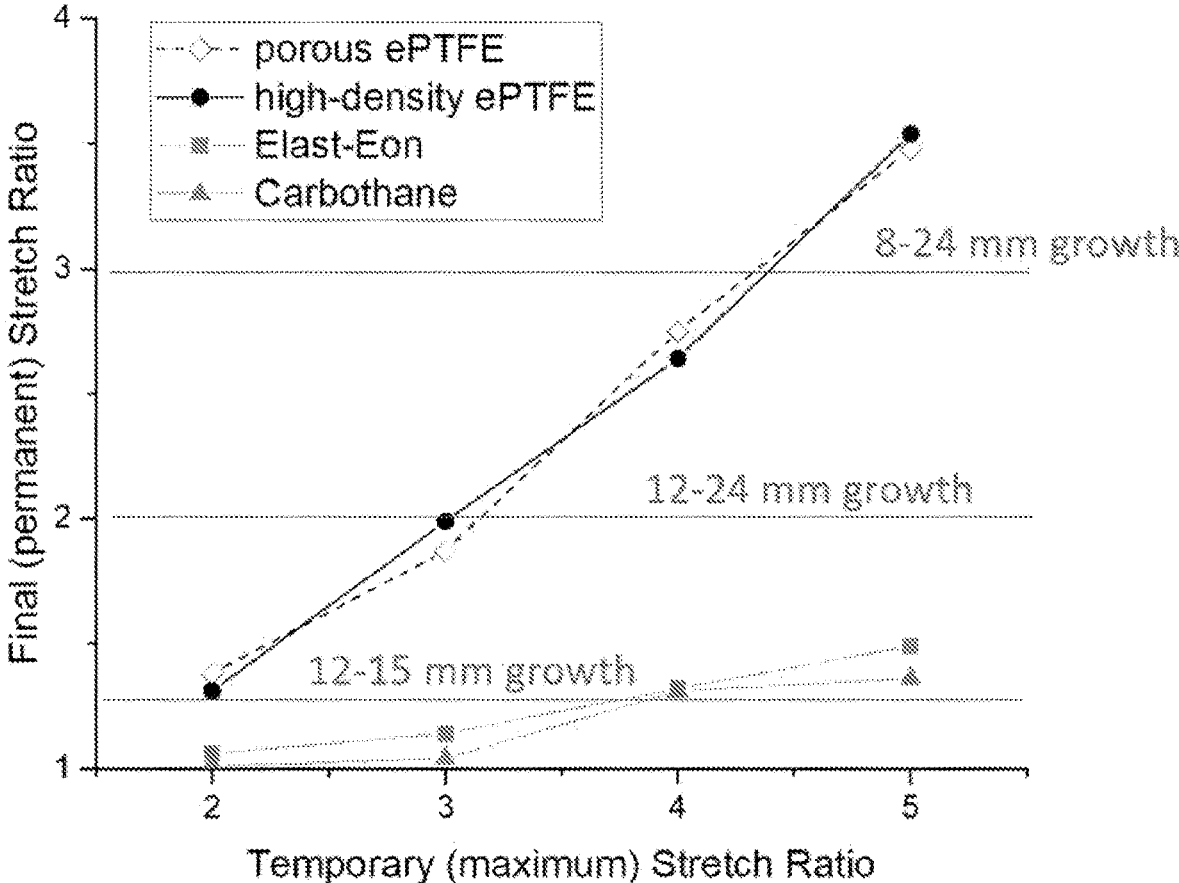
FIG. 29 illustrates the amount of permanent deformation resulting from progressively larger temporary stretches for exemplary materials.

As illustrated in FIG. 2, it was observed that stretching Carbothane by a stretch ratio of $\lambda=5.1$ resulted in an immediate recovery to $\lambda=2.0$. After dissipation of viscoelastic effects (~24 hours), the stretch was nearly fully recovered, and the permanent deformation was negligible ($\lambda\sim1$). However, as illustrated in FIG. 3, stretching Elast-Eon by a temporary stretch ratio of $\lambda=5.1$ resulted in an immediate recovery to $\lambda=2.7$ and, after dissipation of viscoelastic effects, a permanent stretch of $\lambda=1.6$. These results indicate that Carbothane is better suited as the valve leaflet material, while Elast-Eon is better suited for the conduit. FIG. 29 illustrates the amount of permanent deformation resulting from progressively larger temporary stretches for Carbothane, Elast-Eon, and two types of ePTFE.

Figure 4:
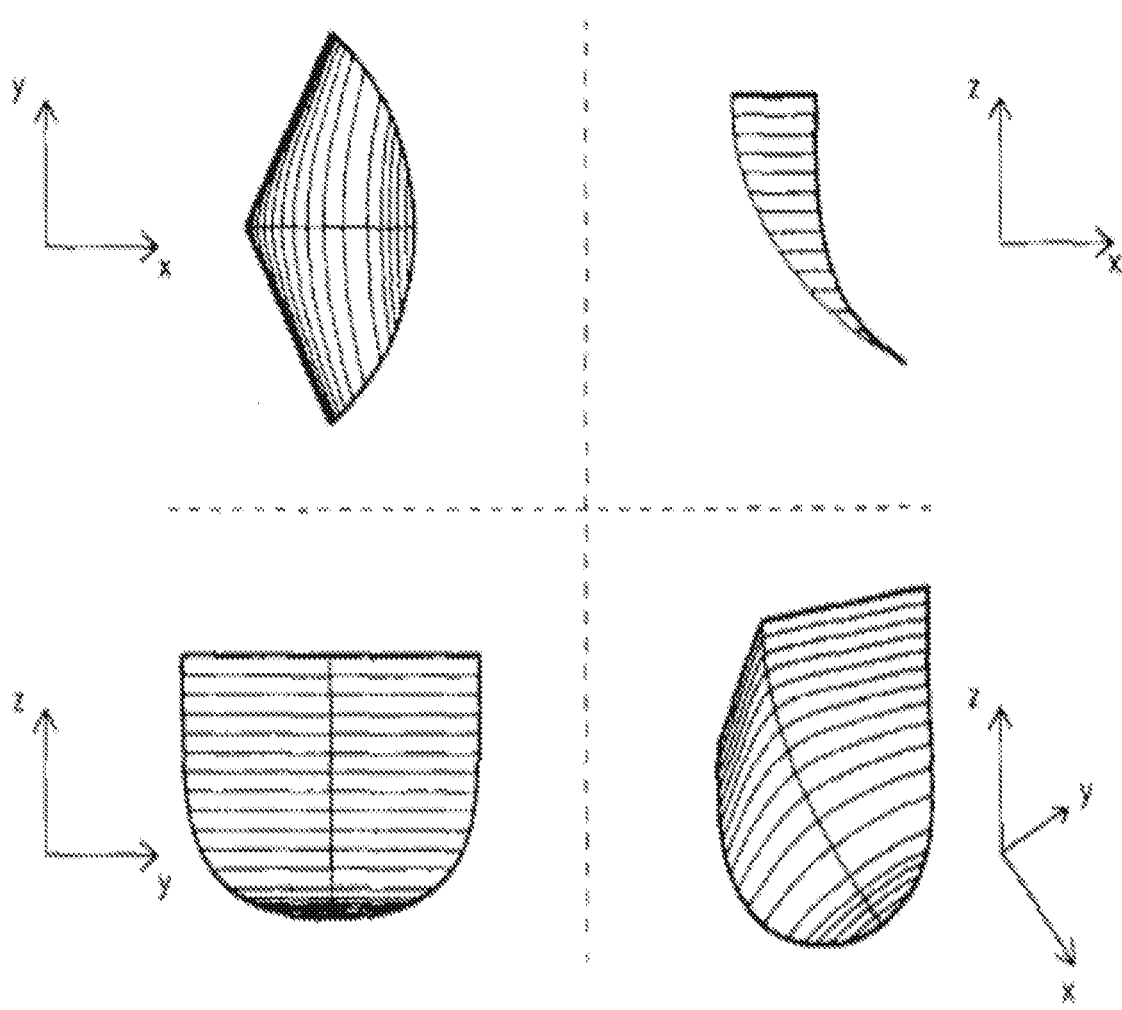
FIG. 4 illustrates an Ellipto-hyperbolic leaflet design.
Figure 5:
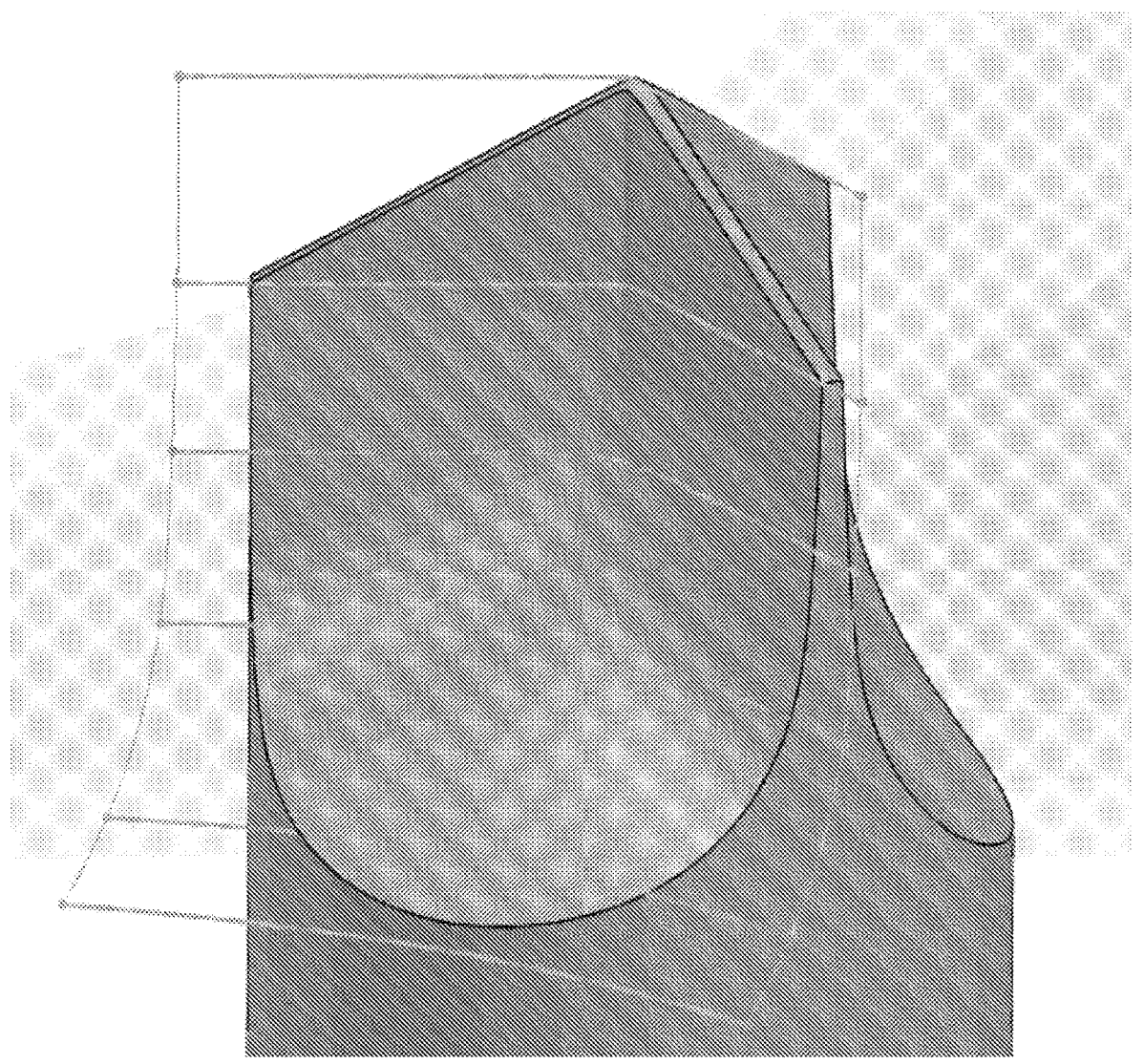
FIG. 5 illustrates the valve design with increased coaptation length in accordance with an exemplary embodiment of the disclosed subject matter.
Figure 27:
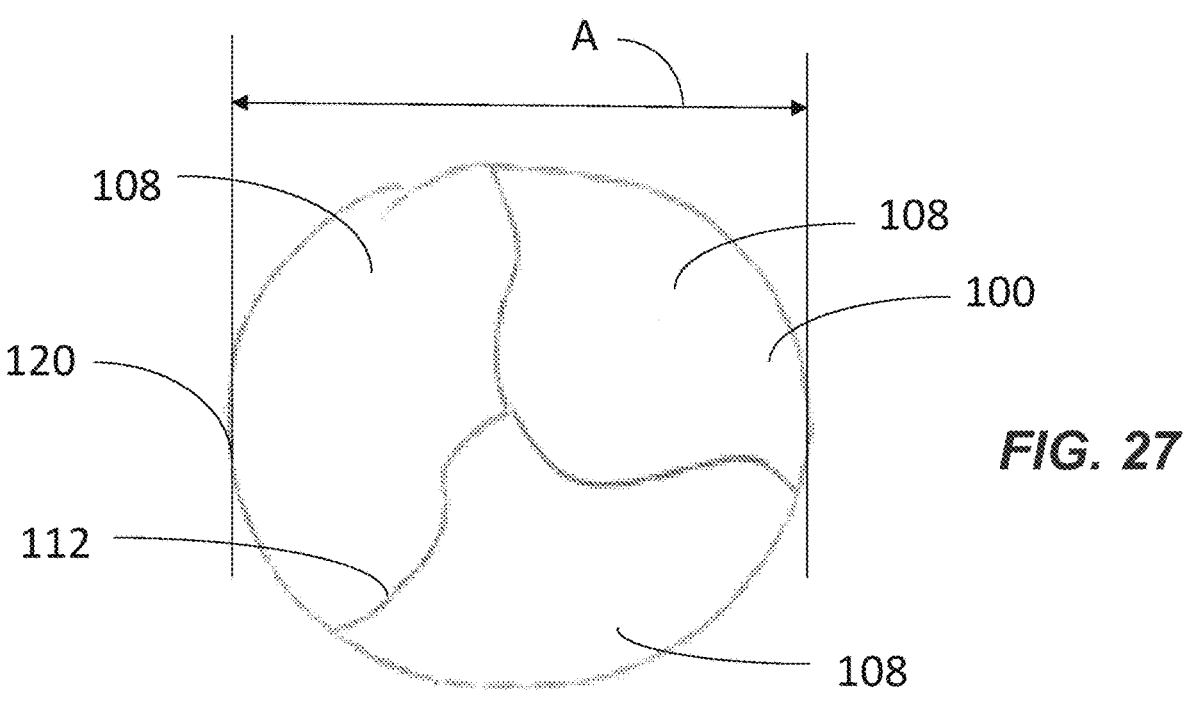
FIG. 27 illustrates and end view of the prosthetic prior to insertion of the balloon at the initial diameter.
Figure 28:
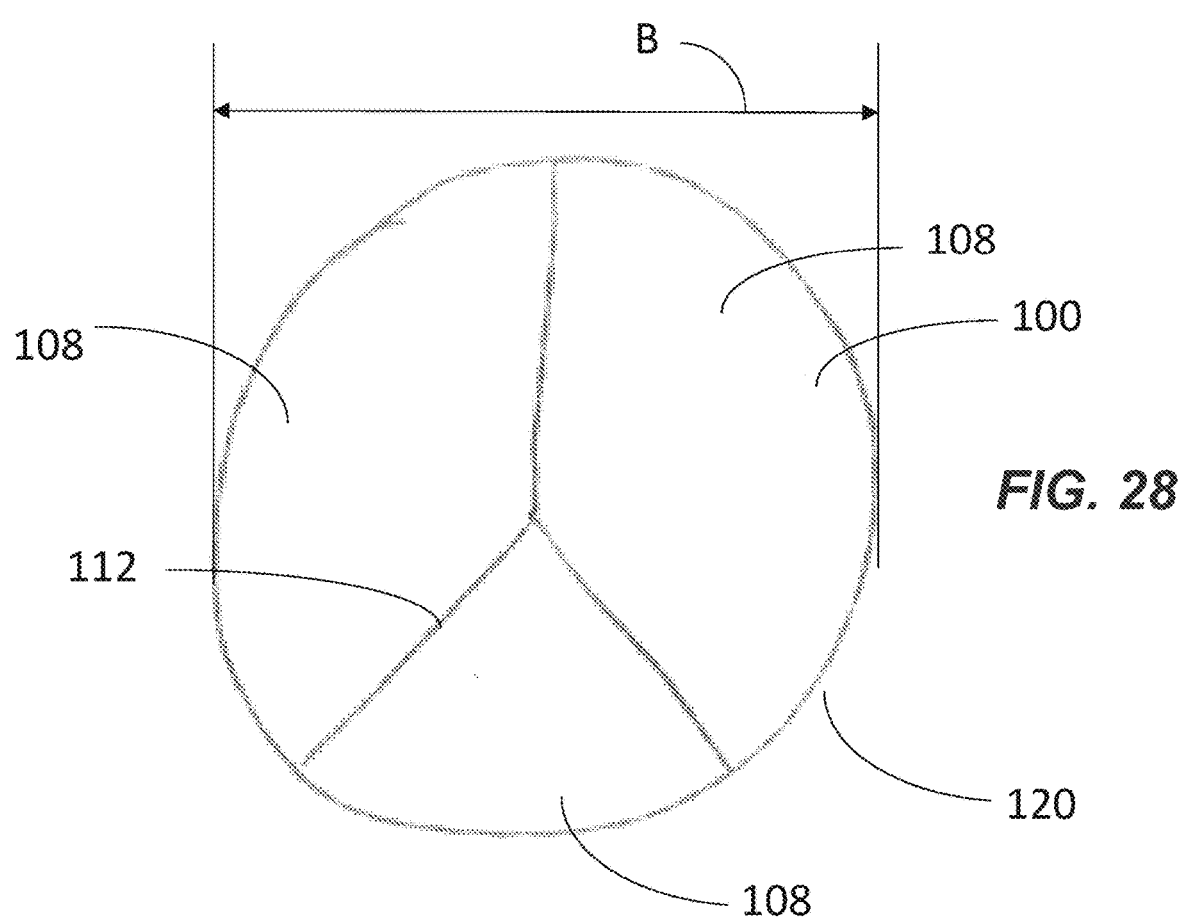
FIG. 28 illustrates an end view of the prosthetic after removal of the balloon at the expanded diameter.

As illustrated in FIG. 4, leaflets having ellipto-hyperbolic geometry in a polymer valve have been able to achieve 800 million cycles during in vitro fatigue testing. To ensure adequate coaptation after the valve dilation, however, our novel design increases the coaptation length in the radial direction (FIG. 5) and the length of the leaflet free edge (FIGS. 27-28).

Figure 6:
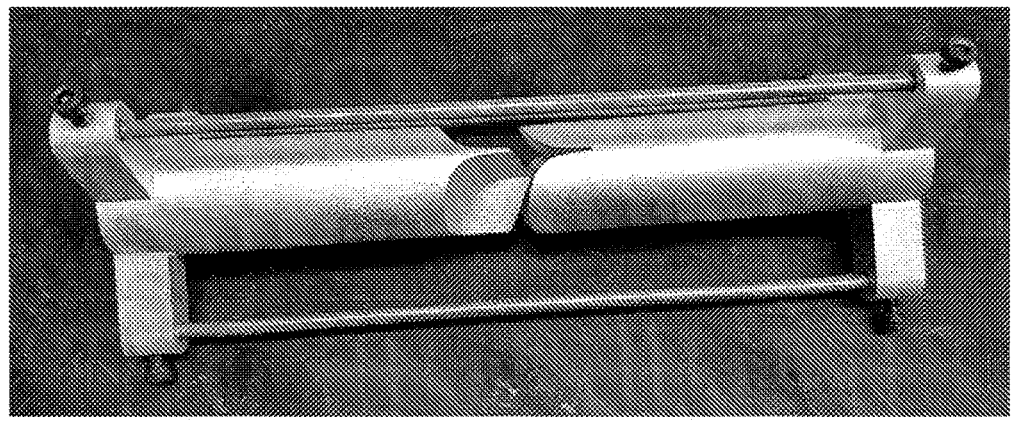
FIG. 6 illustrates a mold for fabrication of the prosthesis in accordance with an exemplary embodiment of the disclosed subject matter.
Figure 7:
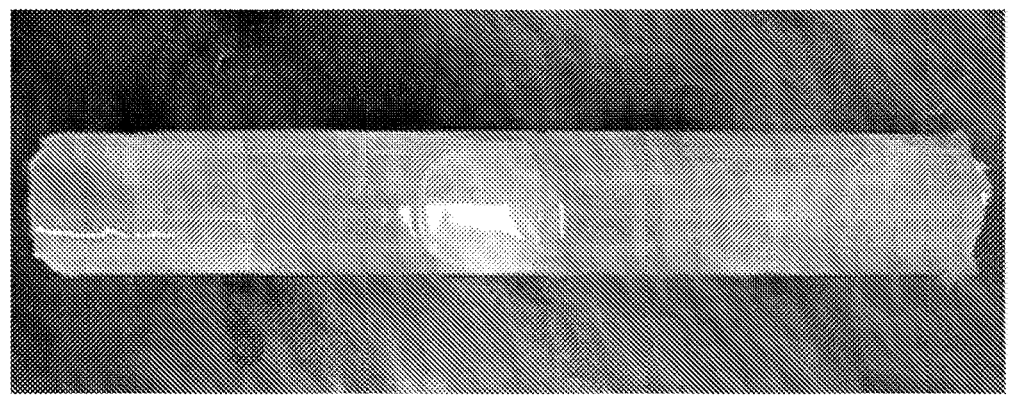
FIG. 7 illustrates a perspective side view of the prosthesis in accordance with an exemplary embodiment of the disclosed subject matter.
Figure 8:
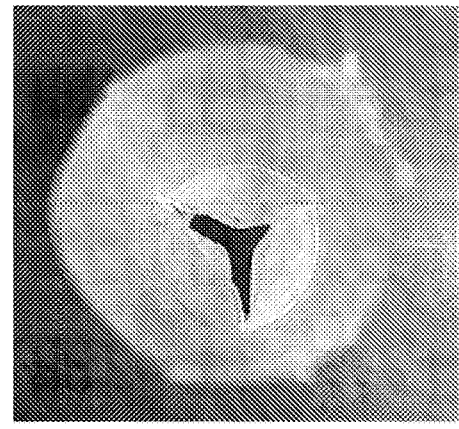
FIG. 8 illustrates an end view of the prosthesis in accordance with an exemplary embodiment of the disclosed subject matter.

Various fabrication processes for the fabrication of polymer heart valves include film fabrication, compression molding, injection molding, cavity molding, and dip molding. In some embodiments, dip molding is used since this technique yields the most promising results, with many previous dip-molded devices reaching several hundreds of millions of cycles during in vitro fatigue testing. In one embodiment, a mold for a 12 cm long conduit containing a tri-leaflet valve, with extra coaptation length to preserve valve competency after the conduit dilation was used (FIG. 6). Prostheses were fabricated from Elast-Eon by dipping this mold into a liquid solution of Elast-Eon (30% w/v) dissolved in an organic solvent (N,NDimethylacetamide, 99.5%, ACROS Organics), then evaporating the solvent at 80° C. to leave a conformal film of Elast-Eon. The leaflets were separated using a sharp blade. (FIGS. 7-8)

In Vitro Testing

Figure 9:
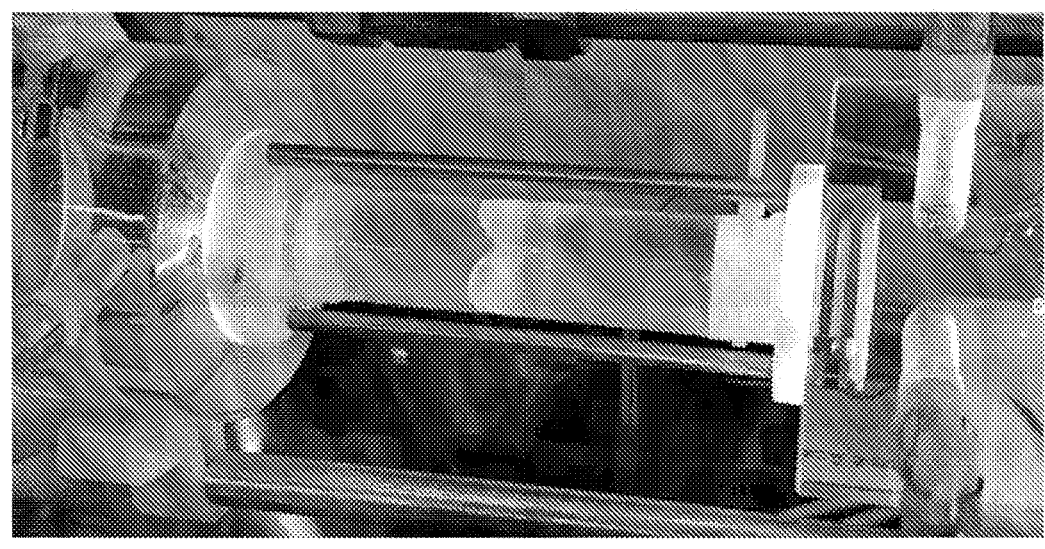
FIG. 9 illustrates the prosthesis of FIGS. 1, 7 and 8 in a testing rig, prior to balloon dilation.
Figure 10:
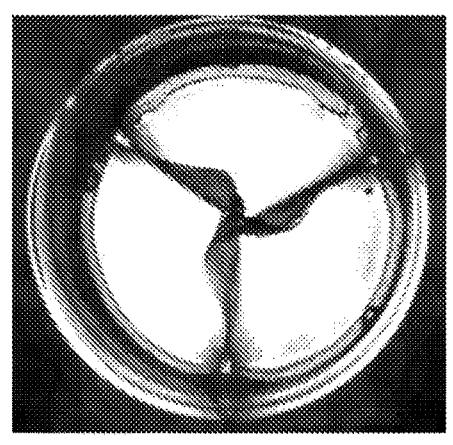
FIG. 10 illustrates an end view of the prosthesis with the valve in the closed position in the first, initial diameter prior to balloon dilation.
Figure 11:
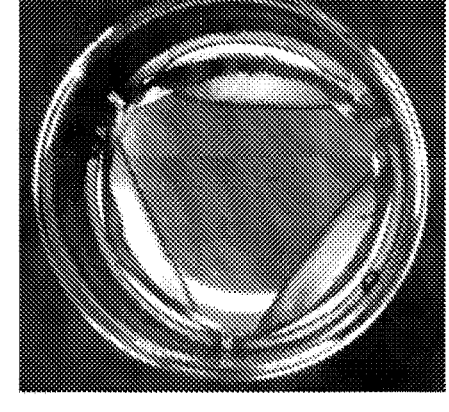
FIG. 11 illustrates an end view of the prosthesis with the valve in the open position in the first, initial diameter prior to balloon dilation.

In vitro testing was performed, both prior to and after balloon dilation, using a pulse duplicator (BDC Laboratories, Wheat Ridge, Colorado) (FIG. 9) at a heart rate of 70 bpm, pulmonary pressure of 88/67 mmHg, and mean arterial pressure of 77 mmHg. Prior to dilation, the 22 mm diameter device showed basic valve competency, with a regurgitant fraction of 2.0%, closing volume fraction of 0.8%, leakage volume fraction of 1.2%, effective orifice area of 1.50 cm², and a mean pressure differential of 12.7 mm Hg at a simulated cardiac output of 2.68 L/min. (FIGS. 10-11).

Figure 12:
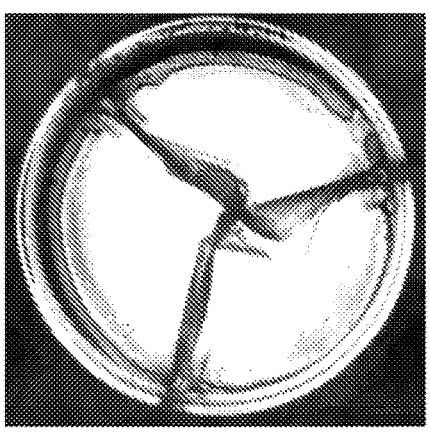
FIG. 12 illustrates an end view of the prosthesis with the valve in the closed position in the second, expanded diameter after balloon dilation.
Figure 13:
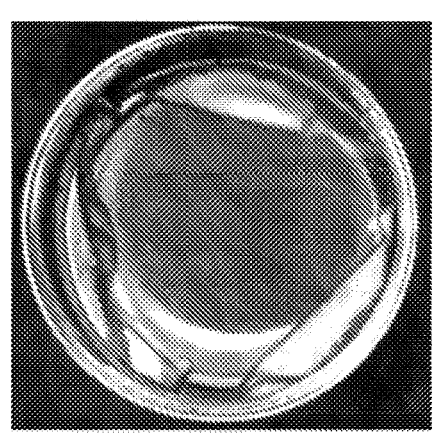
FIG. 13 illustrates an end view of the prosthesis with the valve in the open position in the second, expanded diameter after balloon dilation.
Figure 14:
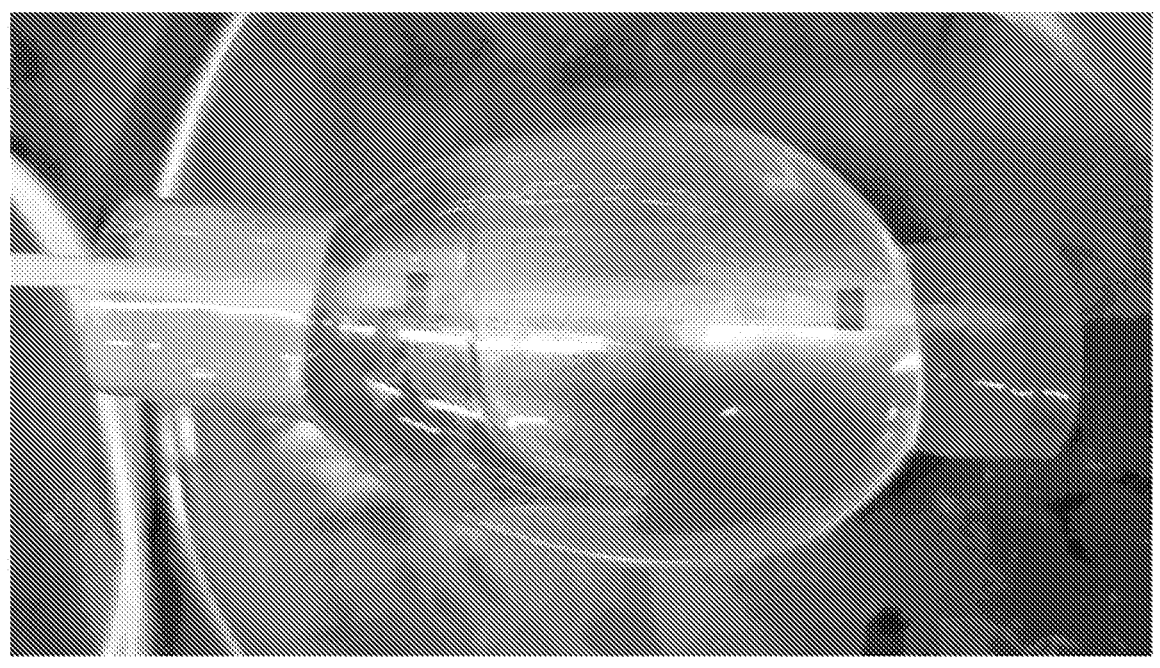
FIG. 14 illustrates the prosthesis during balloon dilation using a balloon catheter
Figure 15:
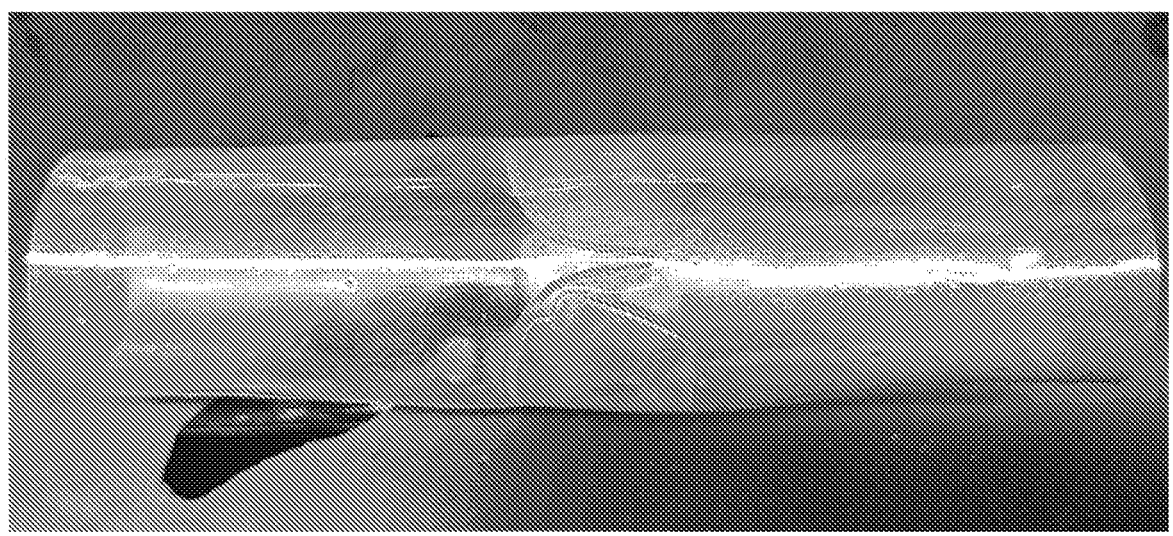
FIG. 15 illustrates the dilated configuration of prosthesis of FIGS. 12-13.

Dilation of the 22 mm diameter valved conduit was performed using a 46 mm diameter Coda balloon catheter (FIG. 13). After inflation to a maximum diameter of ~47 mm, the balloon was immediately deflated to allow the conduit to recover. The conduit immediately recovered to a diameter of 27.7 mm, and after 24 hours it had a permanent diameter of 24.8 mm. (FIGS. 12-13, and 15). In vitro testing of the dilated device showed that valve competency was preserved, with a regurgitant fraction of 8.5%, closing volume fraction of 3.2%, leakage volume fraction of 5.3%, effective orifice area of 1.67 cm², and a mean pressure differential of 12.0 mm Hg at a simulated cardiac output of 2.93 L/min.

Computational Modelling

Figure 16:
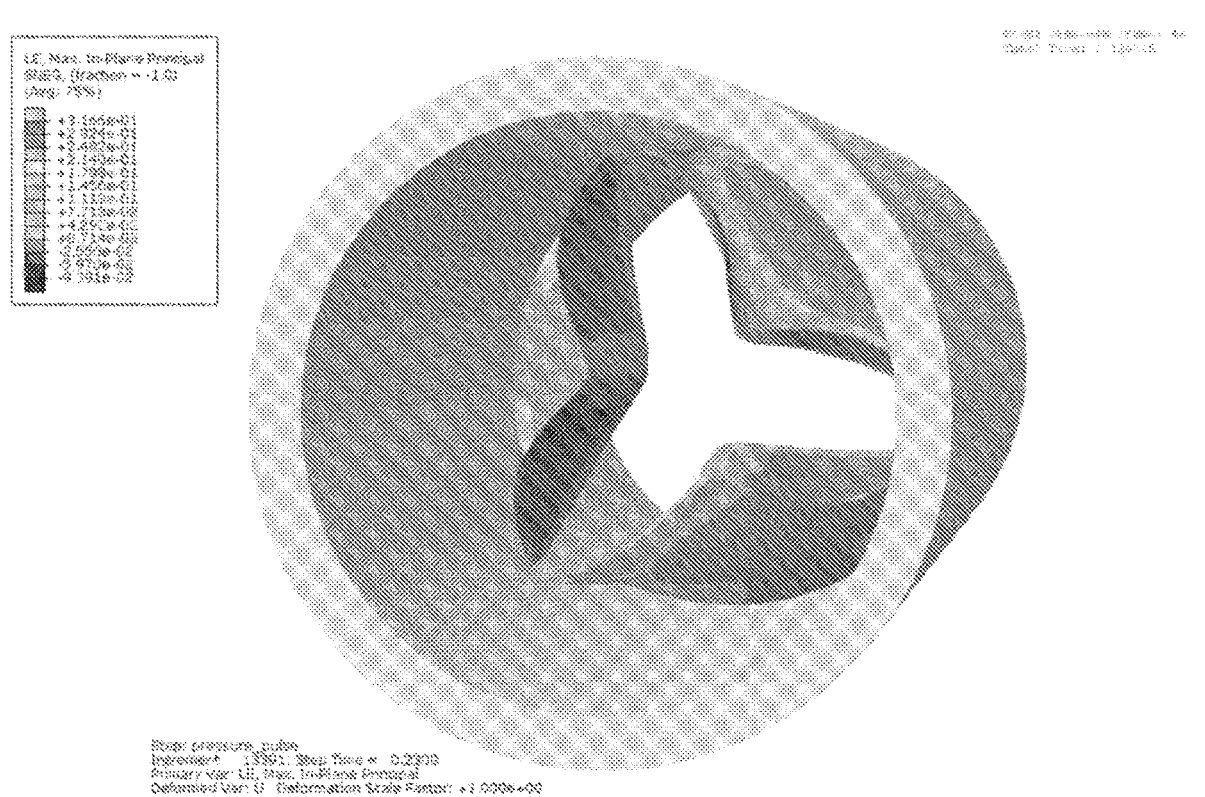
FIG. 16 illustrates a finite element model of prosthesis during a simulated pulse cycle.

The valve design is optimized for performance both before and after the balloon dilation. To help perform the optimization, a computational finite element model of the device is being developed. (FIG. 16). The leaflet and conduit geometries were recreated from the dip mold design. Experimental results from tensile testing were used to determine approximate material parameters for a Mooney-Rivlin hyperelastic model of Elast-Eon. The upstream and downstream fluid pressure history was obtained from the pulse-duplicator experiments and applied as surface pressure in the model. The differential pressure was applied to the leaflets to simulate a complete pulse cycle in Abaqus/Explicit. Contact, large deformations, and nonlinear material behavior are included in the modeling, which does not account for the nonlinear fluid-structure interaction.

Example B

In accordance with an exemplary embodiment, an apparatus includes a tubular member and a valve component. In some embodiments, the tubular member and valve component are fabricated from expanded polytetrafluoroethylene (ePTFE), elastomeric thermoplastic polyurethanes or any other elastomeric polymers or other biomaterials that can experience an irreversible and/or permanent deformation due to mechanical loads. The selected materials further provide mechanically anisotropic characteristics that are capable of being tailored for construction to provide optimal growth-accommodation, durability and hemodynamic performance. In some embodiments, thermo-responsive or light-responsive polymer or any type of external or internal stimuli responsive biomaterial that can deform irreversibly and/or permanently due to non-mechanical loads (Ph, electric field, ultrasound) can be used, as discussed hereinabove.

In some embodiments, the conduit is functionally graded to ensure patency and to prevent kinking near the valve and stented region. Grading is achieved by the grading of the polymer glue component and or use of tube material that is graded. The polymer glue material must be extended beyond the valve area to ensure a smooth transition, but not so far as to prevent permanent dilation of the conduit regions.

In some embodiments the tubular member is a 10 cm long, 12 mm diameter conduit, with a material thickness of about 0.3-0.5 mm. It can be manufactured with various other diameters, and the length can be cut as needed. The tubular member can be expanded to a diameter of 22 mm using transcatheter procedures.

Figure 17:
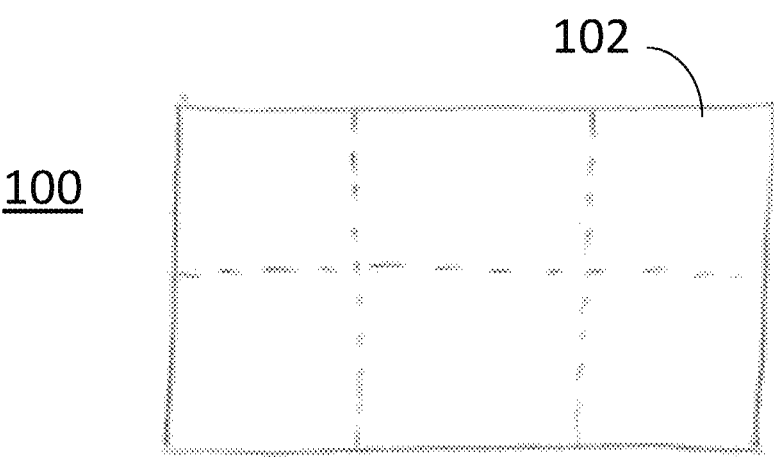
FIG. 17 illustrates an early stage in the fabrication of the valve in accordance with an exemplary embodiment of the subject matter.
Figure 18:
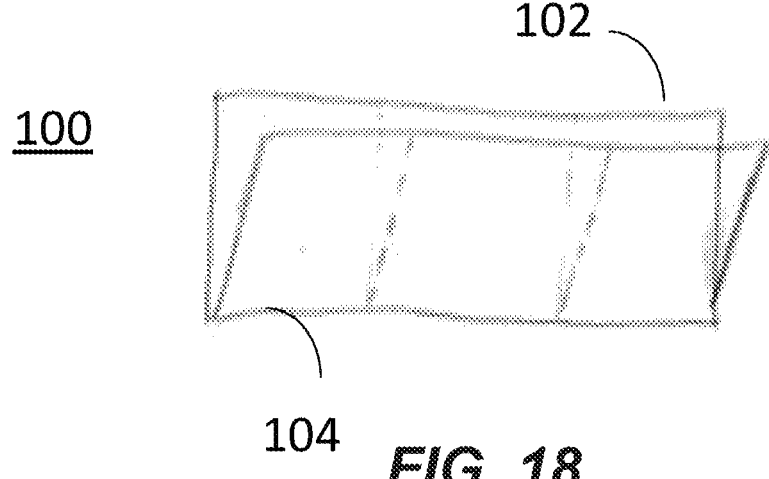
FIG. 18 illustrates a subsequent stage in the fabrication of the valve in accordance with an exemplary embodiment of the subject matter.
Figure 19:
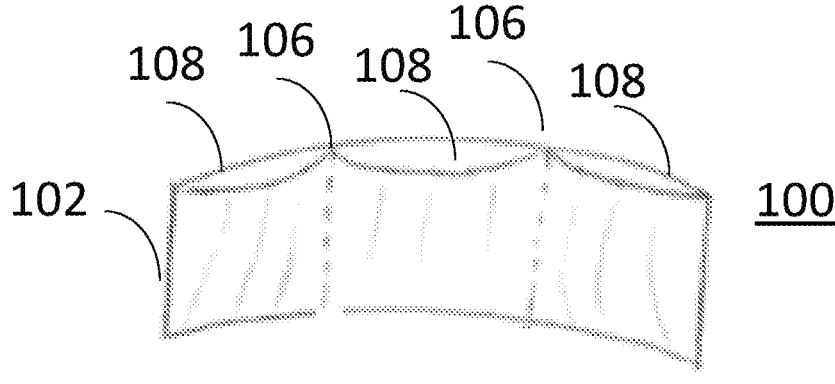
FIG. 19 illustrates a further stage in the fabrication of the valve in accordance with an exemplary embodiment of the subject matter.

As illustrated in FIGS. 17-19, the valve component 100 is made from a sheet 102 of ePTFE of about 0.1-0.2 mm thick. The sheet is folded along line 104 (FIG. 18) and thermally bonded or sutured at portions 106 to form three leaflets 108. (FIG. 19) The valve leaflets 108 expand along with the conduit and are designed to maintain valve competency after the expansion. Since the device accommodates a child's growth using non-invasive techniques, it reduces the need for repeat open-heart surgeries and lessens costs related to heart conditions.

Figure 20:
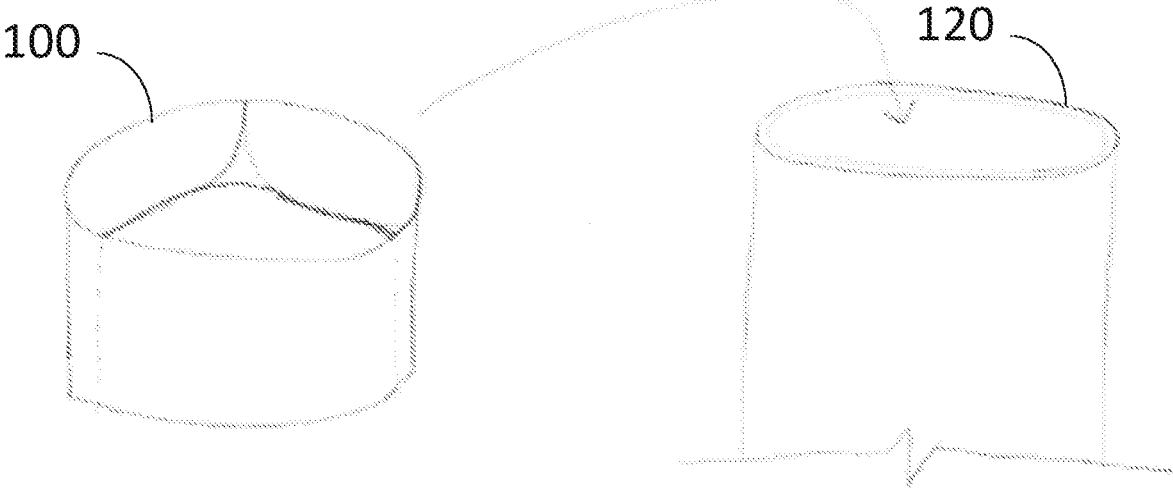
FIG. 20 illustrates the assembly of the conduit and the valve in accordance with an exemplary embodiment of the subject matter.
Figure 21:
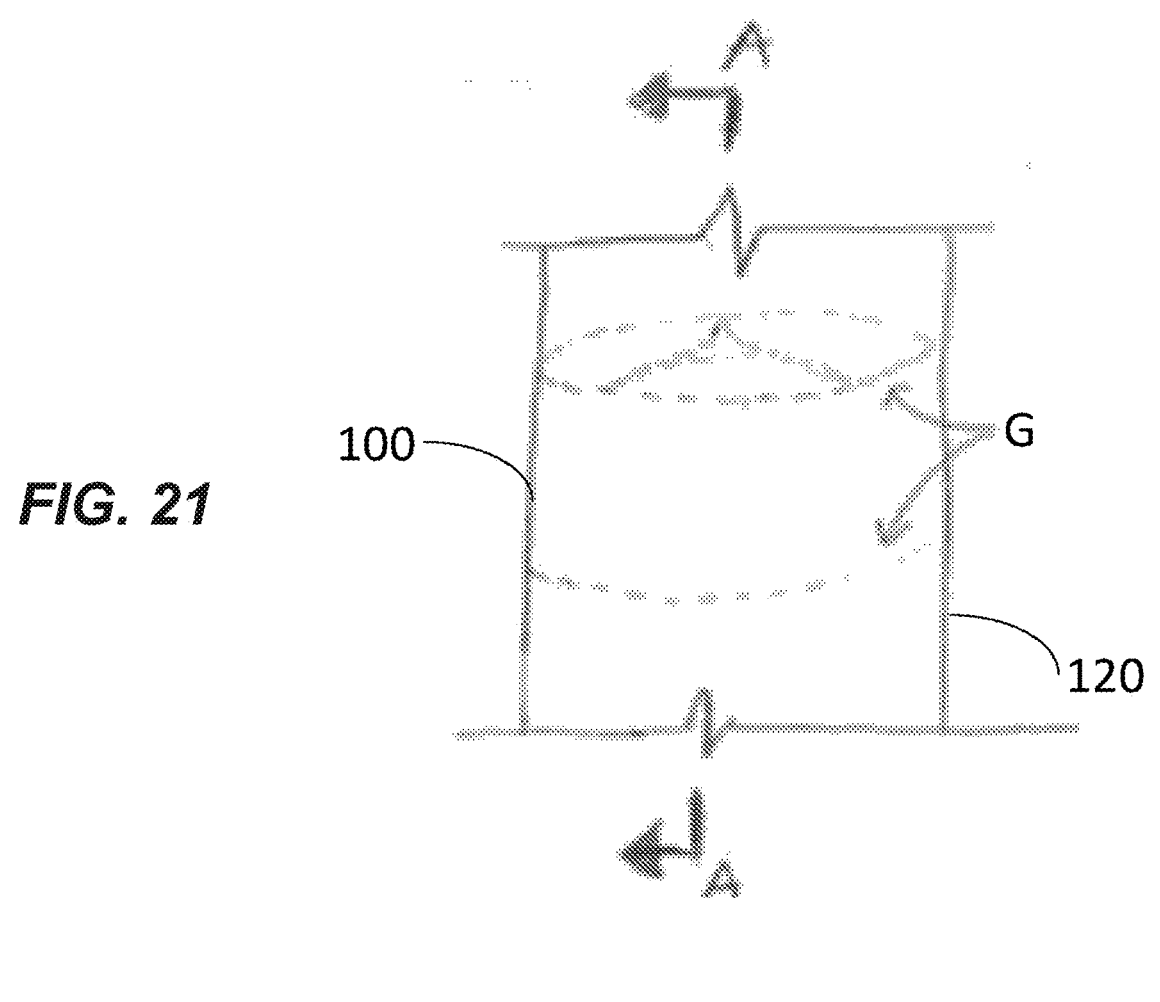
FIG. 21 illustrates a side view of the prosthetic in accordance with an exemplary embodiment of the subject matter.
Figure 22:
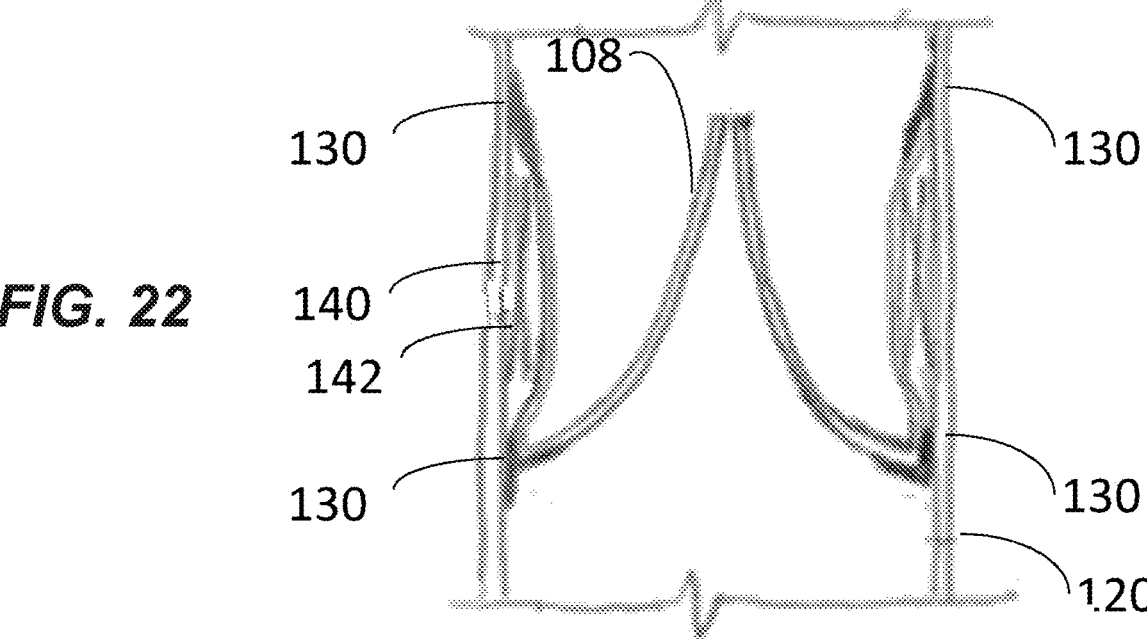
FIG. 22 illustrates a sectional view of the prosthetic, taken along line A-A of FIG. 21.

As illustrated in FIG. 20, the valve component 100 is inserted into the tubular member 120. As illustrated in FIGS. 21-22, the valve component 100 is bonded to the tubular member 120 with an elastomeric layer 130. In some embodiments, the elastomeric layer is an elastomeric thermoplastic polyurethane or any other elastomeric polymers or dilatable biomaterial. The elastomeric later acts as a polymeric glue to mechanically bond the tubular member 120 and the valve component 100 by infiltration into the porous ePTFE microstructure.

As illustrated in FIG. 21, the valve component 100 is bonded to the tubular member 120 along the circumference at two locations as indicated in dotted lines G. The circumferential lines of attachment may be continuous or intermittently disposed around the circumference of the tubular member 120. The valve component 100 can be bonded with an elastomeric glue material. Examples of such elastomeric materials with suitable melt viscosities for impregnating ePTFE microstructure (e.g., acting as glue) include polyurethanes, such as Carbothane and Elast-Eon, and silicones such as polydimethylsiloxane (PDMS).

FIG. 22 illustrates that such bonding configuration provides an annular sleeve or cavity 140 in which the expandable stent 142 is located. The cavity can also be filled with the same elastomeric glue material, such that the stent is embedded within the glue material which fills the inside of the cavity. An expandable stent 142 acts to counteract the retraction of the elastomeric layer 130. In other embodiments, the valve component is bonded by use of the polymeric elastomer along substantially its entire longitudinal dimension. The biomaterials used in the prosthesis are biostable.

This leaflets 108 are not connected directly to the outer conduit 120. The leaflets 108 are thermally fused to form a valve-in-tube configuration 100, as shown in FIG. 17-19. Then this valve-in-tube 100 is glued to the outer conduit 120. So the leaflets 198 are attached to the conduit 120 by a combination of thermal fusion and polymer glue.

The glue connection around the circumference of the conduit 120 is advantageous over a suture connection because suture holes will tend to stretch as the conduit 120 is dilated and may result in leaking. The thermal fused and glued connections are seamless and do not produce holes in the material, so there is no leakage. The thermal fused and glued connections are continuous, so they do not produce discrete stress concentrations. They provide full anchorage so that mechanical loads are efficiently transferred from the leaflets to the conduit. This permits a more efficient leaflet design as the unique mechanical properties of ePTFE (e.g. anisotropy in elasticity, viscoelasticity, and plasticity) can be fully realized.

Once the prosthesis is assembled in the configuration shown in FIG. 22, both the leaflets of the valve and the tubular member are a capable of irreversible radial expansion of approximately double the original dimension or more, e.g., from 12 mm to 24 mm. In other embodiments, the original dimension is 8 mm for neonatal applications In use, the prosthesis is implanted surgically, via open-heart surgery, or percutaneously (using the transcatheter approach) at the initial, i.e., smaller diameter. As the child grows, it is necessary to expand the prosthesis to a second, i.e., larger diameter. A balloon catheter is introduced into the prosthesis to enlarge the prosthesis, including the valve component, to second diameter. During the child's growth, this procedure of enlarging the prosthesis by use of balloon dilation transcatheter approach may be repeated several times, avoiding the need for surgical intervention.

The device stays deformed permanently after dilation due to the irreversible and/or permanent deformation mechanisms of polymers, e.g., ePTFE, and the presence of the stent positioned between the valve component and the tubular member.

The plurality of leaflets define a height of coaptation, length of the leaflet free edge, shape of the leaflet free edge, and radial and circumferential curvatures of the leaflet. These design features of the valve component allow the valve component to maintain integrity following expansion of the prosthesis. As is understood in the art, the integrity of the valve component refers continued acceptable functionality of the valve component, e.g., functioning with acceptable levels of regurgitation.

For example, the valve component features increased height of coaptation and increased length of the leaflet free edge at the time of installation. As illustrated in FIG. 23, the valve leaflets 108 initially include significant coaptation C1 along their free (top) edge. A balloon catheter 200 is used to radially expand the prosthesis from "Diameter A" (FIG. 24) to "Diameter B." (FIG. 25). It understood that the term "diameter" refers to the diameter of the tubular member 120 and the outer periphery of the valve component. Once in the enlarged configuration, the valve leaflets 108 retain sufficient coaptation C2 to maintain the integrity of the valve component. (FIG. 26).

As shown in FIG. 27, the valve component 100 also exhibits extra length of the free edge 112 of the leaflets 108 in the initial configuration of "Diameter A." When expanded to "Diameter B," the valve continues to maintain integrity, in part d to the extra length of the free edge. (FIG. 28). The shape of the leaflet free edge, and radial and circumferential curvatures of the leaflet as shown in FIG. 27 are designed such that, upon expansion to Diameter B (FIG. 28), the valve component 100 maintains its integrity.

An exemplary method of installing the transcatheter dilatable valve tube prosthesis in the body conduit of a patient includes providing the transcatheter dilatable valve tube prosthesis as described herein. The prosthesis includes a tubular member 1200 capable of plastic deformation from a dimension to a second dimension, a valve component 100 having a plurality of leaflets 108. The valve component 100 is capable of expansion from the first dimension to the second dimension. The valve component 100 secured to an interior portion of the tubular member 120 by an elastomeric glue at two circumferential portions defining an annular cavity 140 therein. An expandable stent 142 is positioned in the annular cavity 140 between the valve component and the tubular member. The transcatheter dilatable valve tube prosthesis is inserted into the body conduit of the patient, and secured to the body conduit, e.g., by sutures. A balloon catheter 200 is inserted into the transcatheter dilatable valve tube prosthesis; and expanded; thereby expanding the tubular member from the first tubular member dimension to the second tubular member dimension, while maintain the integrity of the valve component 100 at the enlarged dimension.

The prosthesis design described herein provides a number of advantages, for example, a durable expandable device with a robust connection between the valve and the conduit; sutureless fabrication provides better reproducibility and lower costs of production using existing industrial fabrication techniques; sutureless fabrication also provides no suture holes, and no hemostasis issues at the junction tube/valve. Further, the use of a stent eliminates uncertainty regarding viscoelastic retraction of the ePTFE to its final diameter after expansion and provides reproducible results in the operating room. The use of polymeric glue layer produce a growth-accommodating device.

Figure 30:
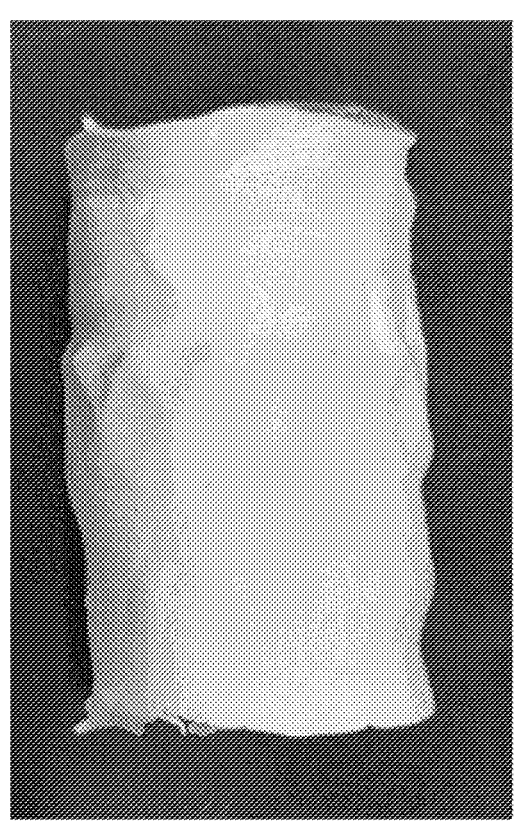
FIG. 30 illustrates a side view of the prosthetic in accordance with an exemplary embodiment of the subject matter.
Figure 31:
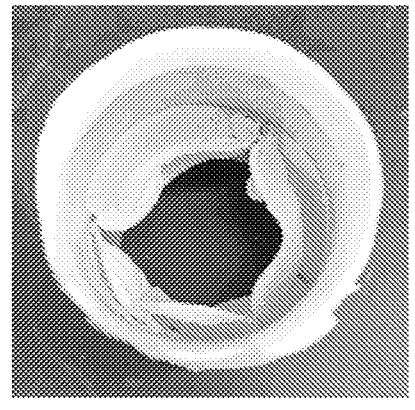
FIG. 31 illustrates an end view of the prosthetic with the valve open prior to balloon dilation in accordance with an exemplary embodiment of the subject matter.
Figure 32:
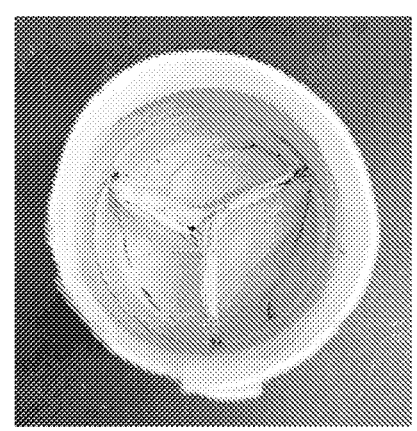
FIG. 32 illustrates a side view of the prosthetic with the valve closed prior to balloon dilation in accordance with an exemplary embodiment of the subject matter.
Figure 33:
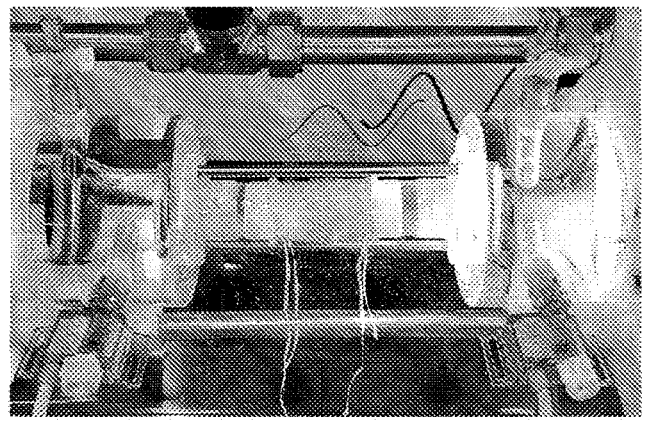
FIG. 33 illustrates the prosthesis in a testing rig, prior to balloon dilation
Figure 34:
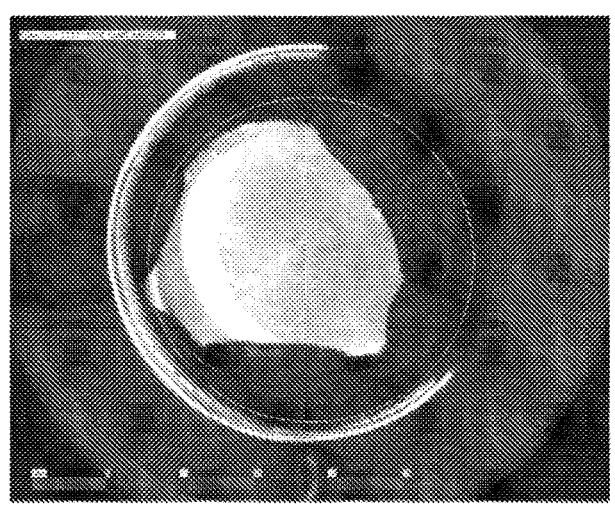
FIG. 34 illustrates an end view of the prosthesis with the valve in the open position in the first, initial diameter prior to balloon dilation.
Figure 35:
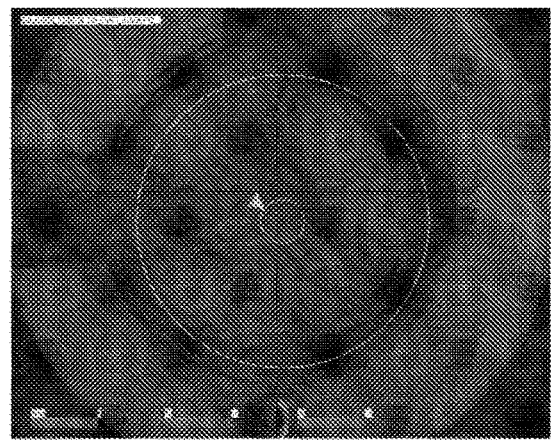
FIG. 35 illustrates an end view of the prosthesis with the valve in the closed position in the first, initial diameter prior to balloon dilation.

In vitro testing was performed on the prosthesis (FIGS. 30-32) prior to balloon dilation using a pulse duplicator (BDC Laboratories, Wheat Ridge, Colorado) (FIG. 33) at a heart rate of 70 bpm, mean pulmonary pressure of 15 mmHg, and cardiac output of 4.74 L/min. The 22 mm diameter device (FIGS. 30-32) showed basic valve competency, with a regurgitant fraction of 6.0%, effective orifice area of 1.99 cm², and a mean pressure differential of 7.4 mmHg (FIGS. 34-35).

According to another embodiment, a cardiovascular stent design optimization method is described herein, with exemplary application to a pediatric balloon-expandable prosthetic heart valve. The exemplary design includes a polymeric valve situated inside of an expandable polymeric conduit. A polymeric glue layer can be inserted between the polymeric valve and expandable polymeric conduit. In some cases, radial retraction of the region occurs after expansion. The stent configuration described herein is designed to counteract the retraction and maintain a desired diameter throughout the device after a single non-compliant balloon dilation procedure.

In some embodiments, the valve is constructed using a polymeric material (similar to that of the conduit) and is adhered to the conduit via an intermediate polymeric glue layer. After initial device implantation, valve expansion can occur through transcatheter balloon dilation of the entire device, which would permanently deform to a larger desired diameter. However, the region in which the polymeric glue resides would likely undergo less permanent dilation than the rest of the device due to differences in the mechanical properties of the device material and the polymeric glue. In order to counteract the anticipated retractive behavior in the valve region, a stent may be inserted between the inner valve structure and the outer conduit.

Appropriate materials for the stent include nitinol 316L stainless steel, cobalt chromium, and various polymers. In some embodiments, 316L stainless steel and L605 cobalt chromium are used although other materials could be substituted using a similar methodology as described herein.

The impact of variations in geometric parameters such as the width and thickness of the stent struts, in addition to the number of circumferential patterns is examined. While most works typically utilize similar low-dimensional geometric parameterizations or compare the performance of existing stent geometries, some works increase the design freedom using techniques in shape optimization with mesh-morphing or a design parameterization based on nonuniform rational B-splines (NURBS). These more complex strategies may eventually be included in the procedure proposed herein. Desired mechanical properties vary across the literature but generally include measures of fatigue resistance, peak stress or strain, radial recoil, foreshortening, flexibility, and expansion uniformity (e.g. whether the dog-boning phenomena occurs). Within the specific context considered herein, we are interested in achieving uniform permanent expansion of the entire device using a non-compliant balloon, in addition to performance metrics related to stent durability.

Typical stent expansion finite element simulations involve large amounts of deformation, contact, and material nonlinearity which, consequently, greatly increases the computational expense. In order to alleviate some of the numerical burden, the majority of existing works employ surrogate-based optimization techniques using relatively few detailed computational analyses. To this end, Kriging-based surrogate models have dominated much of the literature although others have used polynomial based response surfaces, or provide a comparison of multiple approaches. Most of the literature also utilizes a design-of-experiments (DOE) type sampling strategy for the parameter space, such as Latin hypercube sampling, in an attempt to reduce the number of high fidelity simulations required for a sufficiently accurate fit of a surrogate model. Due to the relatively few design parameters we employ and the observed smooth behavior of the performance metrics we are interested in, a different strategy based on cubic interpolation over a uniform grid is used. The defined multiobjective optimization problem is then solved using a highly effective algorithm for obtaining the set of Pareto-optimal designs (we note that many of the existing works employ the NSGA-11 algorithm for this purpose).

We should also note that most of the aforementioned works generally only employ structural finite element analyses due primarily to the generally larger numerical expense of computational fluid dynamics (CFD) simulations. However a few works also investigate stent design for hemodynamic performance. In the current context, the stent is not directly in the flow path, therefore mitigating the need for CFD simulations in this particular stage of the design process.

Figure 36:
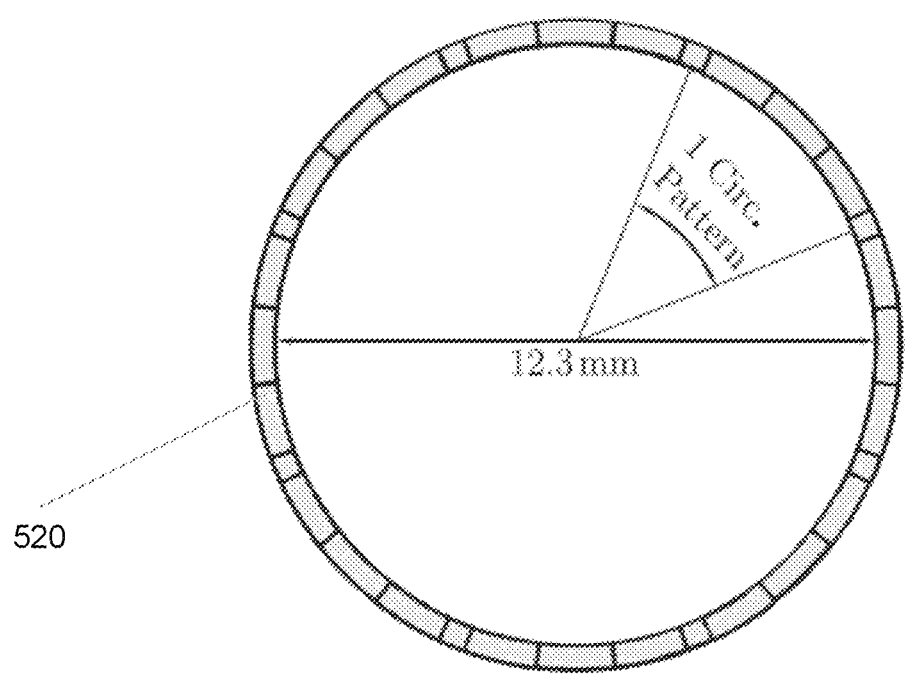
FIG. 36 is a cross-sectional end view of a stent in accordance with an exemplary embodiment of the disclosed subject matter.
Figure 37:
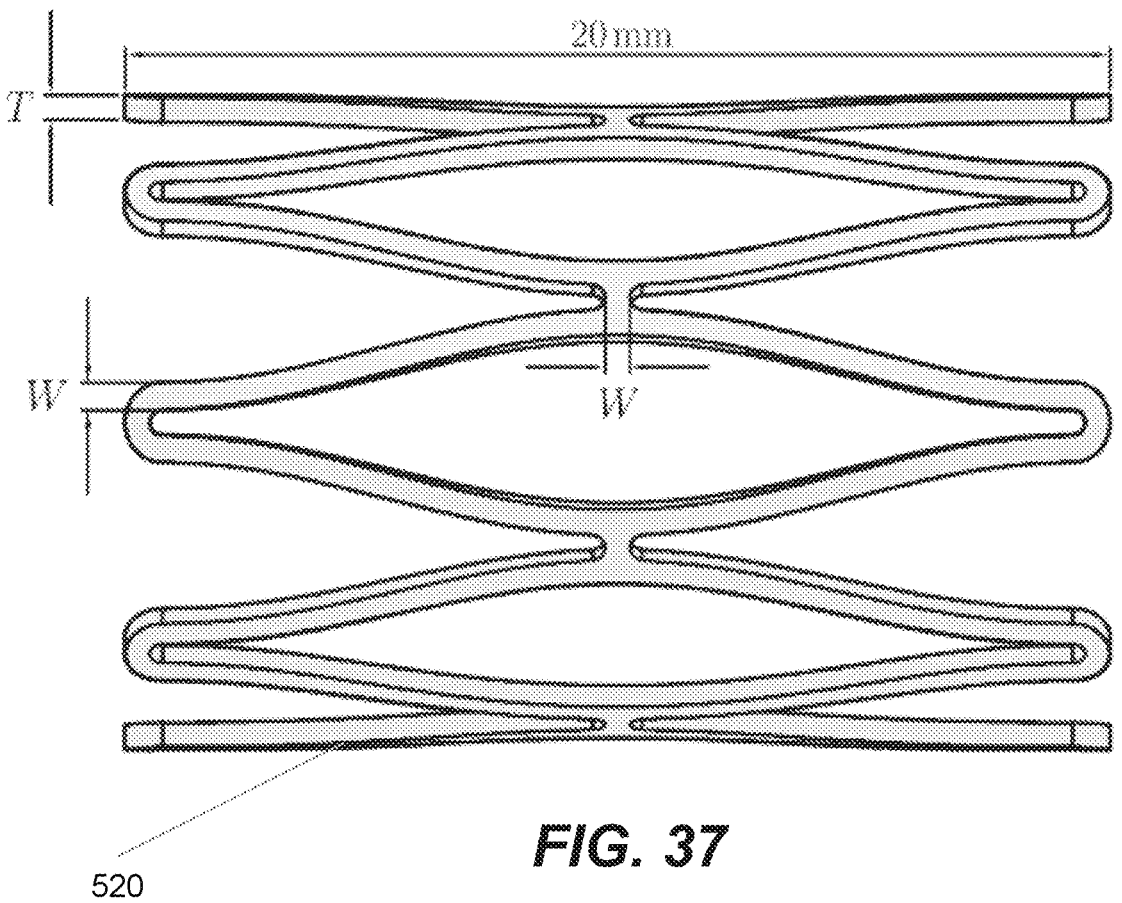
FIG. 37 is a side view of a stent in accordance with an exemplary embodiment of the disclosed subject matter.
Figures 38, 39:
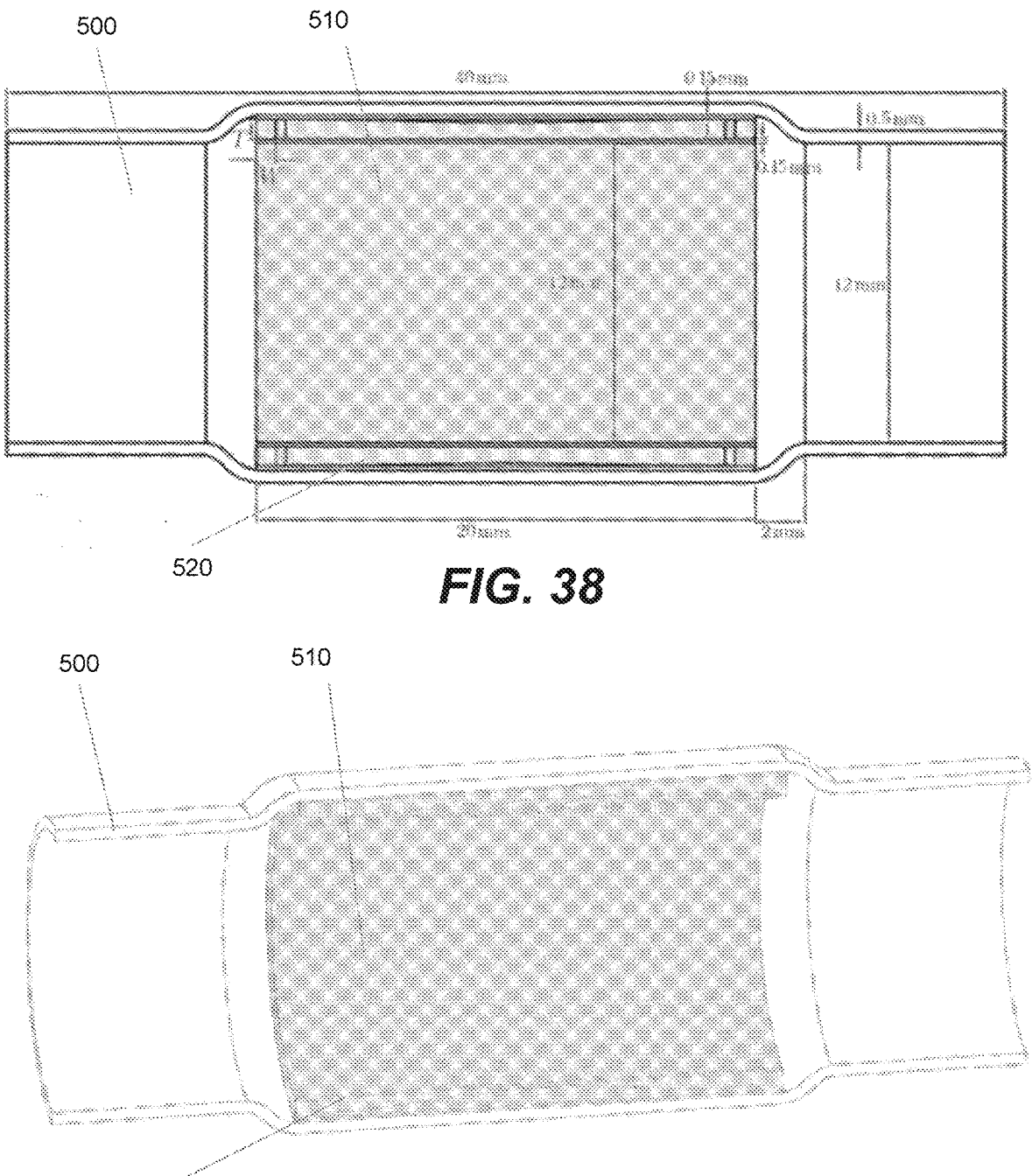
FIG. 38 is cross-sectional side view illustrating the conduit, stent and polymeric glue in accordance with an exemplary embodiment of the disclosed subject matter.
FIG. 39 is isometric side view in cross-section illustrating the conduit, stent and polymeric glue in accordance with an exemplary embodiment of the disclosed subject matter.

Geometric parameterization. The impact of variation in three stent geometric parameters (i.e., the strut width, W, strut thickness, T, and number of circumferential patterns, NCP) on particular performance metrics are considered, described further herein, along with two different stent materials (316L stainless steel and L605 cobalt chromium). The outer conduit 500 is constructed from e-PTFE, while Carbothane' is used as the polymeric glue. The numerical approximation and parameterization of the stent geometry are illustrated in FIGS. 36-37. A single circumferential pattern is identified, and the variable NCP is used to represent the total number of circumferential patterns, while in FIGS. 38-39 the numerical approximation of the assembly including the stent 520, conduit 500, and polymeric glue layers 510 is shown.

The inner e-PTFE valve geometry has been omitted from this analysis in an effort to decrease the computational complexity. This approximation is justified due to the low thickness and stiffness of the inner e-PTFE layer compared to the remainder of the structure. Creation of the stent CAD geometry was performed via the Python scripting interface of the CAD software, FreeCAD, while the conduit and glue layers were constructed via the Python scripting interface of Abaqus. As will be discussed herein, a non-compliant balloon (used for device expansion) is approximated as a rigid, radially expanding cylindrical surface with an initial diameter of 12 mm.

Numerical simulation setup. As discussed above, the numerical models were created and executed using the Python interface to the commercial finite element code. Symmetry boundary conditions are employed in a cylindrical coordinate system in order to significantly reduce computational expense. Each geometry is partitioned in order to facilitate the creation of a high quality hexahedral mesh. The volumetric components of the model (i.e. the conduit, polymeric glue, and stent) are all meshed with C3D20H hybrid finite elements, which interpolate the displacement field with nearly second order accuracy and also consist of a linear pressure field interpolation. Each element is fully integrated with a 27-point gauss quadrature rule. Although these elements have relatively high computational cost, we employ them for accuracy and to alleviate any potential concern of volumetric or shear locking. In addition, the fully-integrated elements in the stent region ensure 9 to 12 integration points through the stent cross-section which provides the high accuracy sought when computing metrics associated with ductile failure and fatigue presented herein. A non-compliant balloon is approximated using a rigid cylindrical surface mesh consisting of reduced integration membrane elements (M3D4R) with completely specified nodal boundary conditions. Hard contact is used between the outer balloon surface and the inner diameter of the device with an assumed friction coefficient of 0.01. The constitutive models and calibrated constants for each material (i.e., 316L stainless steel, L605 cobalt chromium, e-PTFE, and Carbothane polymeric glue) are presented in Appendix A.

Figure 40:
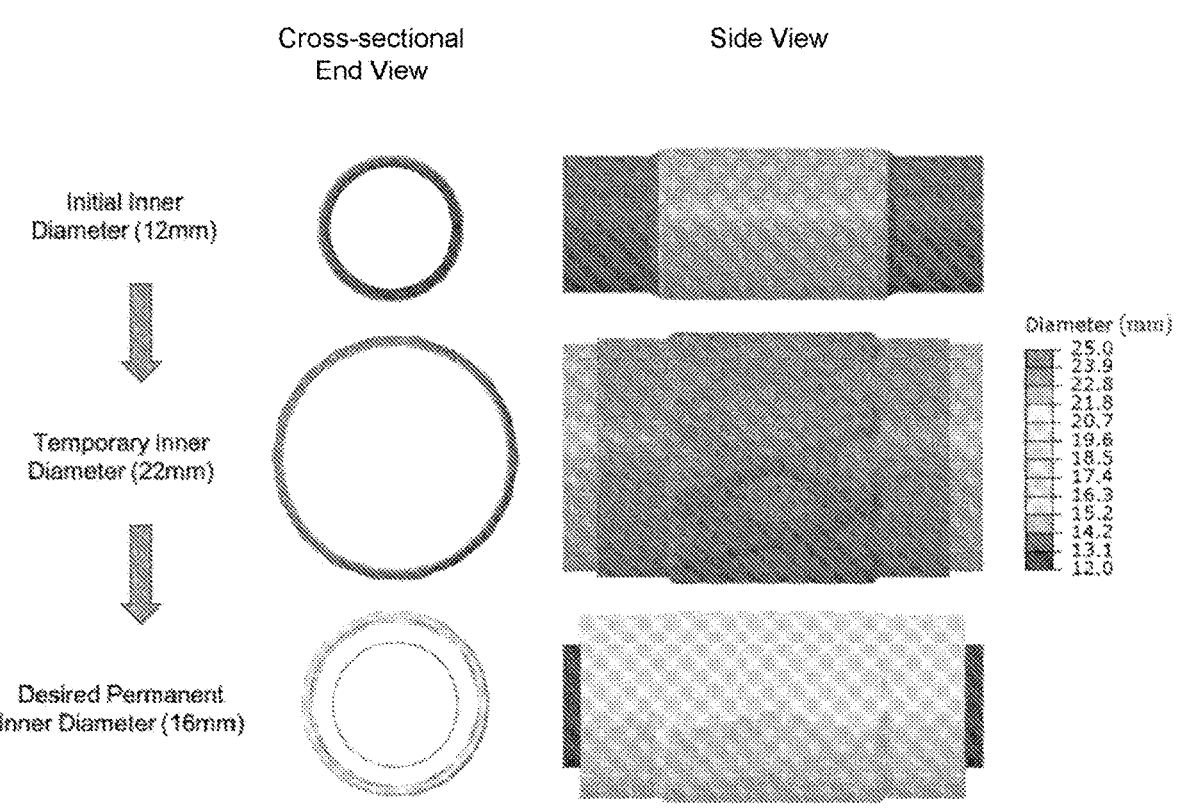
FIG. 40 is a schematic view illustrating a sequence from top to bottom, from the intial state, to a temporary configuration, to the desired permanent diameter of the conduit.

FIG. 40, which illustrates a simulation sequence in which the cylindrical rigid balloon is radially expanded from an initial diameter of 12 mm to 22 mm temporarily, followed by radial retraction until the balloon is no longer in contact with the device, i.e., 16 mm. It is numerically predicted that the temporary 22 mm expansion diameter would achieve the desired permanent expanded diameter of 16 mm in a homogeneous e-PTFE conduit with 12 mm initial inner diameter and 0.5 mm thickness. Without the polymeric glue, the desired expanded diameter would be realized if the device were expanded temporarily to 22 mm.

On this basis, the stent configuration is designed to counteract the retractive forces of the polymeric glue as discussed hereinabove. Once the balloon is removed, a typical pulmonary diastolic pressure loading of 10 mm Hg is quasistatically applied to the inner surfaces of the device, followed by an increase to a systolic pressure of 30 mm Hg.

Figure 41:
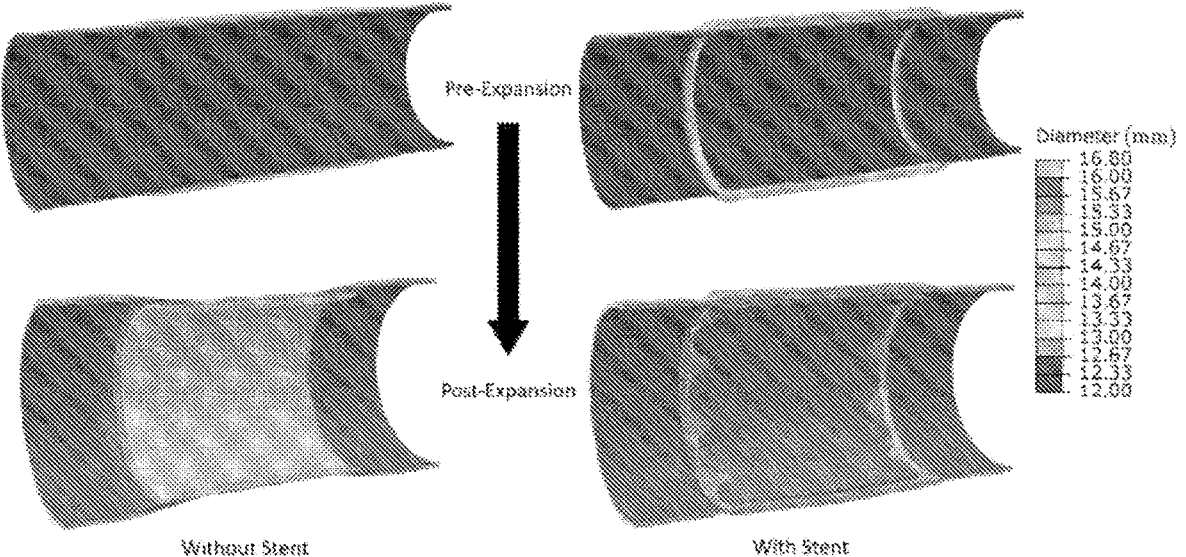
FIG. 41 is a schematic view illustrating a sequence from top to bottom, of pre-balloon expansion (top) to post-balloon expansion (bottom) for a conduit without a stent (left) and with a stent (right).
Figure 42A:
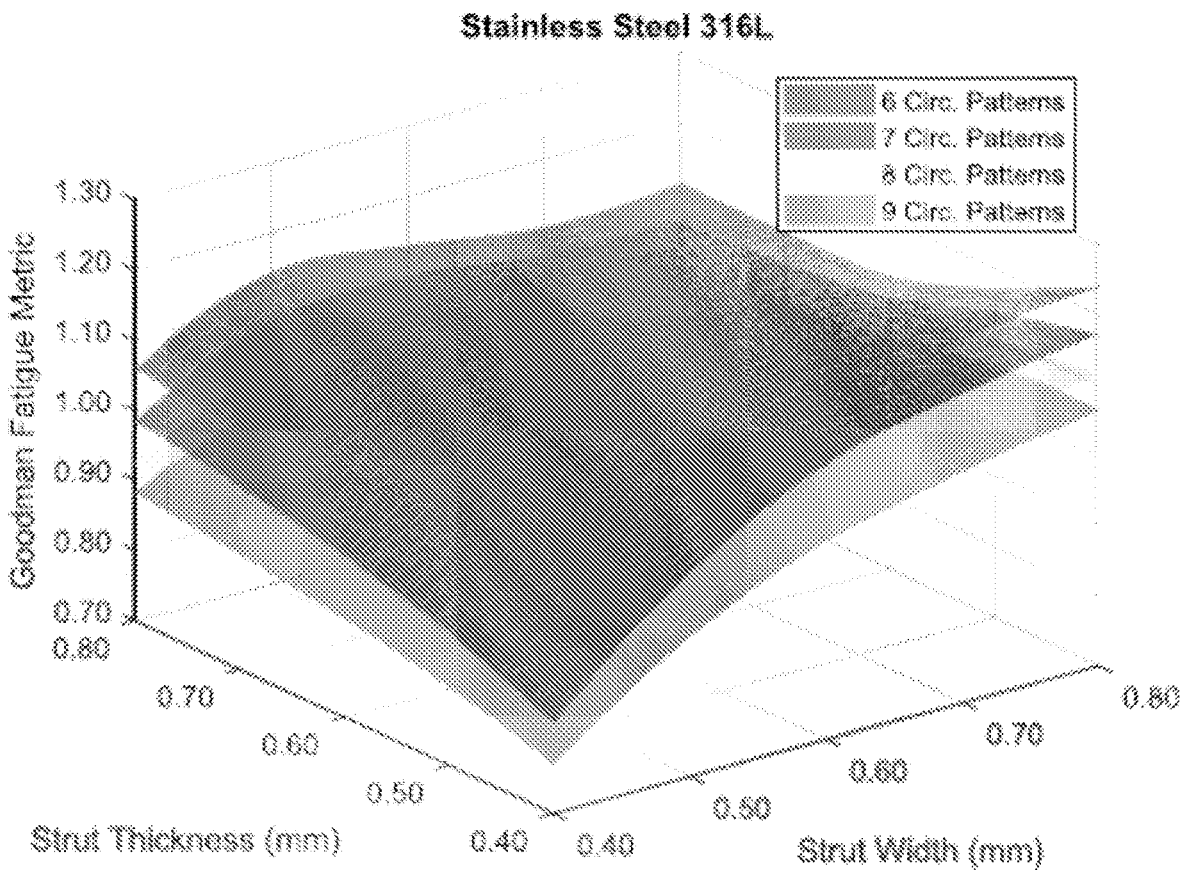
FIG. 42A illustrates the GF surrogate model for 316L stent material for a number of circumferential patterns, NCP.
Figure 42B:
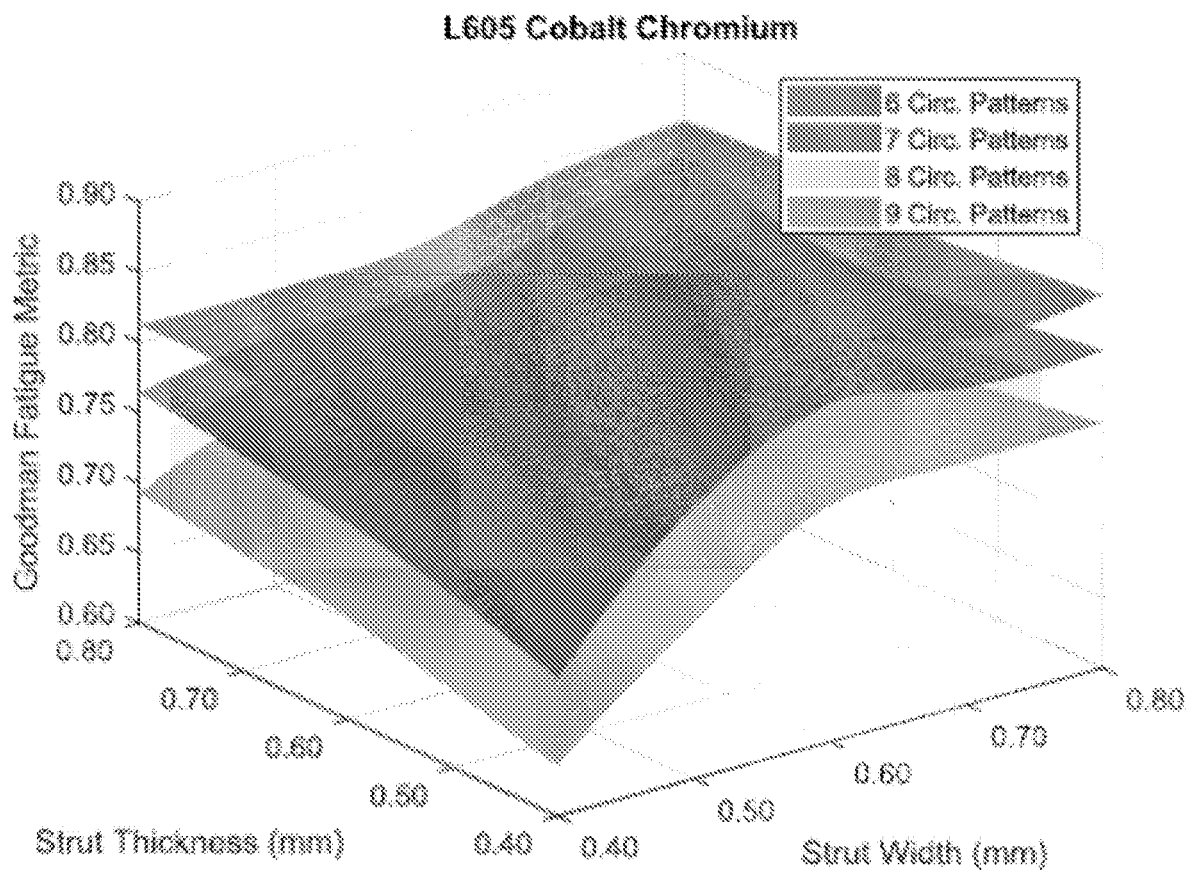
FIG. 42B illustrates the GF surrogate model for L605 stent material for a number of circumferential patterns, NCP.
Figure 43A:
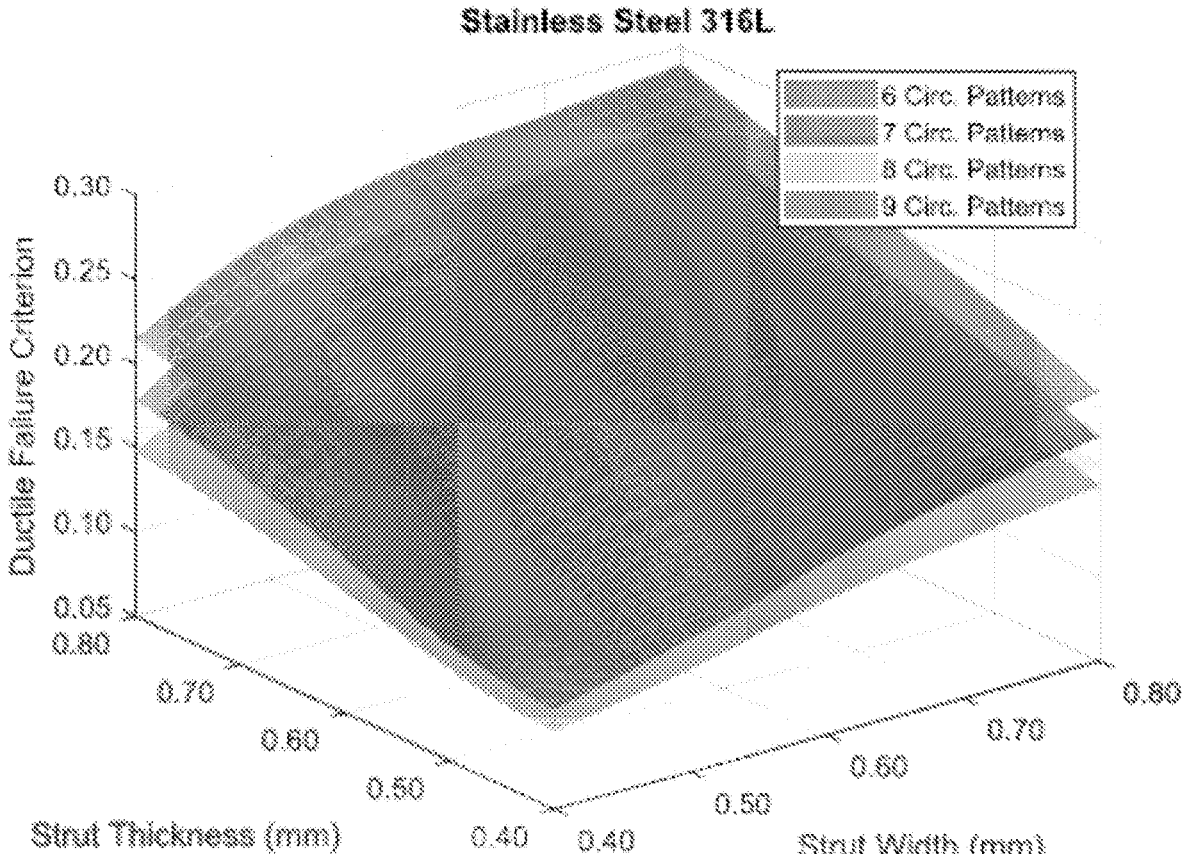
FIG. 43A illustrates the DF surrogate model for 316L stent material for a number of circumferential patterns, NCP.
Figure 43B:
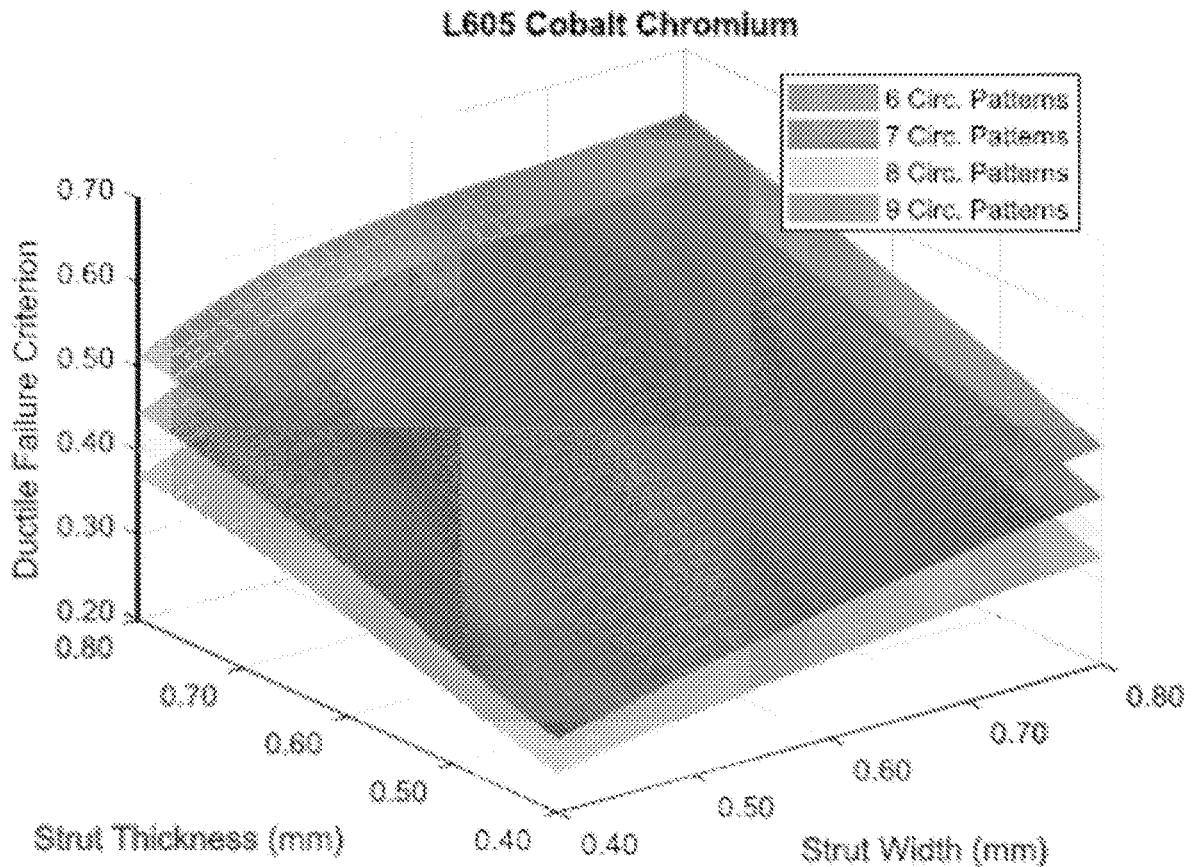
FIG. 43B illustrates the DF surrogate model for L605 stent material for a number of circumferential patterns, NCP.

Each model typically consists of between 235-362k degrees of freedom and required 3-5 hours running on a workstation with an Intel Xeon E3-1281 CPU and 16 GB of RAM. For convenience, a typical numerical simulation sequence is illustrated in FIG. 40, which illustrates a simulation sequence from initial configuration of 12 mm, to temporary rigid balloon expansion of 22 mm, to desired permanent diameter of 16 mm at which the systolic and diastolic pressures are subsequently applied. The retractive behavior of the polymeric glue it demonstrated in FIG. 41 via comparison with and without a stent. It is shown that in the homogeneous e-PTFE conduit the 16 mm diameter is realized while the polymeric glue limits the permanent diameter in the valved region to 14 mm.

Performance metrics. Exemplary metrics used to develop the stent include the mean deviation $D_{mean}(\chi)$ and the standard deviation $D_{stddev}(\chi)$ of the predicted permanent inner diameter in the stented region, which are represented by the function notation $D_{mean}(\chi)/D_{stddev}(\chi)$, respectively. In other words, these functions represent the mean and standard deviation of the diameter computed over all of the inner-most glue layer's inner surface nodes in the permanently deformed configuration. The shorthand symbol x to represent a realization of three geometric parameters and a selected stent material (i.e., x={W, T, NCP, StentMaterial}). The design goal of the stent is to counteract the retraction of the polymeric glue and achieve a permanent inner diameter in the valved-region, e.g., similar to that of the remainder of the conduit. As will be discussed herein, the mean permanent diameter is constrained and its standard deviation is minimized in an effort to also provide some permanent diameter uniformity. Additionally, the peak radial force required to expand the stented region is of interest since the non-compliant balloon will be required to achieve this force during the expansion procedure. This quantity is represented with the notation RF $(\chi)$.

Two additional metrics can be used that are related to the durability of the stent. Due to the very large number of typical cardiac cycles, fatigue failure is a necessary component of the stent engineering analysis. For example, the FDA recommends a Goodman fatigue life analysis for stent design for stents constructed of both 316L stainless steel and L605 cobalt chromium materials both of which are also explored herein. The Goodman criterion states that a fatigue failure may be expected when the stress amplitude $(\sigma_a \equiv \|\sigma_{max} - \sigma_{min}\|/2)$ and mean stress $(\sigma_m \equiv |\sigma_{max} + \sigma_{min}|/2)$ experienced during the pulsatile loading result in $$\frac{\sigma_a}{\sigma_{ec}} + \frac{\sigma_m}{\sigma_{UTS}} > 1$$

at some location in the structure, where the maximum and minimum of a Cauchy stress invariant (e.g., the von Mises stress is used, defined later) over a typical pulsatile load cycle is used for $\sigma_{max}$ and $\sigma_{min}$, respectively. $\sigma_N$ represents the fatigue limit, and $\sigma_{UTS}$ represents the ultimate tensile strength for the material. These material parameters ($\sigma_N$, $\sigma_{UTS}$) vary quite widely in the literature and do not guide which should be used. For 316L stainless steel, a substantial size effect well below a stent strut size of 0.5 mm. However, strut sizes equal to the minimum strut width/thickness of 0.4 mm considered in this work were not reported. Consequently, continuum macroscale properties are assumed to remain accurate in this range. As will be shown later, the optimal results for 316L are quite close to the reported 0.5 mm limit. The relevant properties are used in this work for fatigue analysis (i.e., $\sigma_N$=115 MPa, $\sigma_{UTS}$=580 MPa for 316L, and $\sigma_N$=207 MPa, $\sigma_{UTS}$=1449 MPa for L605), however it is understood other values reported in the literature could also be employed. Although fatigue safety factors may be employed, the design employed herein relies on the metric shown in Equation (1) since it is both dimensionless and directly provides a measure of constraint satisfaction for a particular stent design realization (i.e., GF ($\chi$) 1). Values greater than or equal to 1 indicate potential fatigue failure. Therefore this function is minimized, although it could also be formulated in a constraint with an upper bound equal to some fraction of 1.

$$GF(X) = \frac{max}{i \in \left[1, \ldots, N\frac{stent}{GP}\right]} \frac{\sigma_a^i}{\sigma_n} + \frac{\sigma_m^i}{\sigma_{OUTS}} \tag{1}$$

Note that $$N\frac{stent}{GP}$$

represents the total number of Gauss quadrature points in the stent finite element mesh.

While fatigue failure may be the governing failure mechanism in some cases, a stent intended to endure the very large temporary changes in diameter intended in this device may experience ductile failure during a balloon expansion procedure. Therefore, a criterion for ductile failure is incorporated into the design process. It has been known that ductile failure of metals likely depends quite strongly on the stress triaxiality, and potentially also on the Lode angle. Simple hydrostatic stress criterion worked quite well for predicting ductile failure in the range of high stress triaxiality in aluminum 2024-T351. This criterion is used as a predictive measure for ductile failure of the metals, 316L and L605, used herein. The calibration of the critical value of this criterion, $DF_{crit}$, for each of these materials is discussed in Appendix A and the normalized ductile failure criterion used during the optimization process is expressed in Equation (2).

$$DF(x) = \frac{1}{DF_{crit}} \frac{max}{1 \in \left[1, \ldots, N\frac{stent}{GP}\right]} \int_0^{\epsilon_p^i} \frac{p^i}{\sigma_{vm}^i} d\epsilon p \tag{2}$$

Representing the Cauchy stress tensor with a, cp represents the equivalent plastic strain, $$p = \frac{\sigma_{kk}}{3}$$

is the pressure stress, and $$\sigma_{vm} \equiv \sqrt{\frac{3}{2} s_{ij} s_{ij}}$$

is the Von Mises stress, where $s_{ij} = \sigma_{ij} - p\delta_{ij}$ is the stress deviator. Einstein summation convention is used, and $p\delta_{ij}$ is the Kronecker delta. Similar to the Goodman fatigue metric, ductile failure is predicted at some spatial point in the stent when DF≥1. Each of the parameters and performance metrics are summarized in Table 1, below.

TABLE 1

| Summary of design parameters and performance metrics | |
|---|---|
| Design Parameter | Summary |
| W | Stent strut width [mm] |
| T | Stent strut thickness [mm] |
| NCP | Number of stent patterns around the circumference |
| Stent Material | Construction material of the stent (either 316L or L605) |
| Performance Metric | Summary |
| $D_{mean}$ ($\chi$) | Mean permanent inner diameter in the stented region [mm] |
| $D_{stddev}$ ($\chi$) | Standard deviation of permanent inner diameter in the stented region [mm] |
| RF($\chi$) | Peak radial force exerted in the stented region during expansion [N] |
| GF($\chi$) | Goodman metric for high cycle fatigue failure prediction of the stent |
| DF($\chi$) | Hydrostatic criterion for ductile failure prediction of the stent |

Surrogate-based multi-objective optimization procedure. Due to the relatively large computational expense associated with the high fidelity finite element simulations discussed above, surrogate models are constructed for each performance metric. The multiobjective optimization problem to be solved is stated in Equation (3) as follows:

$$\underset{x}{\text{minimize}}\, GF(x),\, DF(x),\, RF(x),\, D_{stddev}(x) \qquad (3)$$

$$\text{subject to } 0.4\text{mm} \le W,\, T \le 0.8\text{mm}$$

$$16.0\text{mm} \le D_{mean}(x)$$

Note that while notationally optimization takes place over all parameters, $\chi$, numerically it is performed over W and T, solving one multi-objective optimization problem for each fixed combination of NCP and stent material. Minimizing the Goodman fatigue and ductile failure metrics provide the desired failure resistance, while minimization of the peak radial force in the stented region is also desirable in order to improve the ease of device expansion with existing non-compliant balloons. In addition to these metrics, the standard deviation of the permanent diameter in the stented region is minimized in an effort to achieve some degree of permanent diameter uniformity. Bound constraints are placed on the stent strut width and thickness, while also placing a lower bound on the mean permanent diameter in the stented region equal to the target 16 mm permanent expansion diameter.

A total of 200 high fidelity simulations are completed, including 100 with each stent material considered. Stent geometries with all combinations of five different strut widths ($W \in [0.4, 0.5, 0.6, 0.7, 0.8]$ mm), five strut thicknesses ($T \in [0.4, 0.5, 0.6, 0.7, 0.8]$mm), and four different numbers of circumferential patterns ($NCP \in [6, 7, 8, 9]$) are created using the Python interface to FreeCAD as discussed hereinabove. The 100 resulting geometries are then imported into Abaqus and numerical models are created and executed as previously described. The performance metrics outlined above are computed via an Abaqus Python post-processing script and the resulting data is tabulated into CSV files for subsequent analysis.

Since only the stent strut width, W, and thickness, T, are continuous parameters, $C^1$ cubic gridded interpolants are constructed in Matlab for each performance metric shown with fixed combination of stent material and number of circumferential patterns, NCP. These surrogate models are then used to obtain 100 Pareto optimal points by replacing the high fidelity function evaluations in Equation (3) with their respective surrogates and using the built-in "pareto-search" function based on a direct multisearch algorithm for multiobjective optimization. This surrogate-based multiobjective optimization problem is solved a total of eight times, once for each unique combination of candidate stent material and number of circumferential patterns, NCP.

Subsequently, an equally weighted, normalized aggregate objective function is constructed in order to obtain a single optimal design candidate for each stent material. The performance metrics are normalized in the following manner. Minimum and maximum values of each performance metric (say Y and corresponding $Y_{min}/Y_{max}$) are computed overall results from the 200 high fidelity simulations. A single objective optimization problem may then be stated using an equally weighted, normalized aggregate objective function.

$$\underset{x}{\text{minimize}}\, \frac{GF(x) - GF_{min}}{GF_{max} - GF_{min}} + \frac{DF(x) - DF_{min}}{DF_{max} - DF_{max}} + \qquad (4)$$

$$\frac{RF(x) - RGF_{max}}{RF_{max} - RF_{min}} + \frac{D_{stddev}(X) - D_{stddev}^{min}}{D_{stddev}^{max} - D_{stddev}^{min}}$$

$$\textit{Subject to } 0.4\text{mm} \le W,\, T \le 0.8\text{mm}$$

$$16.0\text{mm} \le D_{mean}(x)$$

The solution of this single objective optimization problem is then obtained for each fixed combination of stent material and number of circumferential patterns as previously explained. Aggregate objective values corresponding to optimized results are then used to further quantitatively compare the designs and provide a single result for the best design candidate. Obtaining a single optimized design candidate is possible since the specified unit weighting of each normalized objective within the aggregate function inherently provides a preference between non-dominated Pareto-optimal points. An overview of this process is provided in Algorithm 1. This procedure not only results in the sets of Pareto-optimal designs from the solution of Equation (3), but also the identification of an optimized design with high-performance via solution of Equation (4).

| Algorithm 1 Overview of the design optimization procedure |
| --- |
| 1: for Stent Material in [316L, L605] do |
| 2:    for NCP in [6, 7, 8, 9] do |
| 3:      for W in [0.4mm, 0.5mm, 0.6mm, 0.7mm, 0.8mm] do |
| 4:       for T in [0.4mm, 0.5mm, 0.6mm, 0.7mm, 0.8mm] do |
| 5:       Perform high fidelity numerical simulation and compute ($D_{mean}$, $D_{stddev}$, RF, GF, DF) |
| 6:      end for |
| 7:    end for |
| 8:    Construct cubic surrogate model for each performance metric |
| 9:    Solve Equation (3) for 100 Pareto-optimal (W, T) pairs and store |
| 10:    Solve Equation (4) for a single optimal (W, T) pair and store |
| 11:   end for |
| 12: end for |
| 13: Identify parameters producing lowest aggregate objective value in Equation (4) |

Figure 44A:
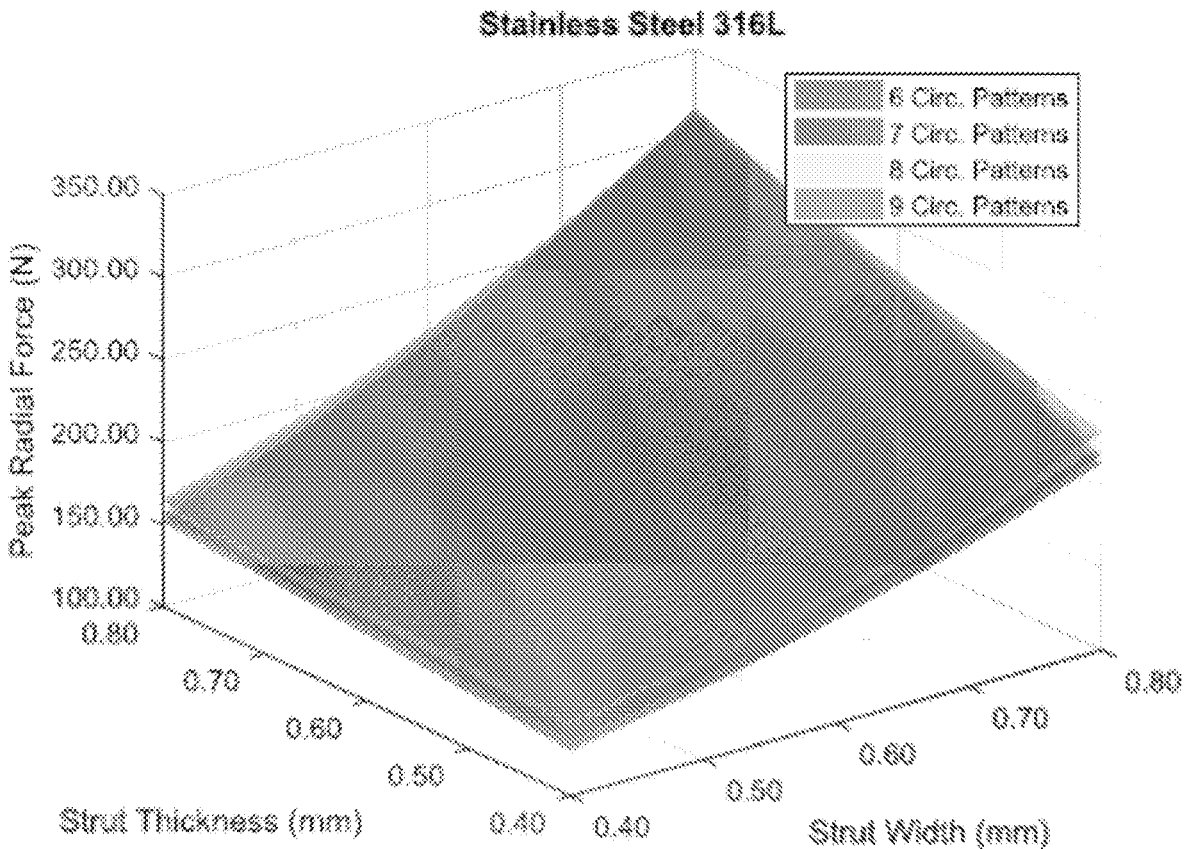
FIG. 44A illustrates the RF surrogate model for 316L stent material for a number of circumferential patterns, NCP.
Figure 44B:
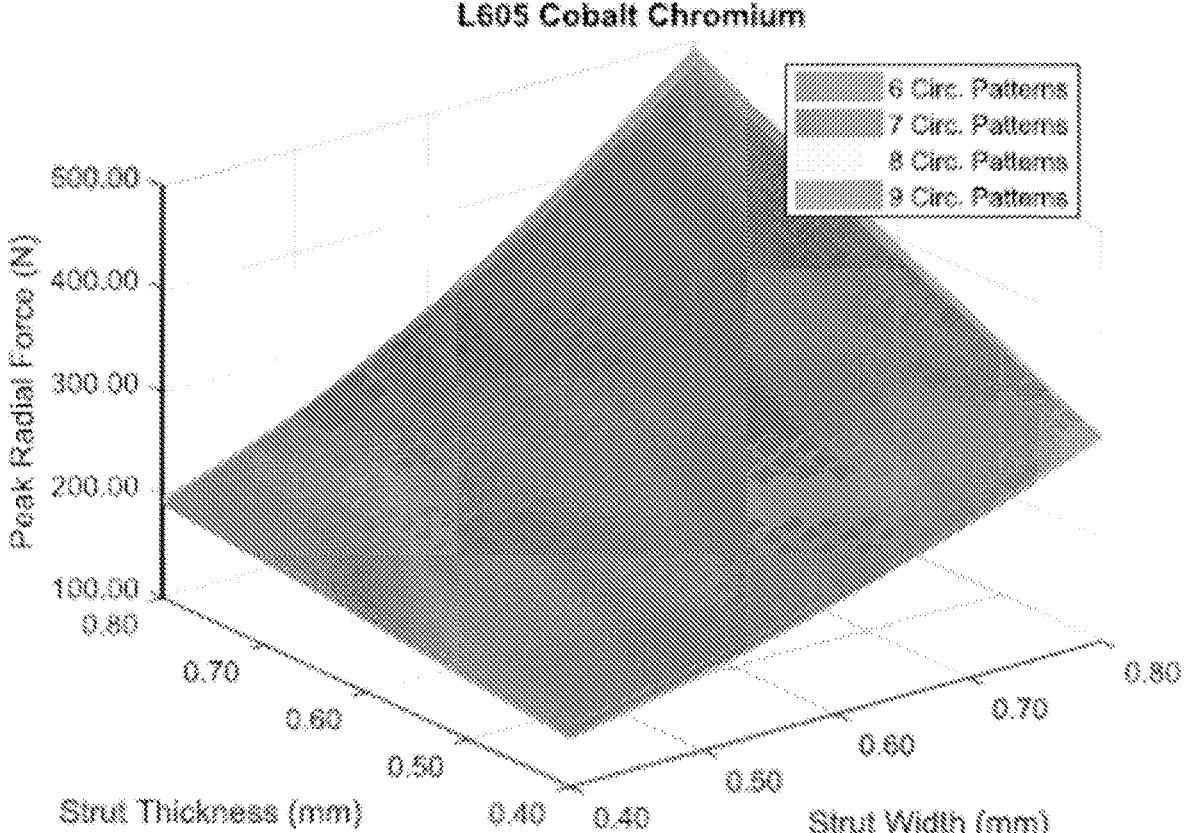
FIG. 44B illustrates the RF surrogate model for L605 stent material for a number of circumferential patterns, NCP.
Figure 45A:
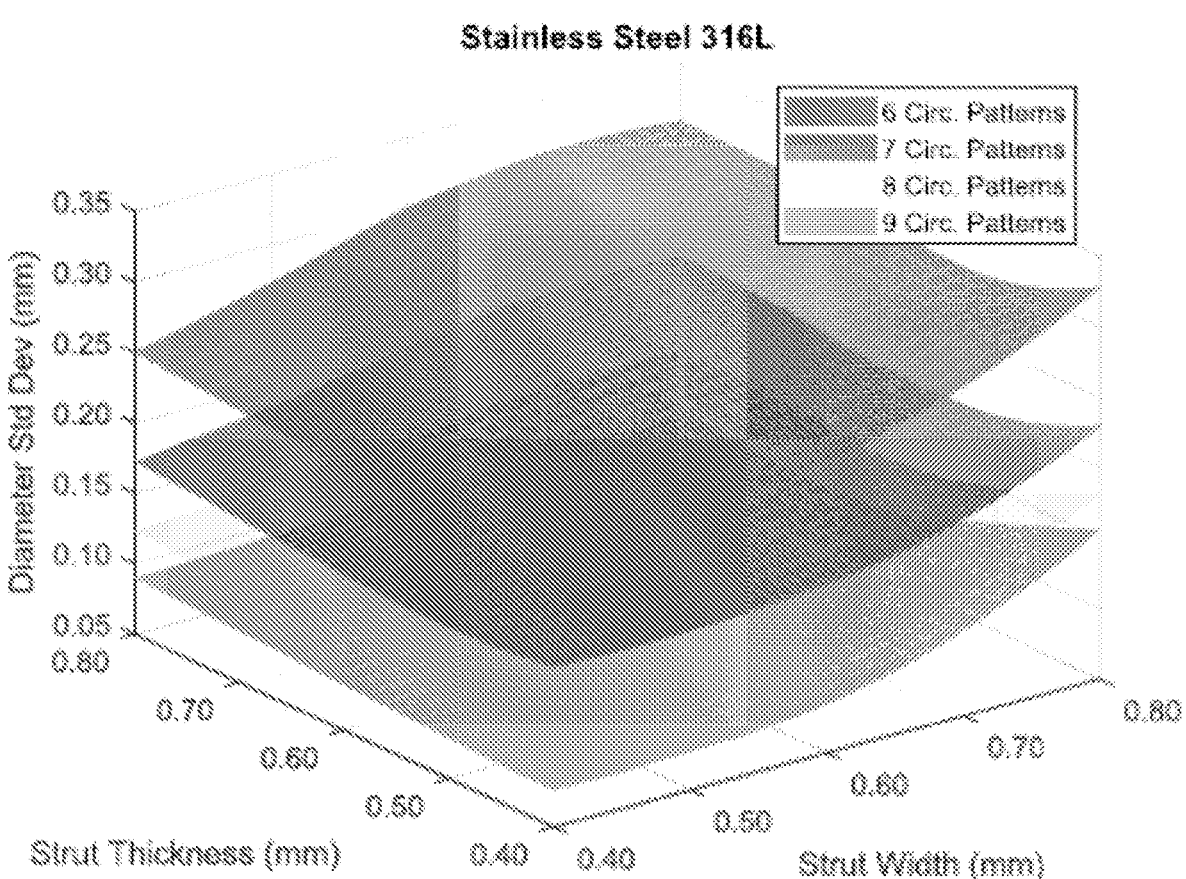
FIG. 45A illustrates the $D_{stddev}$ surrogate model for 316L stent material for a number of circumferential patterns, NCP.
Figure 45B:
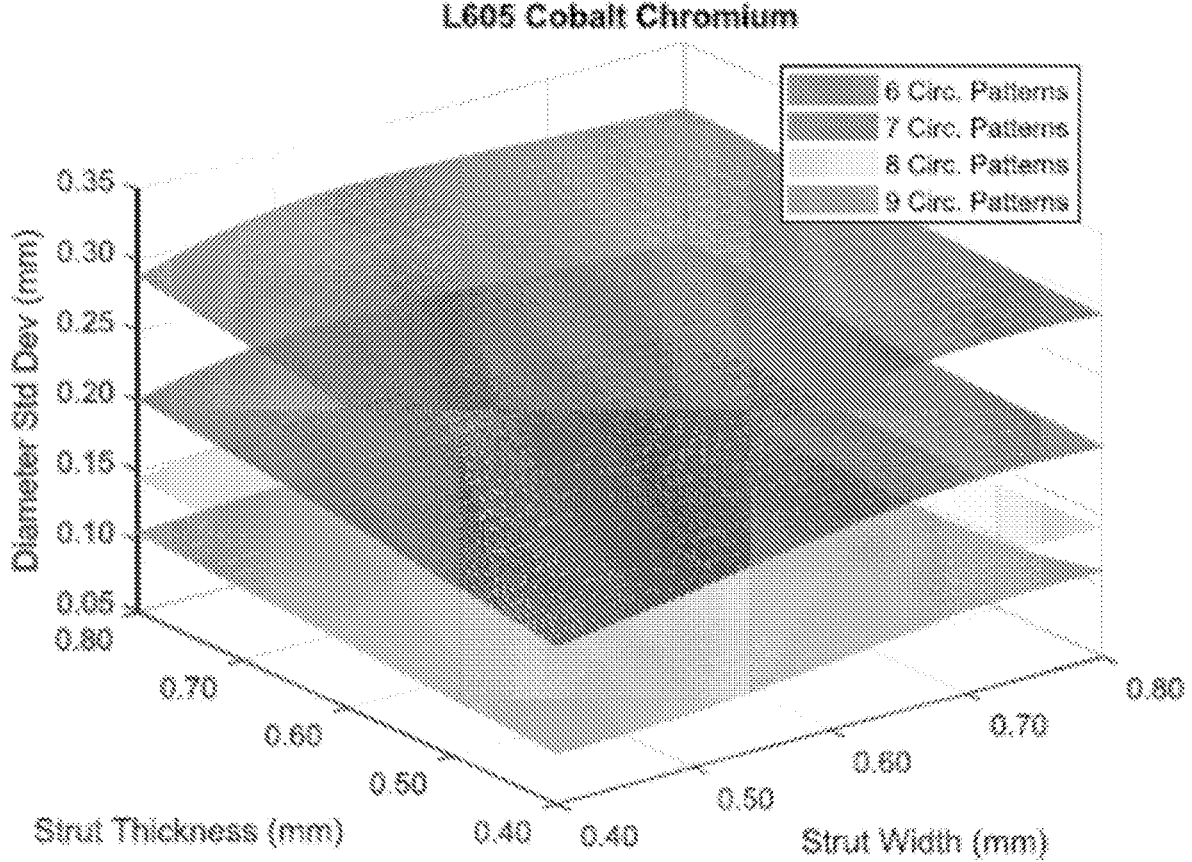
FIG. 45B illustrates the $D_{stddev}$ surrogate model for L605 stent material for a number of circumferential patterns, NCP.

Numerical results. The cubic surrogate models for each function are illustrated in FIGS. 42A-45B below. The non-linearity of the Goodman fatigue metric is clear from FIGS. 42A-42B. While the normalized ductile failure criterion is generally lower for 316L with respect to L605, the Goodman fatigue metric indicates much better fatigue performance for L605. This is at least partially explained by the seemingly high ultimate tensile strength stated in much of the literature for L605, as previously mentioned. Additional test data should be obtained to validate the Goodman parameters for the material thickness range of interest. Also, most of design region places the Goodman metric above 1 for the 316L stent, indicating a potential fatigue failure. FIGS. 44A-44B illustrate that the peak radial force required to expand the stented region of the device generally increases with the number of circumferential patterns, NCP, although this observation is reversed for large enough strut width (W) and thickness (T). The other metrics (GF, DF, $D_{stddev}$) all increase with a decrease in NCP for fixed Wand T, showing a clear benefit to including a larger number of circumferential patterns.

As discussed above, these surrogate models were then used to obtain a set of 100 Pareto-optimal points for the multiobjective optimization problem stated in Equation (3).

Figure 46A:
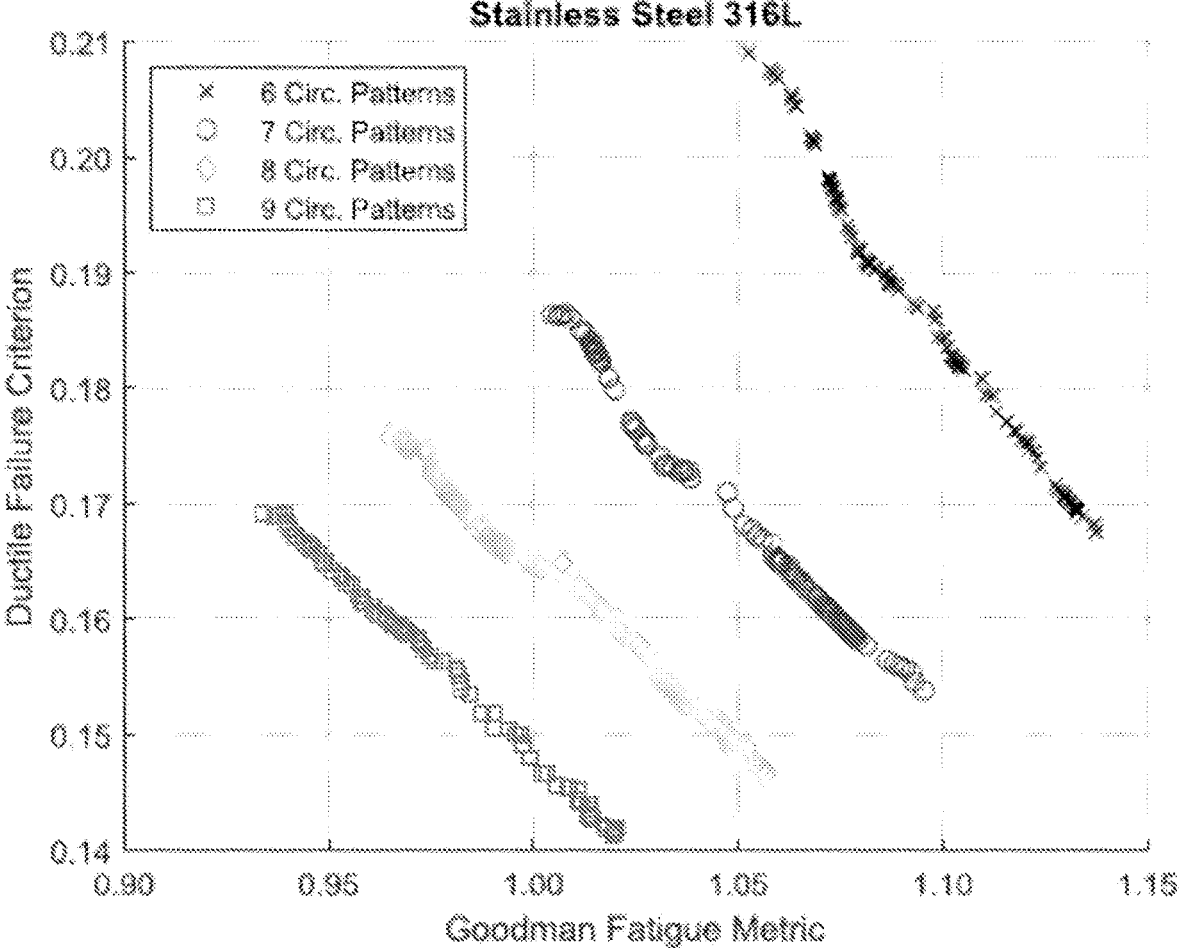
FIG. 46A illustrates pareto-optimal points illustrating the trade-off between GF and DF for 316L stent material for a number of circumferential patterns, NCP.
Figure 46B:
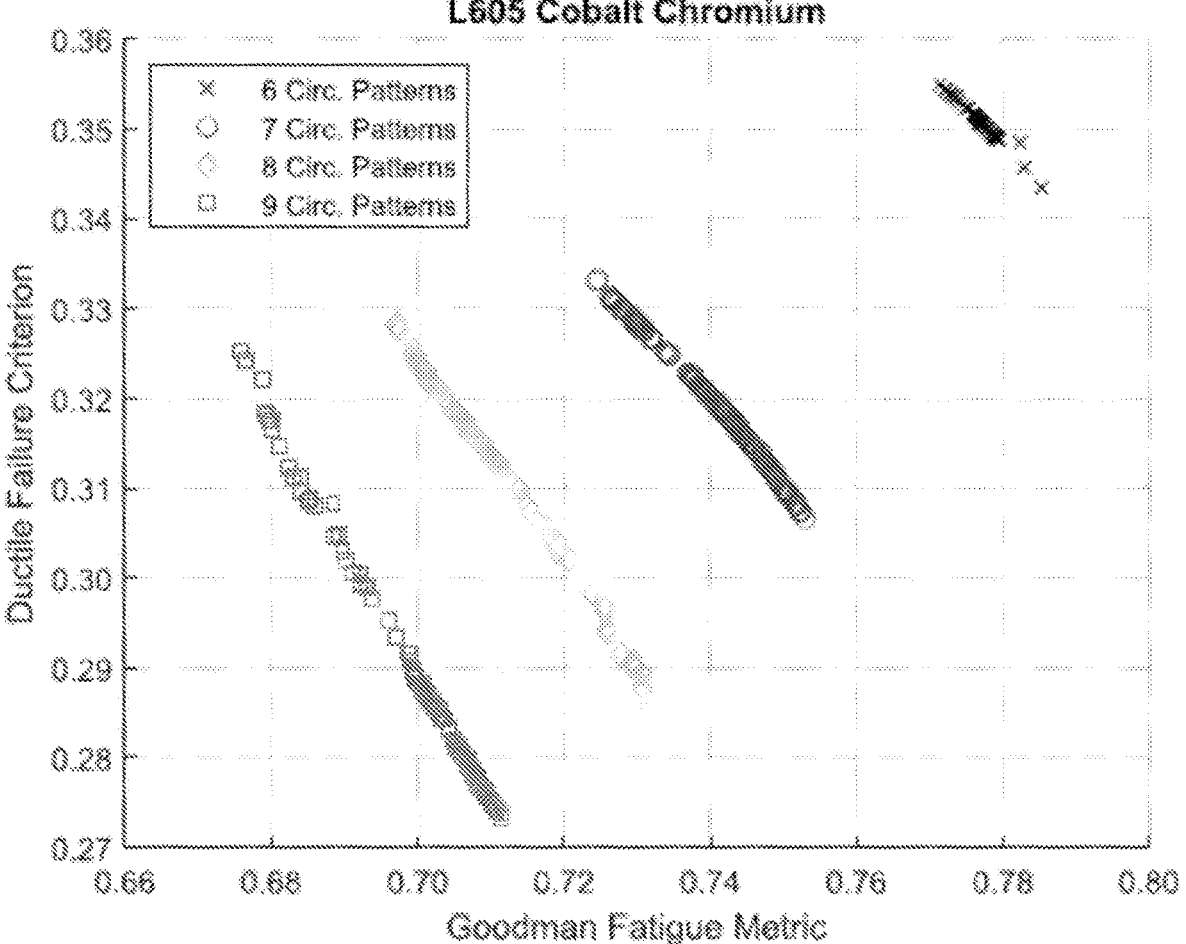
FIG. 46B illustrates pareto-optimal points illustrating the trade-off between GF and DF for L605 stent material for a number of circumferential patterns, NCP.
Figure 47A:
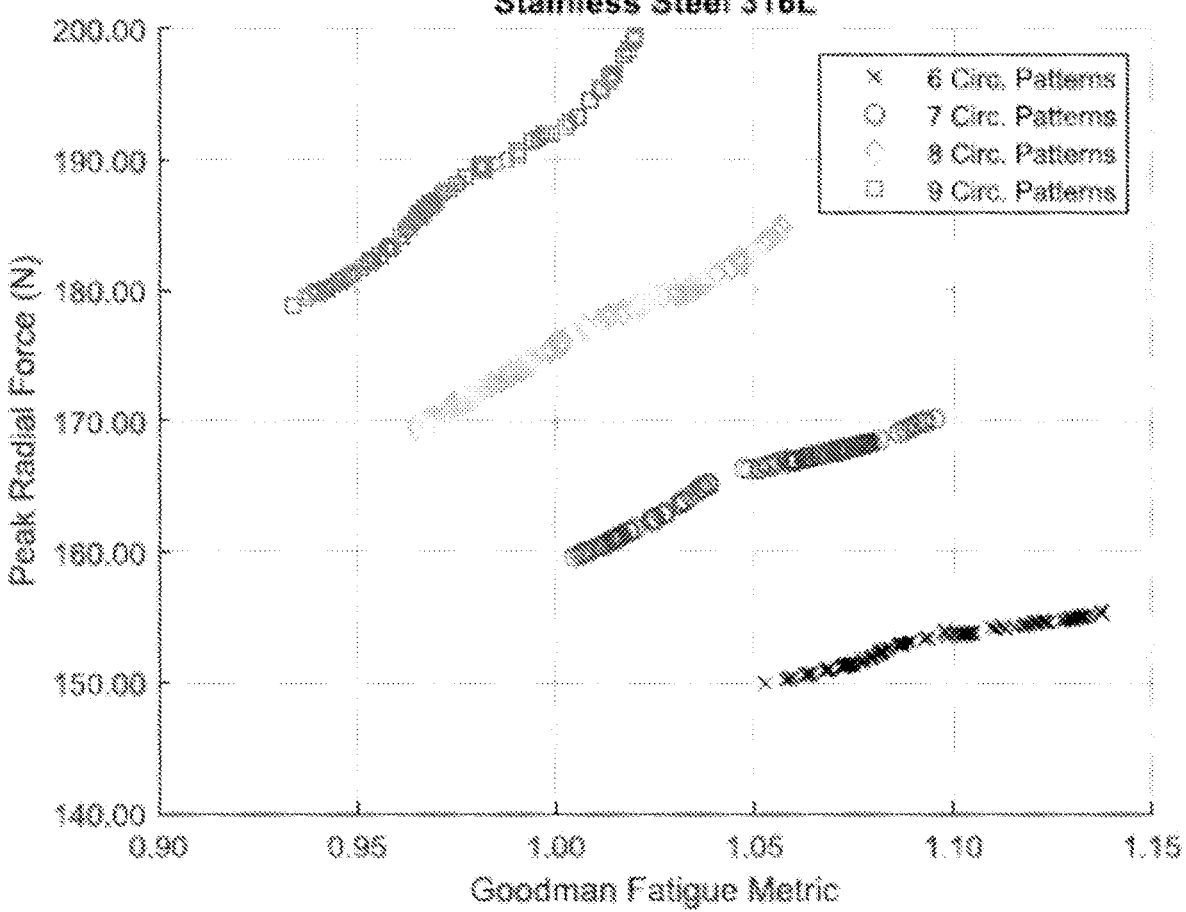
FIG. 47A illustrates pareto-optimal points illustrating the trade-off between GF and RF for 316L stent material for a number of circumferential patterns, NCP.
Figure 47B:
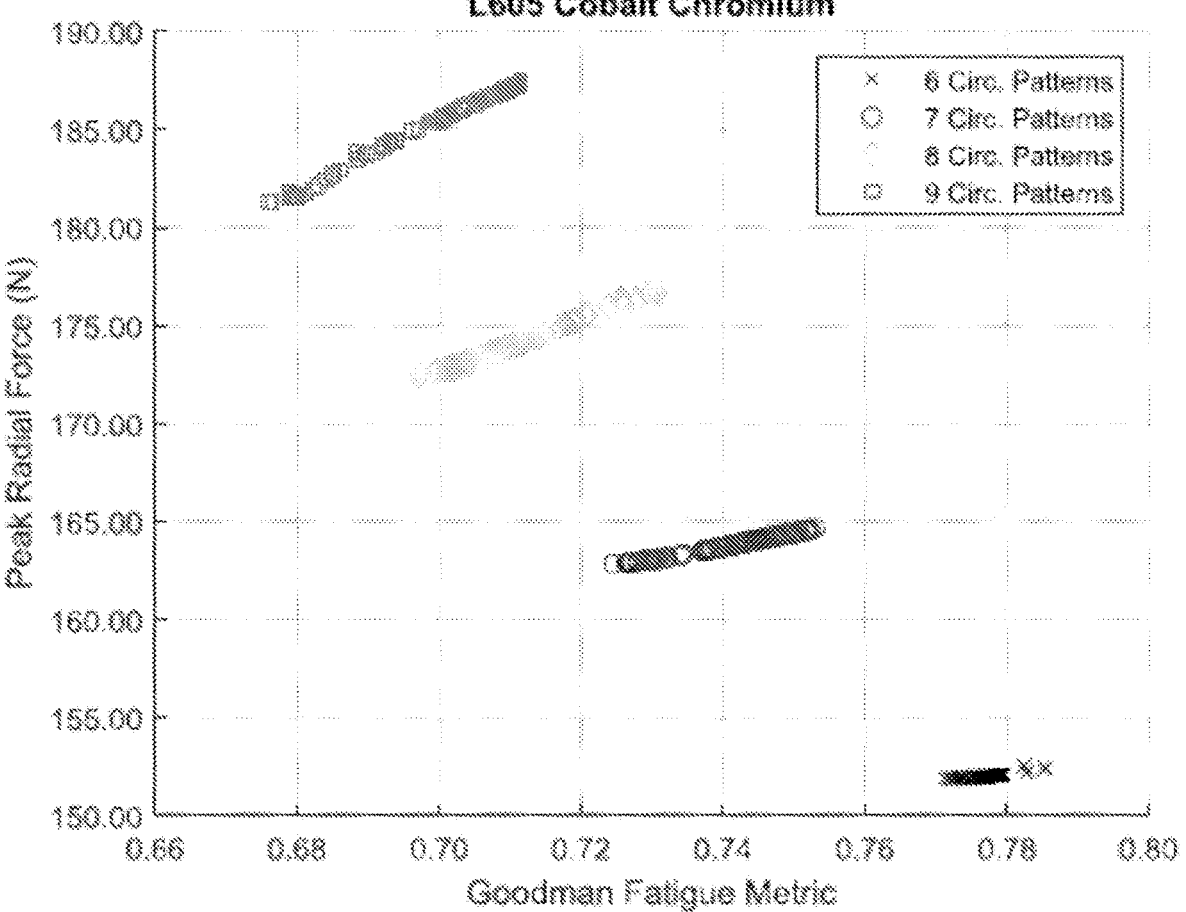
FIG. 47B illustrates pareto-optimal points illustrating the trade-off between GF and RF for L605 stent material for a number of circumferential patterns, NCP.
Figure 48A:
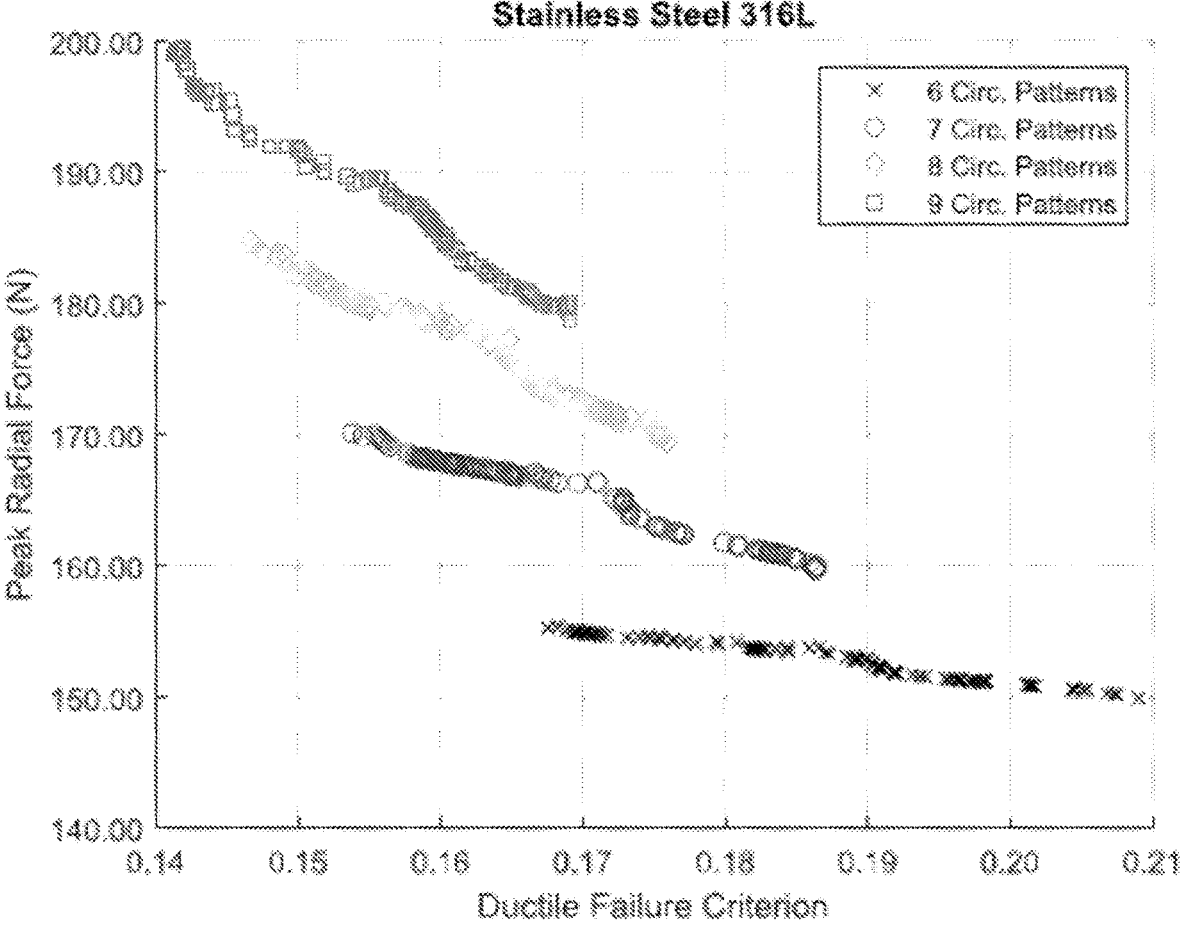
FIG. 48A illustrates pareto-optimal points illustrating the trade-off between DF and RF for 316L stent material for a number of circumferential patterns, NCP.
Figure 48B:
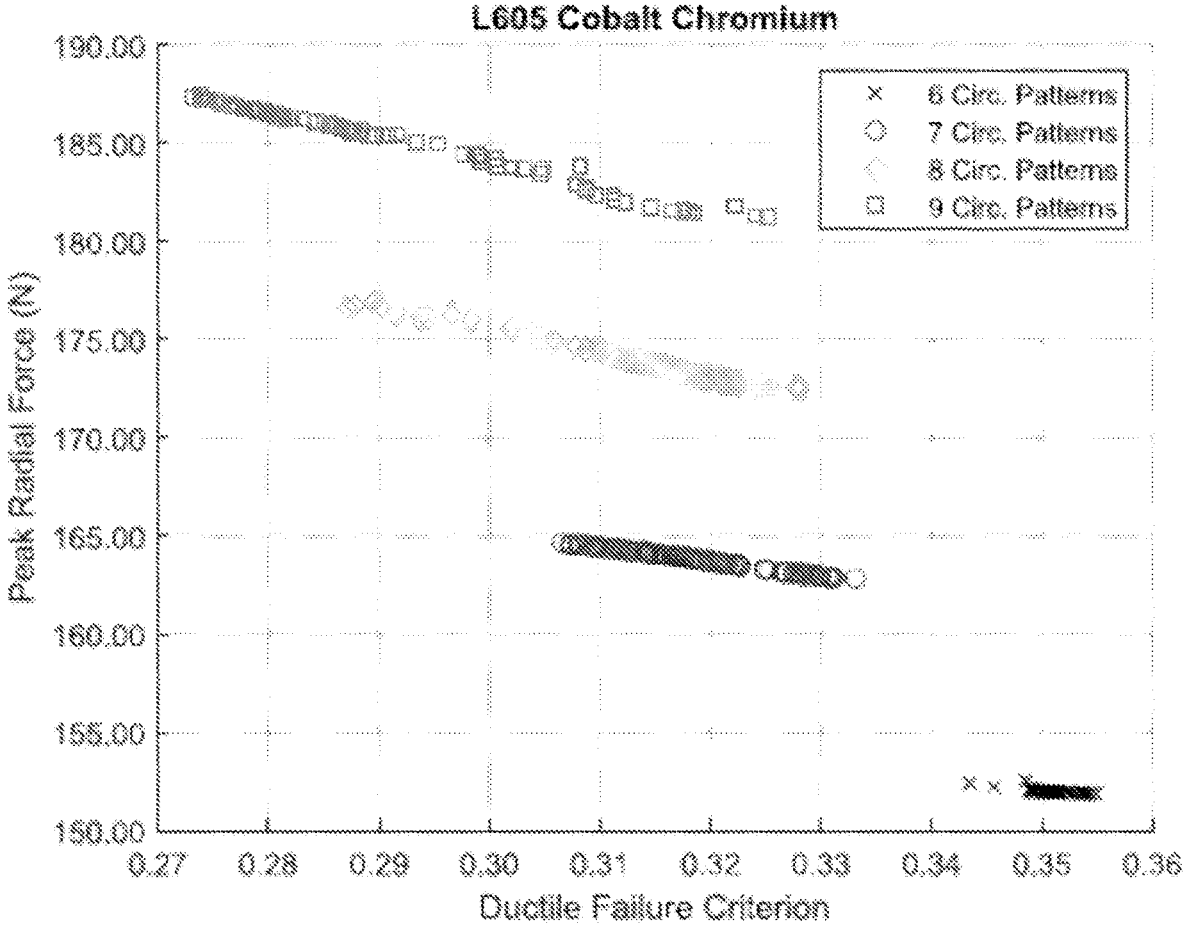
FIG. 48B illustrates pareto-optimal points illustrating the trade-off between DF and RF for L605 stent material for a number of circumferential patterns, NCP.
Figure 49A:
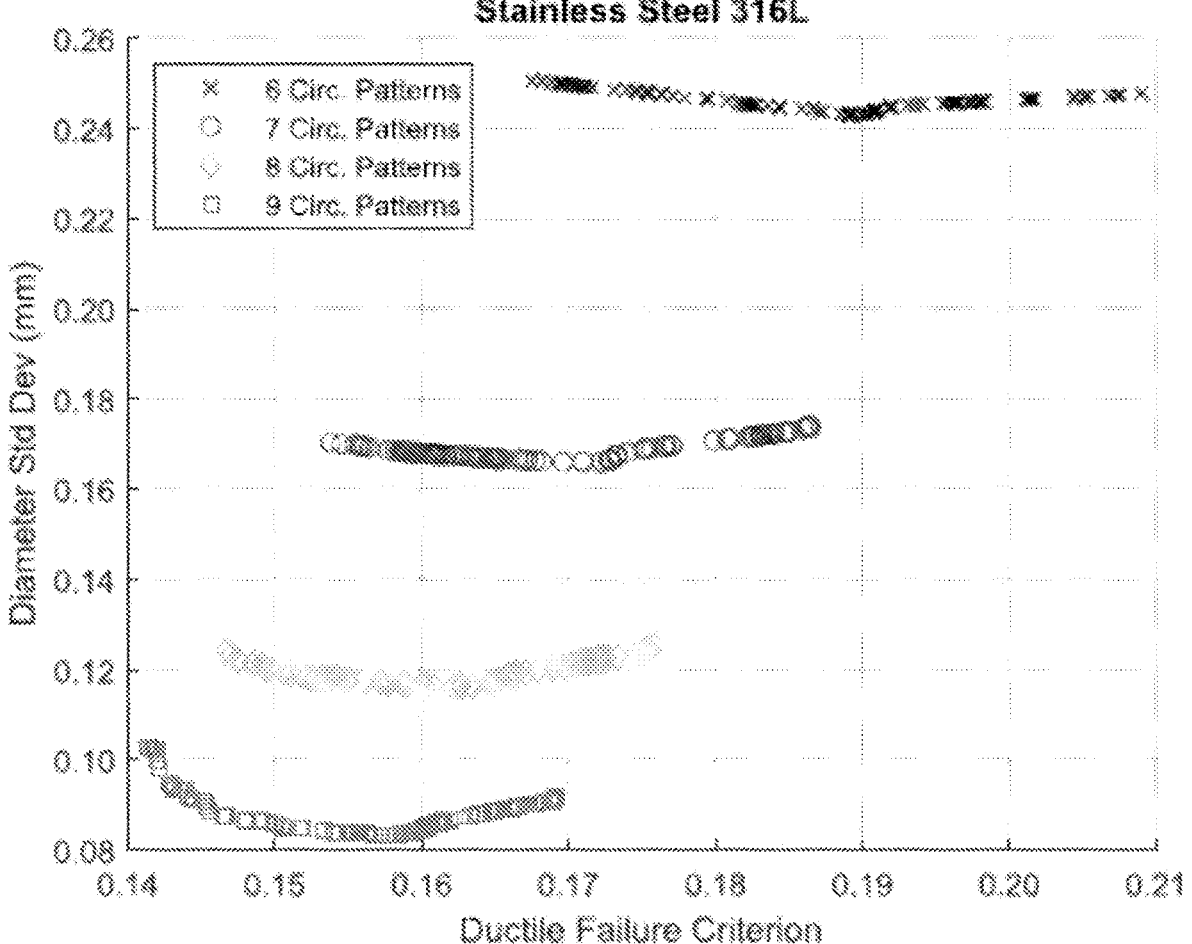
FIG. 49A illustrates pareto-optimal points illustrating the trade-off between DF and $D_{stddev}$ for 316L stent material for a number of circumferential patterns, NCP.
Figure 49B:
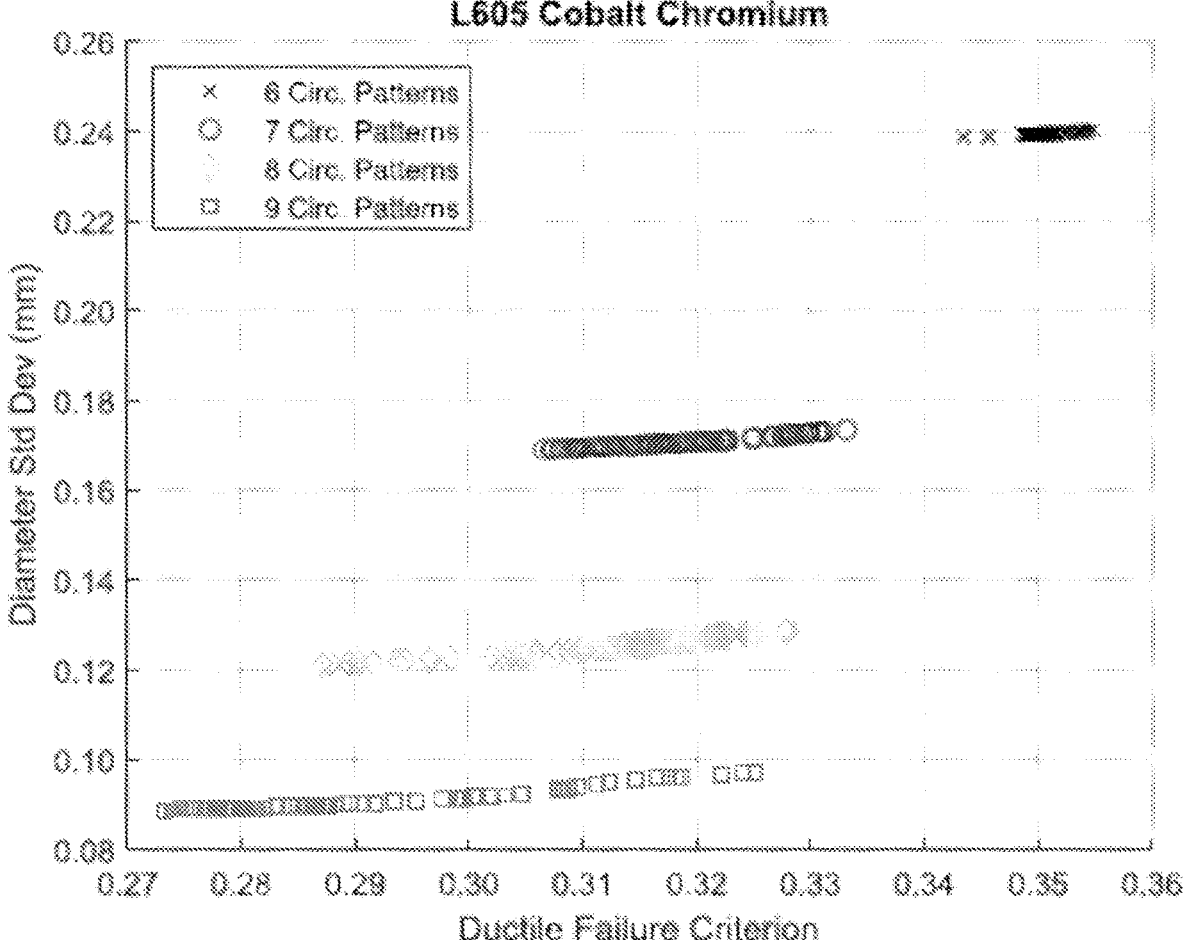
FIG. 49B illustrates pareto-optimal points illustrating the trade-off between DF and $D_{stddev}$ for L605 stent material for a number of circumferential patterns, NCP.
Figure 50A:
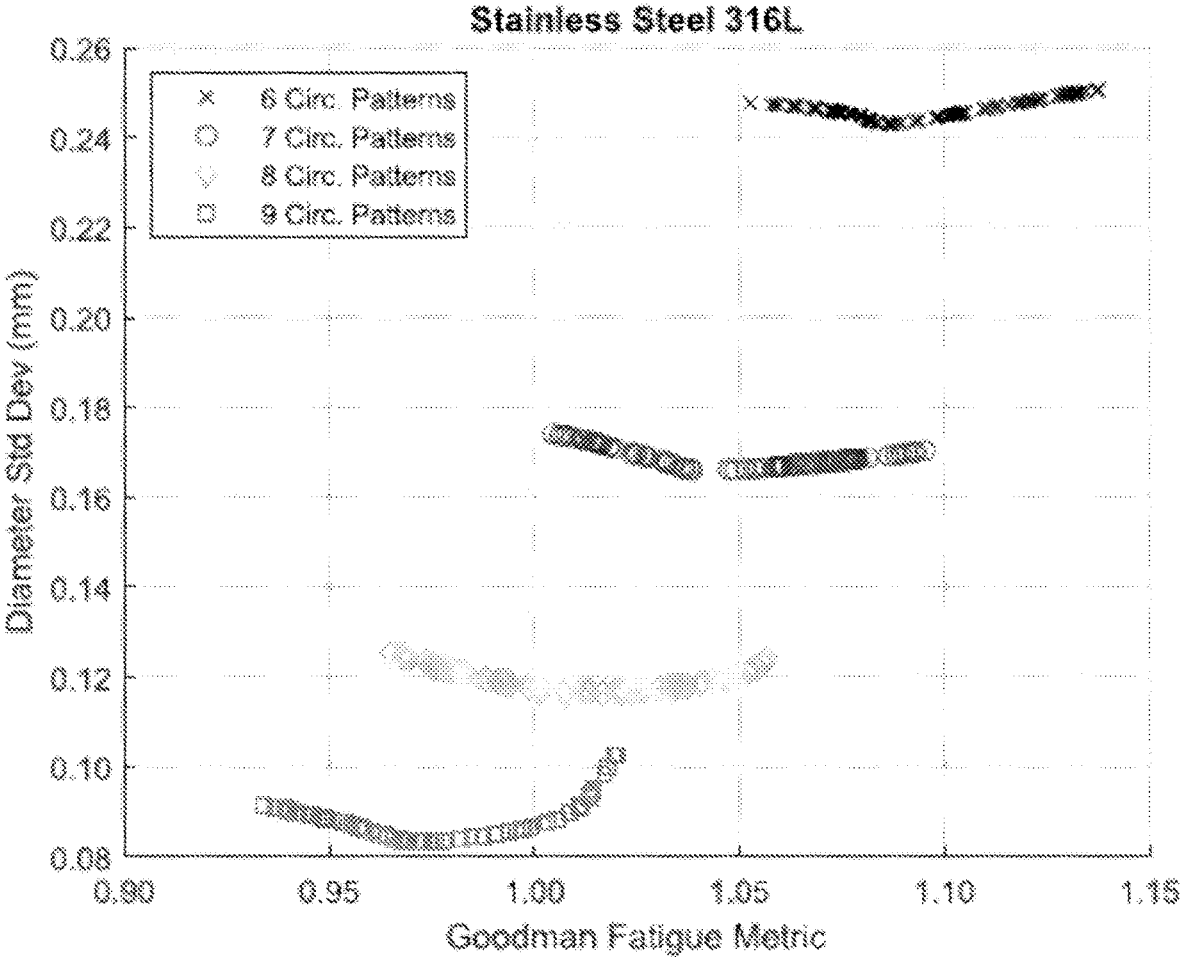
FIG. 50A illustrates pareto-optimal points illustrating the trade-off between GF and $D_{stddev}$ for 316L stent material for a number of circumferential patterns, NCP.
Figure 50B:
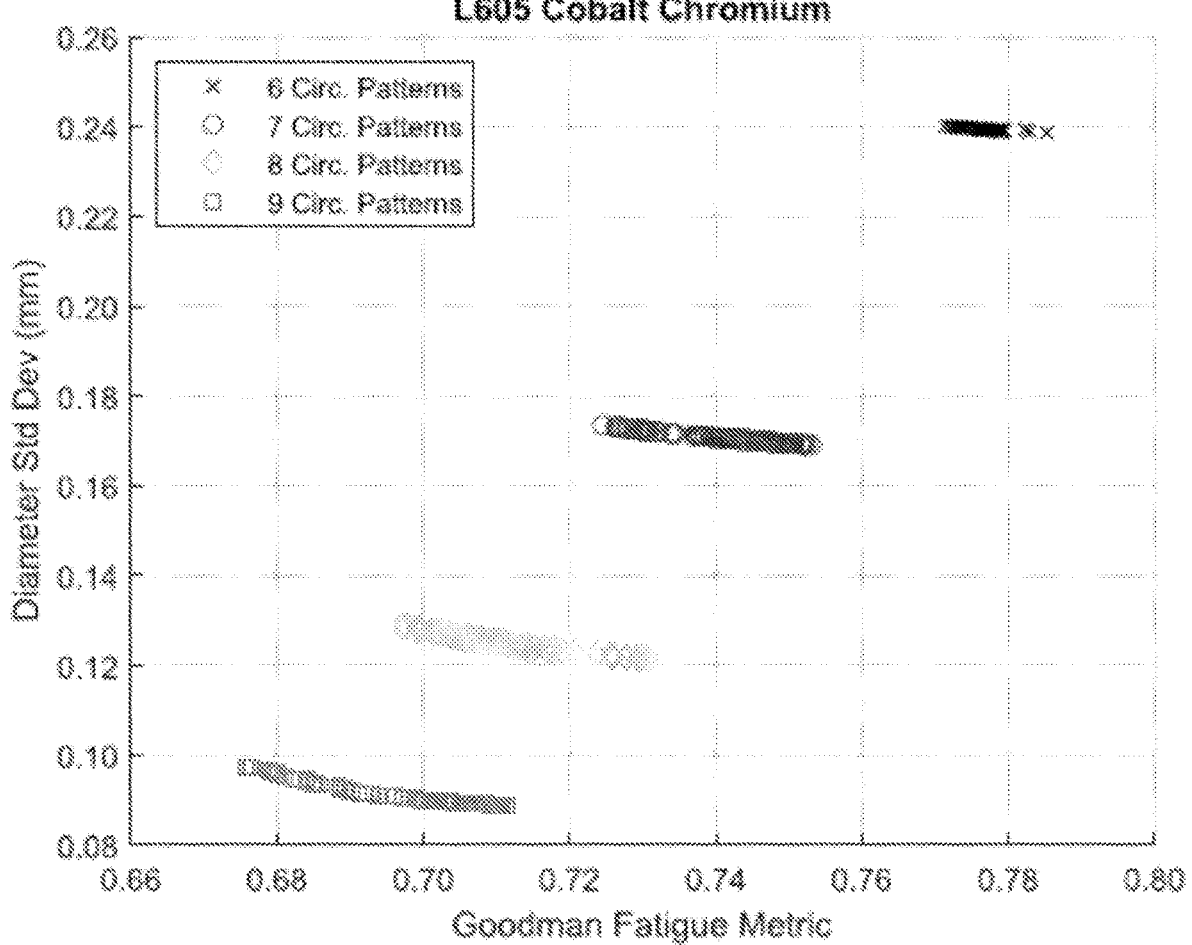
FIG. 50B illustrates pareto-optimal points illustrating the trade-off between GF and $D_{stddev}$ for L605 stent material for a number of circumferential patterns, NCP.
Figure 51A:
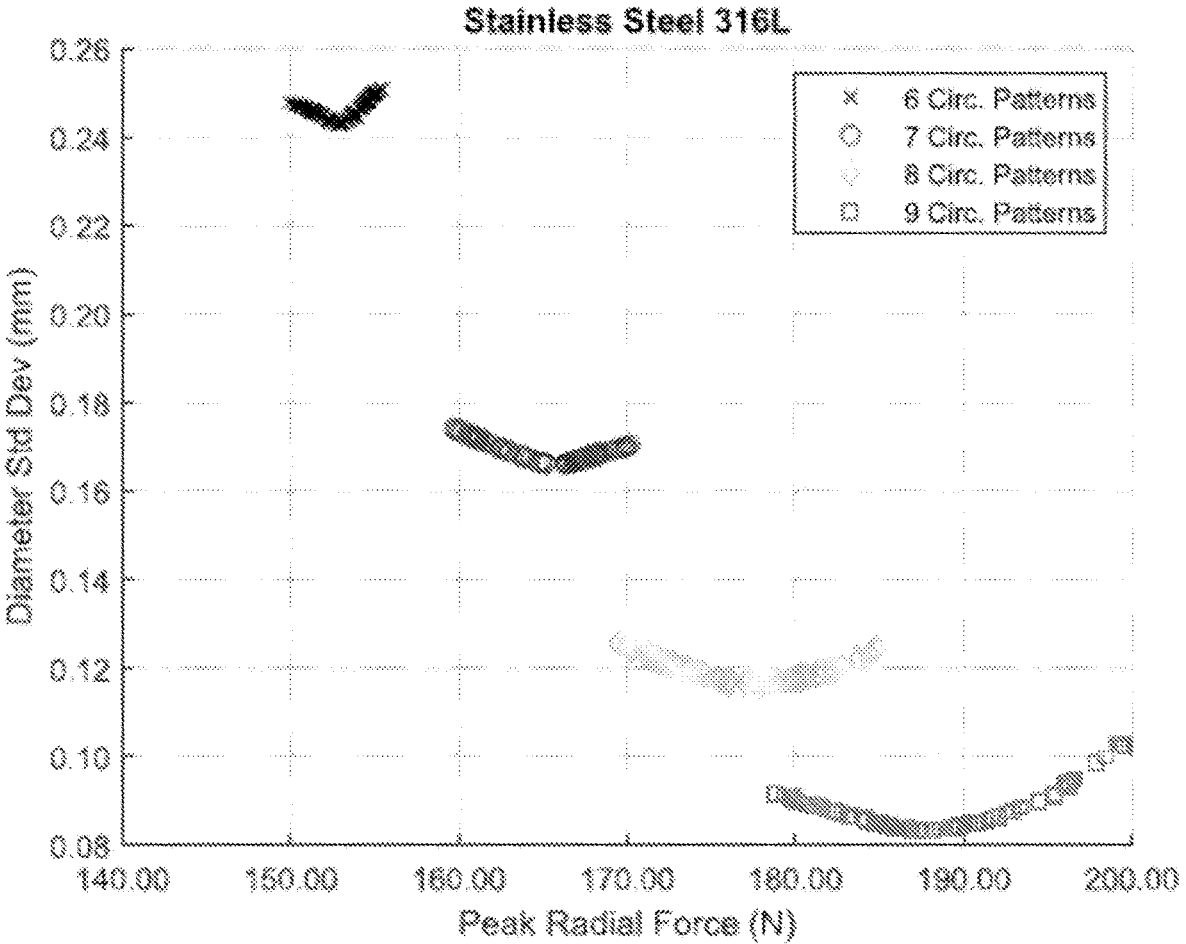
FIG. 51A illustrates pareto-optimal points illustrating the trade-off between RF and $D_{stddev}$ for 316L stent material for a number of circumferential patterns, NCP.
Figure 51B:
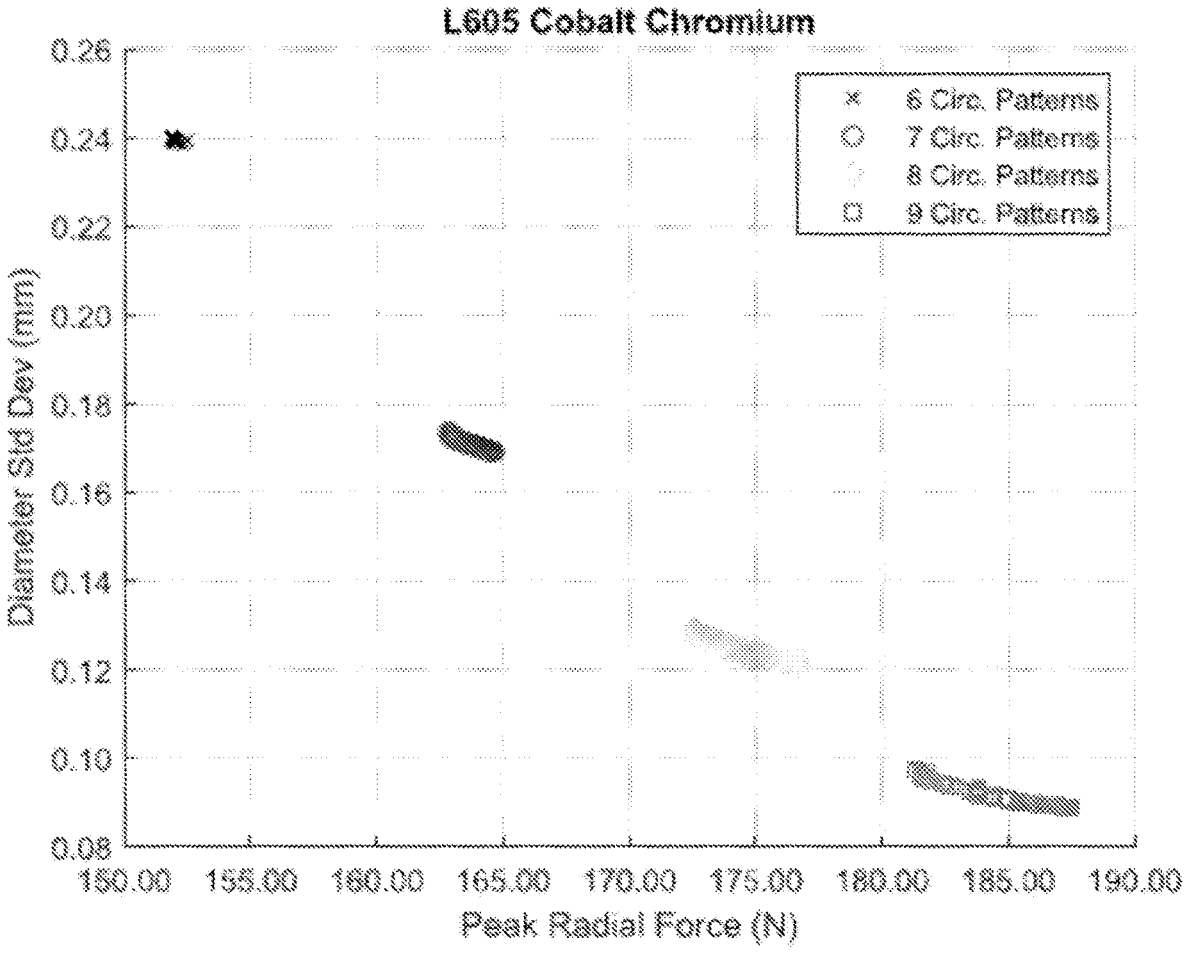
FIG. 51B illustrates pareto-optimal points illustrating the trade-off between RF and $D_{stddev}$ for L605 stent material for a number of circumferential patterns, NCP.

Two dimensional trade-off plots for every unique combination of the 4 objective functions (6 in total) are provided in FIGS. 46A-51B. FIGS. 46A-46B illustrate the conflicting trade-off between ductile failure resistance during expansion and the subsequent resistance to fatigue failure. Although larger values of the normalized ductile failure criterion are predicted for the L605 stent, the values are still quite low (again, a value greater than 1 would represent a ductile failure prediction). However, subsequent future expansions may result in ductile failure for the L605 material, while 316L might generally be safer. This highlights the difficulty of the design problem since 316L may be better for large diameter expansions, but it also might be subject to higher risk of fatigue failure. Additionally, with the exception of the peak radial force (RF), increasing the number of circumferential patterns (NCP) is beneficial. The peak radial force clearly increases more rapidly with increasing strut width (W) as opposed to strut thickness (T) as expected, but the values for fixed W and T do not seem to vary greatly with the number of circumferential patterns (NCP). The opposite effect is observed for the standard deviation of the permanent diameter ($D_{stddev}$), which appears to be overwhelmingly most sensitive to NCP.

Plots of the normalized aggregate objective function in Equation (4) are provided in FIGS. 52A-52F along with the Pareto-optimal points and the result of solving the single objective optimization problem. Pareto-optimal points are illustrated with black x markers. The optimal point 0 of Equation (4) is marked by a diamond. Equation (4) is solved using the gradient-based "function" optimizer with an initial guess equal to the Pareto-optimal point which produced the lowest normalized aggregate objective function value. The CAD geometry corresponding to the best performing design for both 316L and L605 was created and a high fidelity numerical analysis was completed for each. Table 2 provides the values of the relevant surrogate functions at the corresponding optimized parameter set for each material and NCP. W* and T* refer to the optimized values of Wand T, respectively, and "A.Obj." signifies the value of the aggregate objective function in Equation (4) evaluated with the corresponding optimized parameters. The L605 material allows generally thinner stent struts to be used. The optimized geometric design parameters obtained for 316L are (0.46 mm W, 0.8 mm T, 9 NCP) and (0.5 mm W, 0.4 mm T, 9 NCP) for L605.

TABLE 2

| Material | NCP | W* | T* | GF | DF | RF(N) | $D_{stddev}$ (mm) | A Obj |
|----------|-----|------|------|-------|-------|-------|-------|------|
| 316L | 6 | 0.48. | 0.55 | 1.080 | 0.191 | 152 | 0.244 | 1.65 |
| 316L | 7 | 0.47 | 0.63 | 1.030 | 0.176 | 163 | 0.169 | 1.26 |
| 316L | 8 | 0.44 | 0.80 | 0.965 | 0.176 | 169 | 0.125 | 1.01 |
| 316L | 9 | 0.46 | 0.80 | 0.934 | 0.169 | 179 | 0.092 | 0.83 |
| L605 | 6 | 0.42 | 0.40 | 0.785 | 0.343 | 152 | 0.239 | 1.43 |
| L605 | 7 | 0.45 | 0.40 | 0.753 | 0.307 | 165 | 0.169 | 1.06 |
| L605 | 8 | 0.48 | 0.40 | 0.731 | 0.287 | 177 | 0.121 | 0.83 |
| L605 | 9 | 0.50 | 0.40 | 0.711 | 0.273 | 187 | 0.089 | 0.67 |

Figure 52A:
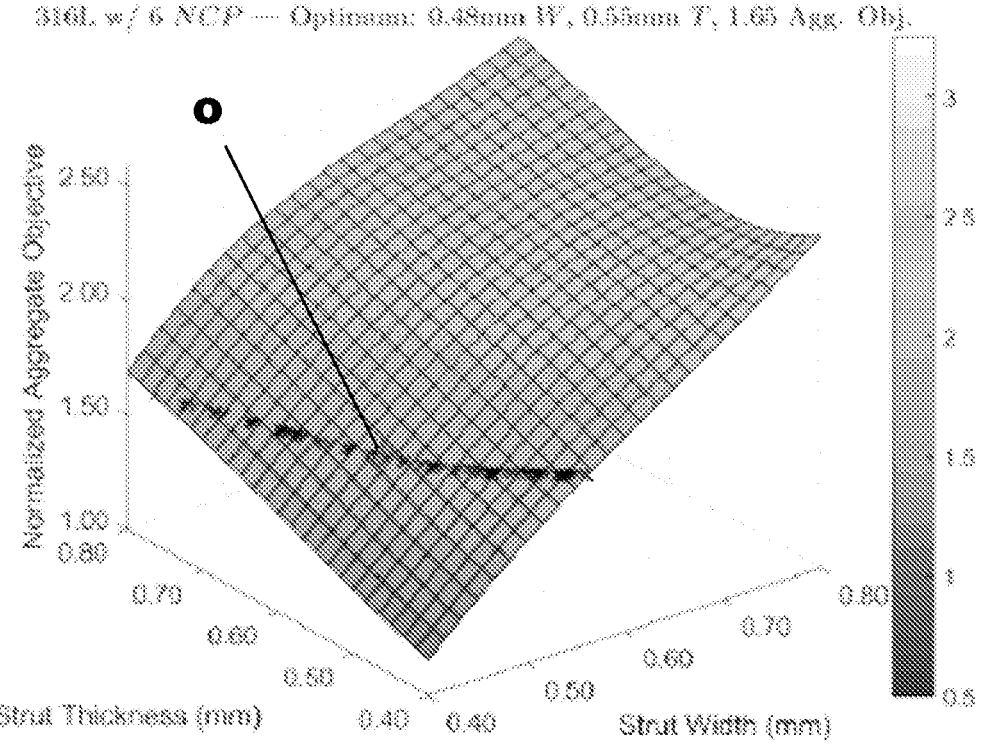
FIGS. 52A-52B illustrate the aggregate objective function surfaces for each NCP=6 for 316L and L605 stent material, illustrating the optimal point of Equation (4).
Figure 52B:
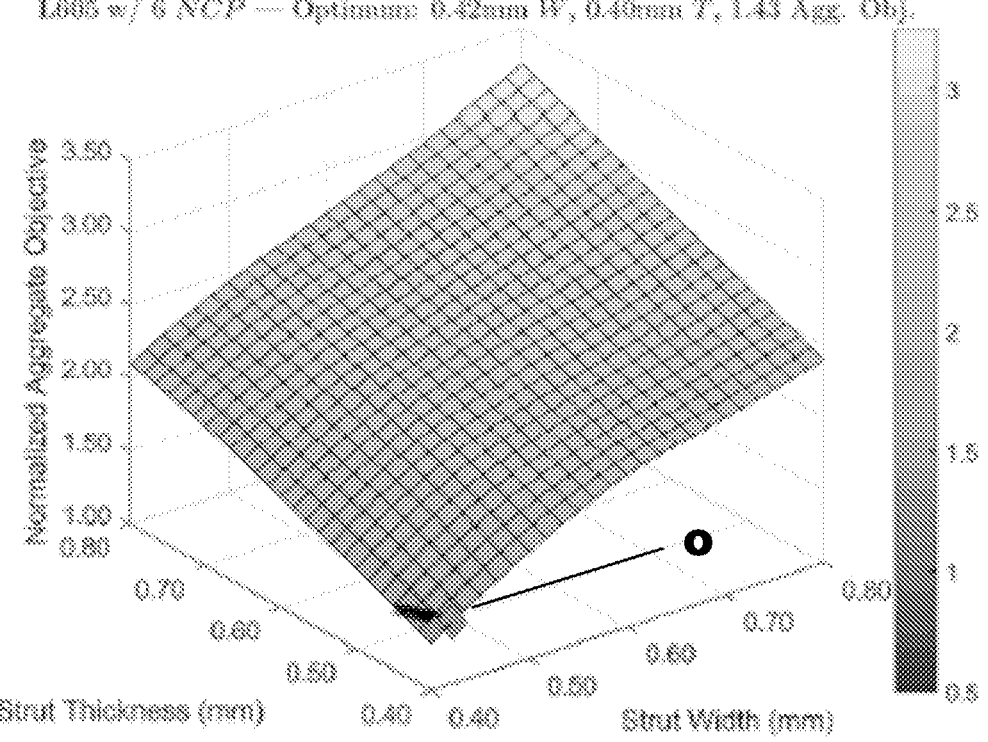
Figure 52C:
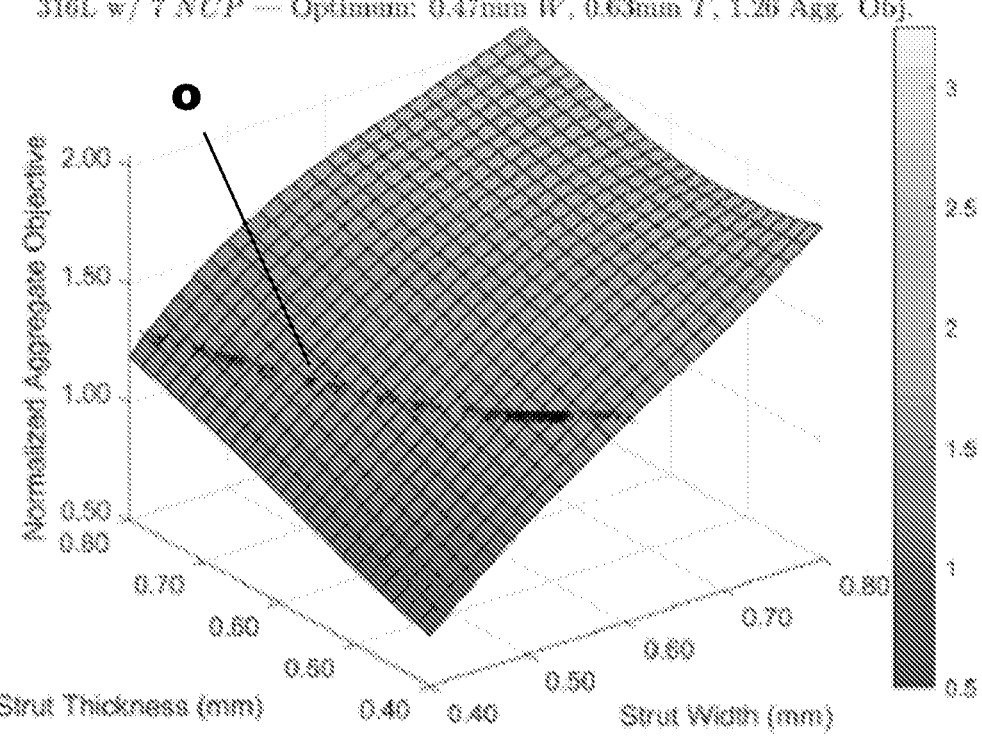
FIGS. 52C-52D illustrate the aggregate objective function surfaces for each NCP=7 for 316L and L605 stent material, illustrating the optimal point of Equation (4).
Figure 52D:
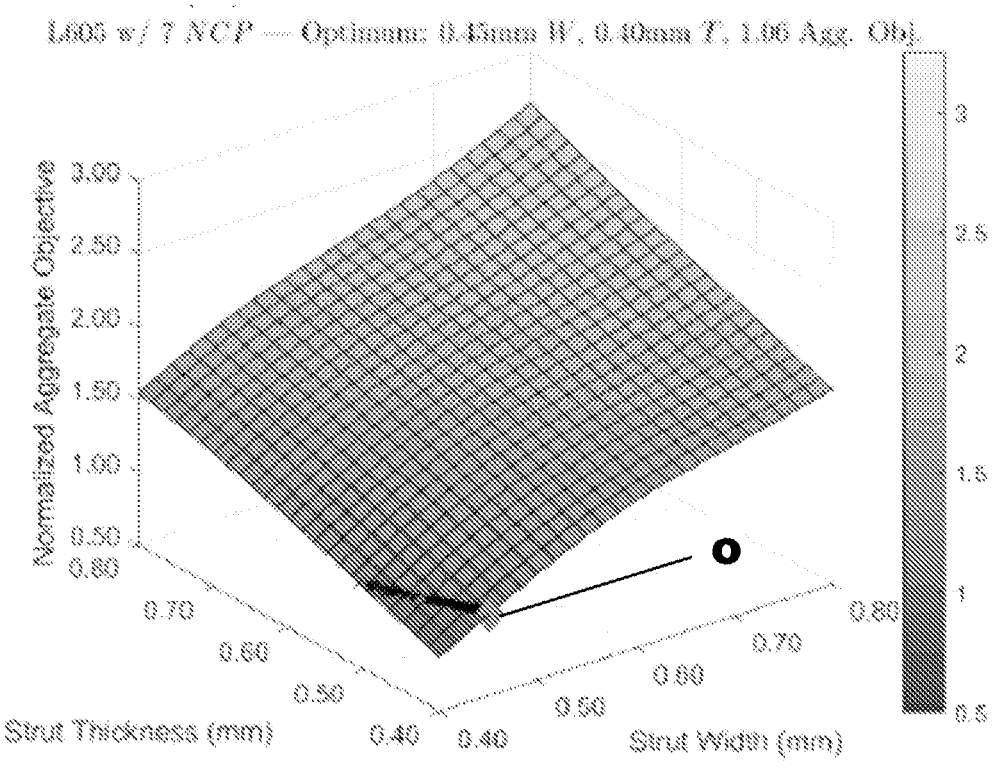
Figure 52E:
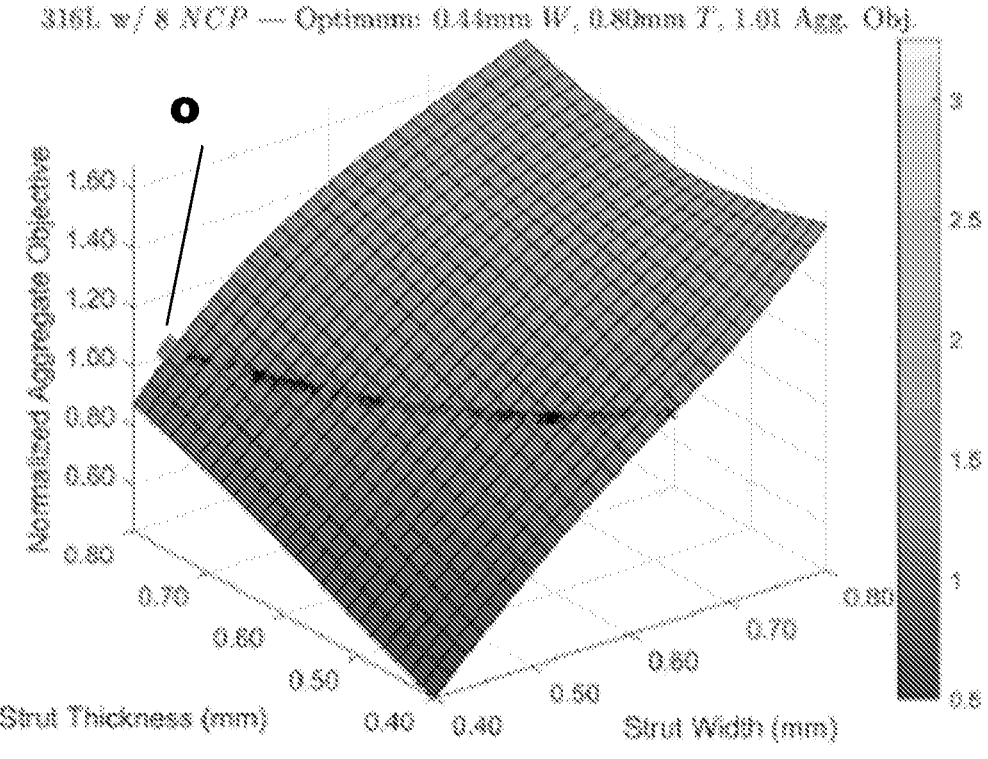
FIGS. 52E-52F illustrate the aggregate objective function surfaces for each NCP=8 for 316L and L605 stent material, illustrating the optimal point of Equation (4).
Figure 52F:
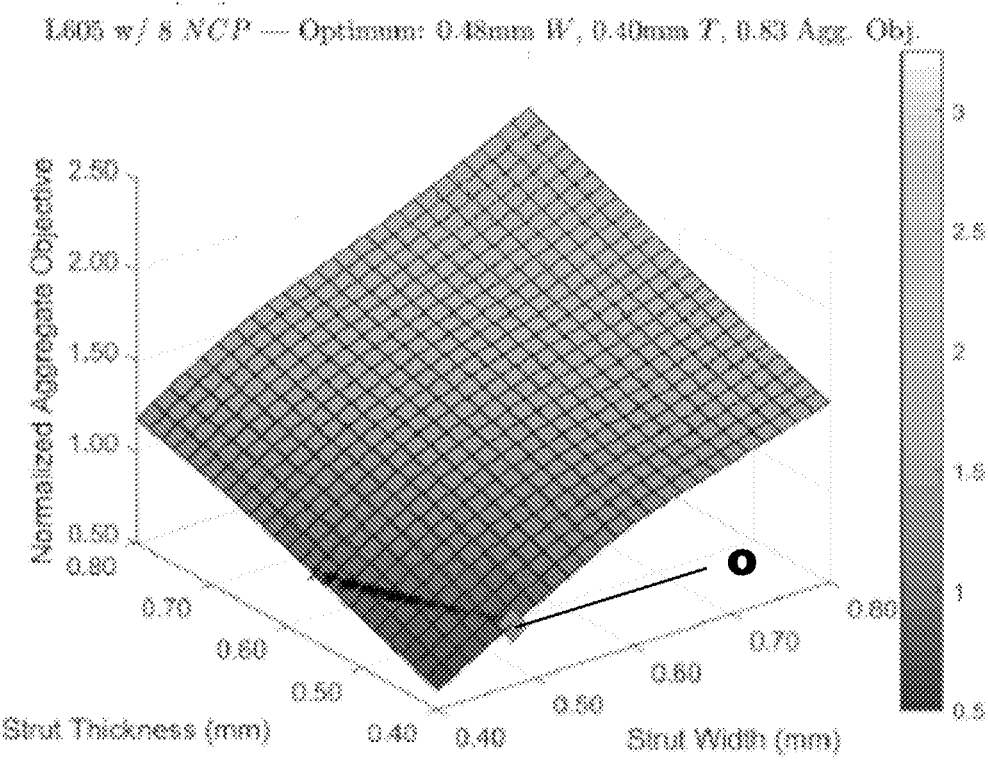
Figure 52G:
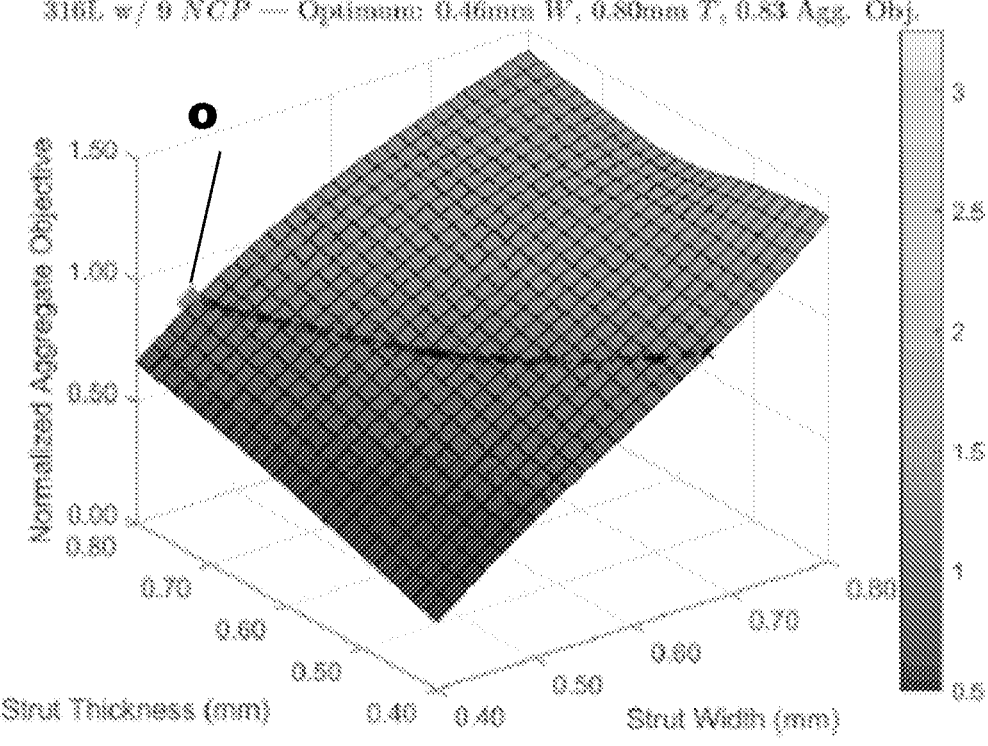
FIGS. 52G-52H illustrate the aggregate objective function surfaces for each NCP=9 for 316L and L605 stent material, illustrating the optimal point of Equation (4).
Figure 52H:
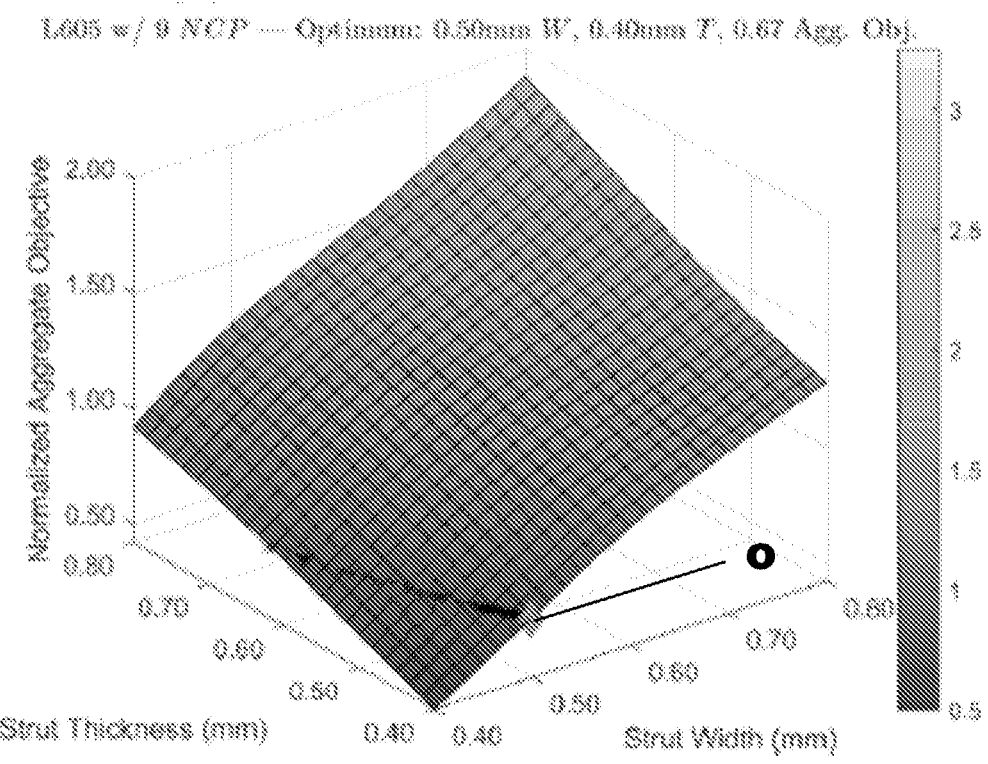
Figure 53B:
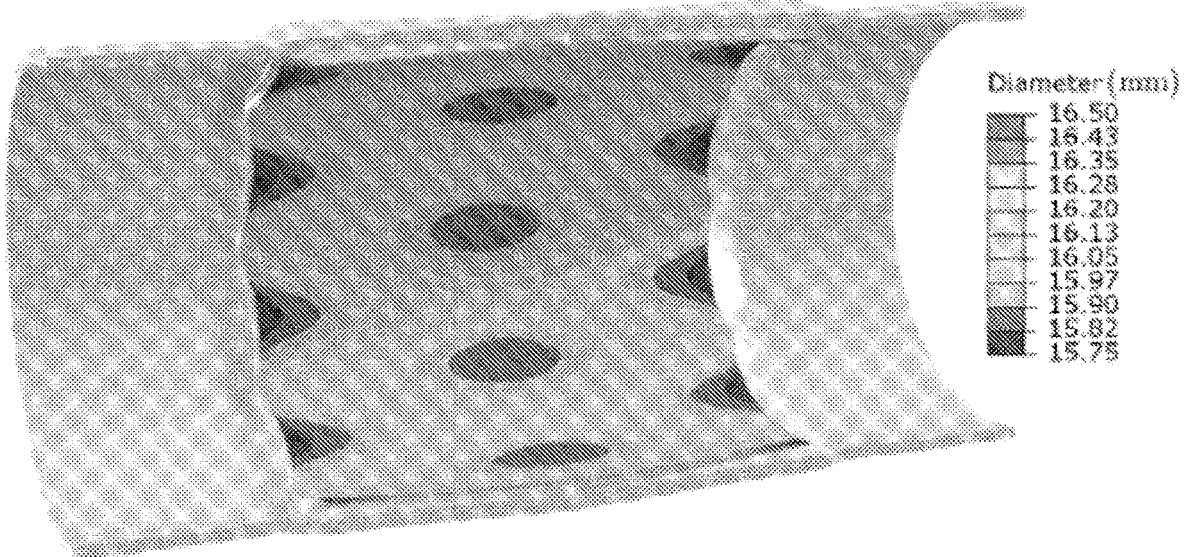
FIG. 53B is an isometric side cross-section of the stented region of L605 stent material illustrating the spatial variation of the permanent diameter in the stented region.
Figure 54A:
FIG. 54A illustrates the spatial variation of the normalized ductile failure criterion (DF) for 316L stent material.
Figure 54B:
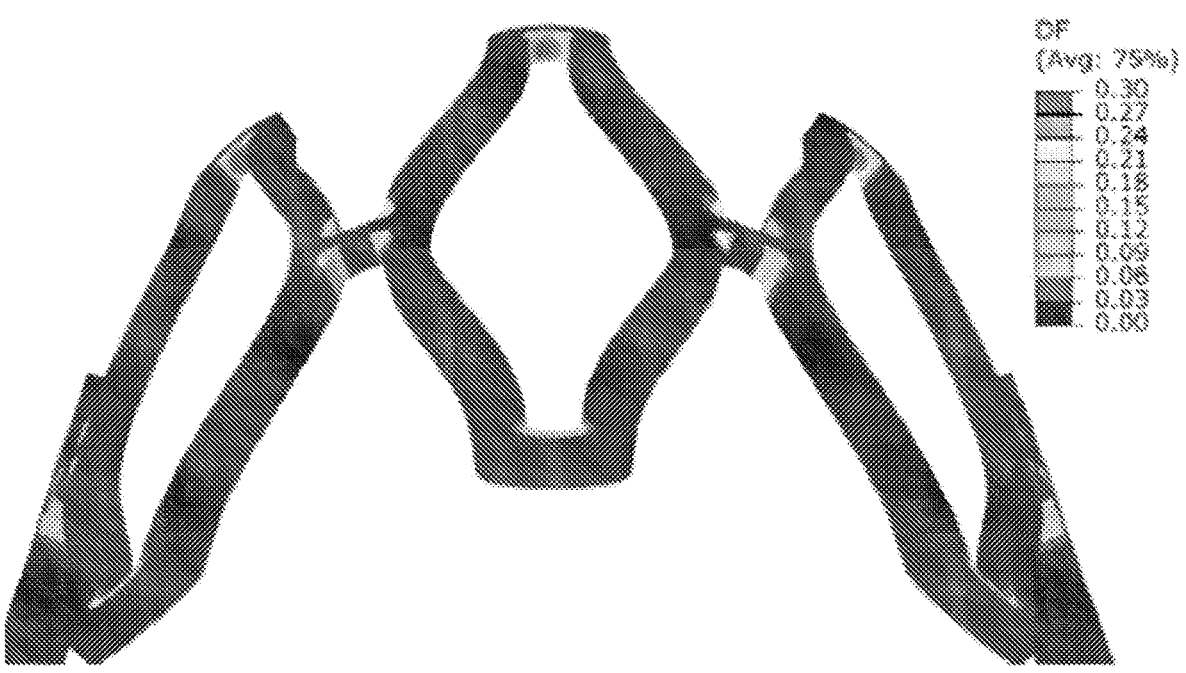
FIG. 54B illustrates the spatial variation of the normalized ductile failure criterion (DF) for L605 stent material.
Figure 55B:
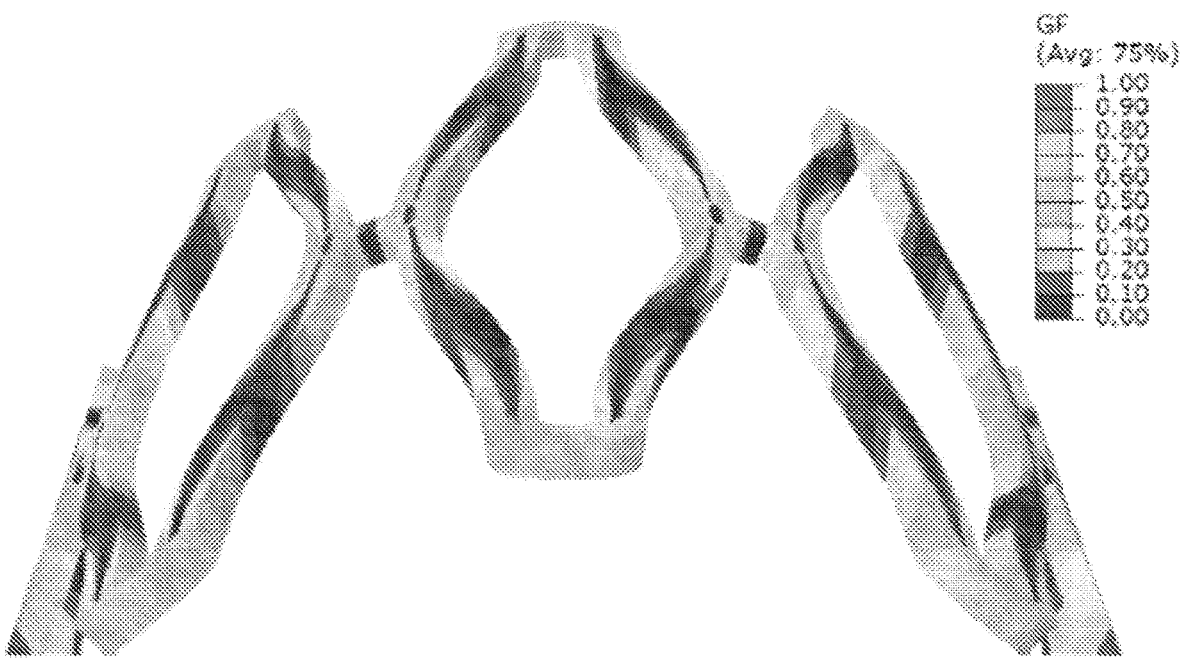
FIG. 55B illustrates the spatial variation of the Goodman Fatigue metric (GF) for L605 stent material.

The spatial distribution of the permanent diameter in the stented region, the normalized ductile failure criterion, and the Goodman fatigue metric are also illustrated in FIGS. 53A-53B, 54A-54B and 55A-55B, respectively. The largest ductile failure and fatigue measures are concentrated on the inner radii of the stent members. One can conclude that the optimized L605 stent with aforementioned parameters is best suited to achieve the goal as stated mathematically in Equation (4). It also clear from FIG. 52H that the L605 material may allow for a better performing design with a stent strut thickness below the 0.4 mm lower bound assigned in this study. Assuming the L605 material does not suffer the size effect noted for 316L, or pending additional test data, it appears that further optimization with smaller strut thicknesses may be beneficial. Based on FIG. 52G, a similar observation is noted for 316L if strut thicknesses greater than 0.8 mm were allowed.

A multiobjective stent optimization procedure is proposed for the design of an expandable prosthetic valved-conduit with particular relevance to the pediatric population born with CHD. In addition to metrics associated with fatigue failure, a measure of ductile failure during expansion is also incorporated into the optimization procedure. It is demonstrated that the proposed procedure is capable of producing a stent design with relatively low required radial force that meets design durability criteria, and maintains sufficient radial stiffness to counteract the retractive forces of the polymeric glue layer used during construction. Pareto-optimal designs are obtained and illustrated using smooth cubic surrogate models and the relevant tradeoffs between design objectives are provided. Additionally, a single aggregate objective function is defined in which each of the original objective functions are normalized and equally weighted in order to provide a direct comparison of all designs and arrive at a single optimal result. This was possible due to the inherent relative importance assigned to each objective within the aggregate objective function and provides a useful comparison to other non-dominated Pareto-optimal designs.

Future studies of this type could be expanded and improved in a number of ways. These include calibration and use of a more accurate viscoplastic constitutive model for the e-PTFE material. Alternative polymeric glues should also be explored in addition to Carbothane™ which was selected for this study. Furthermore, tests for both 316L stainless steel and L605 cobalt chromium should be conducted with specimen dimensions in the range of those used for the stents considered in this work, especially since size-dependent properties might be observed as briefly discussed above. Verification of the nonlinear hardening curves, ductile failure criteria, and metrics associated with Goodman fatigue analysis would also significantly improve confidence in the numerical results. Finally, further refinements of the design space in regions where the Pareto frontier is predicted could be further explored with high-fidelity simulations in order to improve the surrogate models and potentially increase the performance of the final design.

APPENDIX A. CONSTITUTIVE MODEL CALIBRATION

Figure 56A:
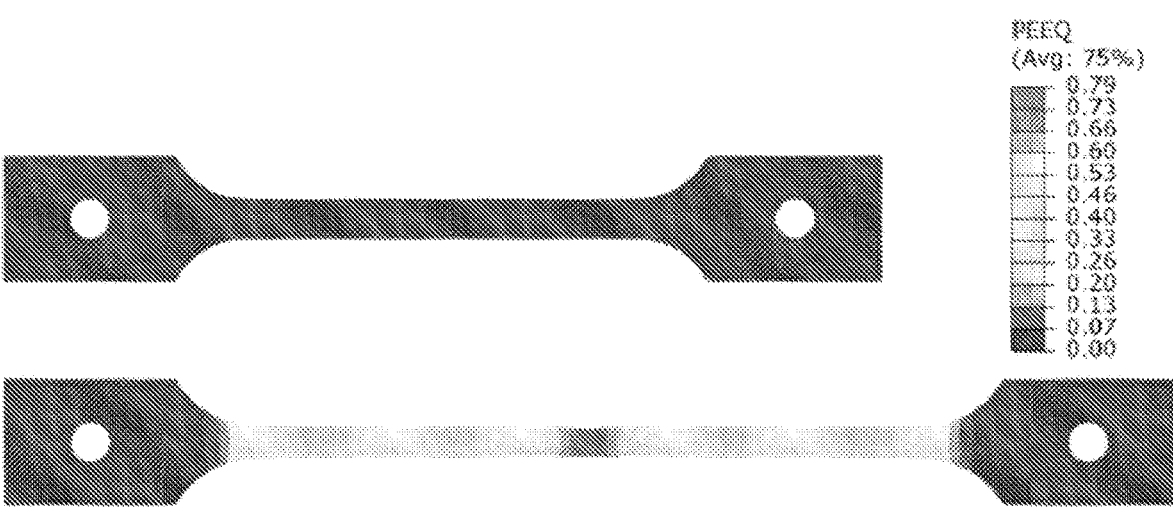
FIG. 56A illustrates the equivalent plastic strain field over the initial undeformed configuration (top) and deformed configuration (bottom) for 316L material.
Figure 56B:
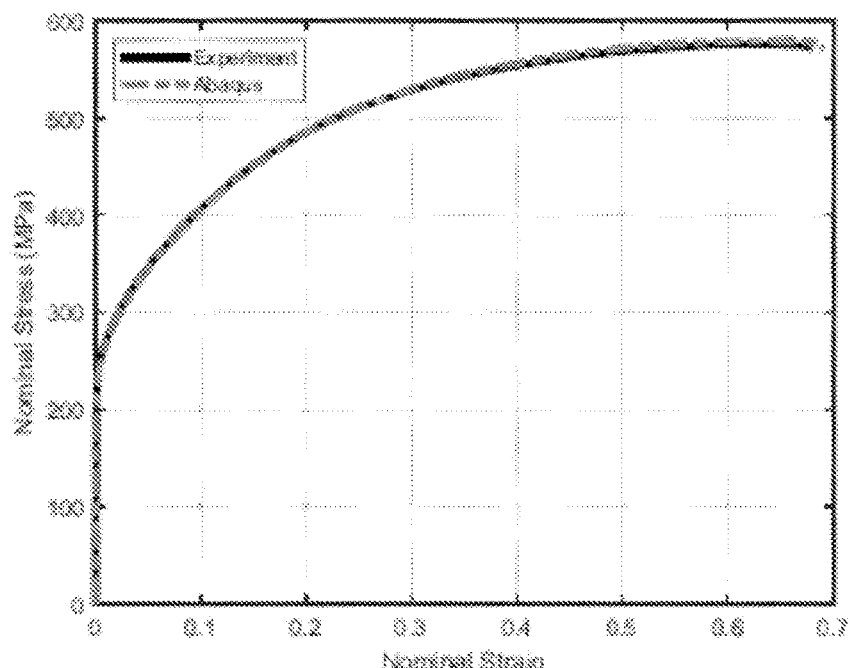
FIG. 56B illustrates the nominal stress versus strain curve comparison between the experimental and numerical prediction for 316L material.

Stainless Steel 316L. Uniaxial tension test data is used for calibration of a J2-plasticity model for 316L stainless steel. An elastic modulus of 193 GPa and Poisson's ratio of 0.27 is assumed and the nonlinear hardening curve is extracted from the test data and used to finely tune the macroscopic response up to the point of experimentally observed failure. The numerical geometry is exactly as reported in for the smooth bar without notches. Results from the calibration procedure are shown in FIGS. 56A-56B and a very good match between the nominal stress and strain data is observed. Numerical uniaxial test sequence used in the calibration to 316L stainless steel experimental data. Contours in FIG. 56A illustrate the equivalent plastic strain field over the initial undeformed configuration and the deformed configuration immediately preceding the experimentally determined failure point.

The critical value of the hydrostatic ductile failure criterion stated in Equation (6), where $$\epsilon_{p}^{f},$$

represents the equivalent plastic strain at failure, is then computed at the center of the specimen, using numerical integration of the computed stress triaxiality over the equivalent plastic strain history. A critical value, $DF_{crit}=0.269$, was obtained and is used herein for 316L stainless steel.

$$DF_{crit} = \int_{0}^{\epsilon_{p}^{f}} \frac{p}{\sigma vm} d \in p \tag{6}$$

Figure 57A:
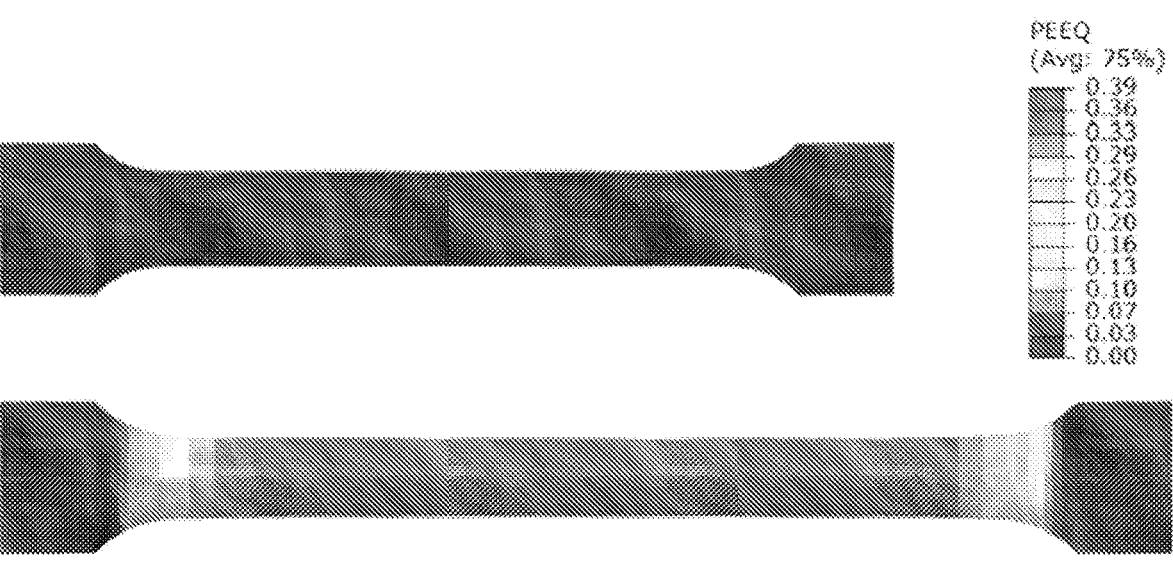
FIG. 57A illustrates the equivalent plastic strain field over the initial undeformed configuration (top) and deformed configuration (bottom) for L605 material.
Figure 57B:
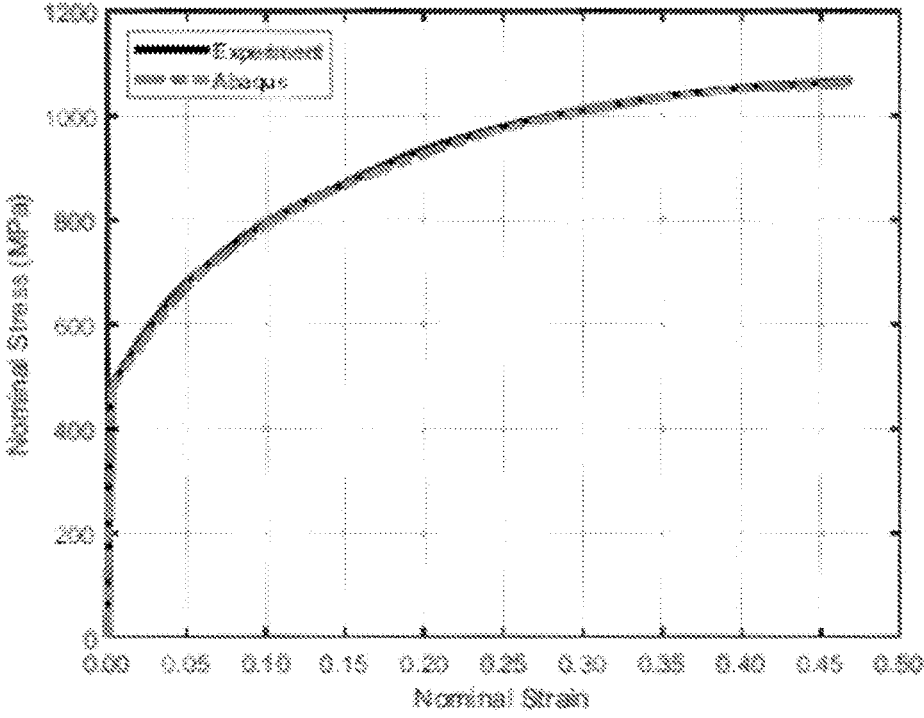
FIG. 57B illustrates the nominal stress versus strain curve comparison between the experimental and numerical prediction for L605 material.

L605 Cobalt Chromium. Similar to the constitutive model for 316L, J2-plasticity is also employed for L605. The model is calibrated using uniaxial tension test data. An elastic modulus of 196 GPa and Poisson's ratio of 0.29 are used while the nonlinear hardening curve is extracted from the experimental data and calibrated up until the point of experimentally observed failure. The numerical model employs a 5 mm diameter geometry with dimensions in accordance with the ASTM E8M standard. The results of the model calibration up to the point immediately preceding failure of the specimen are shown in FIGS. 57A-57B. Numerical uniaxial test sequence used in the calibration to L605 experimental data. Contours in FIG. 57A illustrate the equivalent plastic strain field over the initial undeformed configuration and the deformed configuration immediately preceding failure.

In a similar manner to the discussion in the previous subsection, the critical value of the hydrostatic ductile failure criterion is computed at the center of the specimen using numerical integration of the predicted stress triaxiality over the equivalent plastic strain history. A critical value, DFcrit=0.131, was obtained and is used in this work for the L605 material.

e-PTFE conduit material. While the actual mechanical constitutive behavior of e-PTFE is extraordinarily complex, the mechanical response is approximated using a built-in material model in Abaqus intended for modeling the permanent set that is observed in some elastomers and thermoplastics. The constitutive model we select consists of an Ogden-type hyperelastic strain energy density with two series terms (shown in Equation (7)), and a multiplicative split of the deformation gradient into elastic and plastic parts (i.e. $F=F^{e}F^{p}$).

$$U(F^{e}) = \sum_{i=1}^{2} \frac{2\mu_{i}}{\alpha_{i}^{2}} (\lambda_{1}^{\alpha i} + \lambda_{2}^{\alpha i} + \lambda_{3}^{\alpha i} - 3) + \sum_{i=1}^{2} \frac{1}{D_{i}} (J - i) \tag{7}$$

In the above expression, $$\{\lambda_{1}^{\alpha i}\},$$

represent the elastic principal stretches and J=det F=det Fe represents the dilatation since the plastic deformation is assumed to be isochoric. The remainder of the variables are material parameters which are provided in TABLE 3 below.

TABLE 3

| $\mu_1$ [MPa] | $\alpha_1$ | $\mu_2$ [MPa] | $\alpha_2$ | $D_1$[1/MPa] | $D_2$[1/MPa] |
|---|---|---|---|---|---|
| $1.008(10^{-4})$ | 25.0 | 1.26312 | 3.18637 | 0.06419 | 0.00000 |

Eventually, a more complex viscoplastic material model should be employed in order to better approximate the mechanical response of e-PTFE, such as one of those outlined. Samples of e-PTFE were obtained from International Polymer Engineering Inc., Tempe, Arizona. Subsequent mechanical tests were performed in air at ambient temperature (approximately 25° C.) using an Instron MicroTester 5848 (Instron, Norwood, Massachusetts), and all measurements were taken from distinct samples. Sample nominal strain was measured using the machine crosshead displacement. Rectangular strips (1×4 cm and 0.605 mm thick) with a 15 mm gauge length between the machine grips were uniaxially stretched to a single predetermined strain at a strain rate of $$0.0067 \frac{1}{s}.$$

Figure 58A:
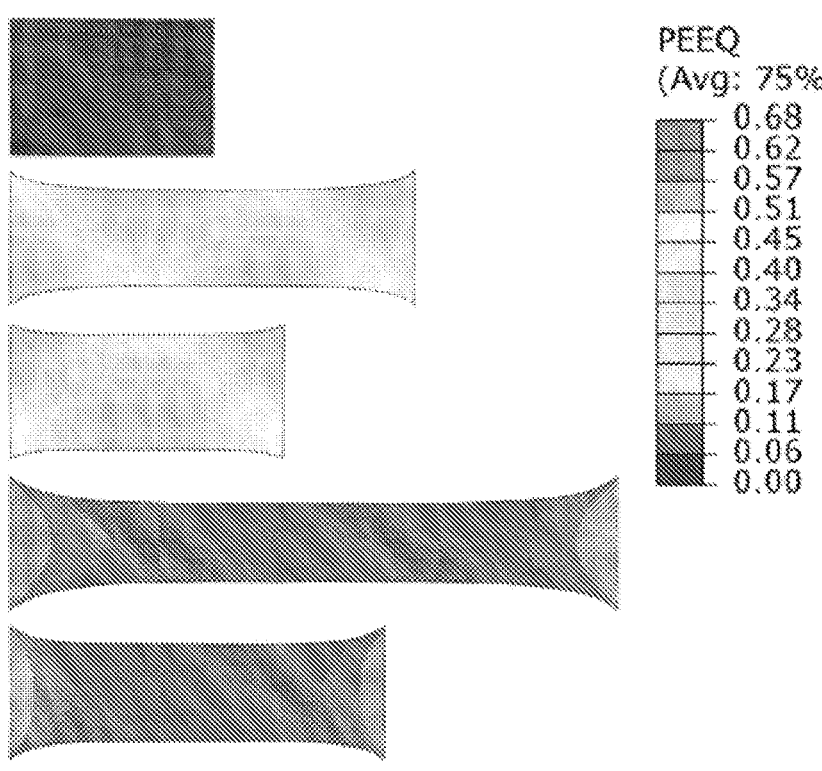
FIG. 58A illustrates the equivalent plastic strain field over the deformation sequence for e-PTFE material.
Figure 58B:
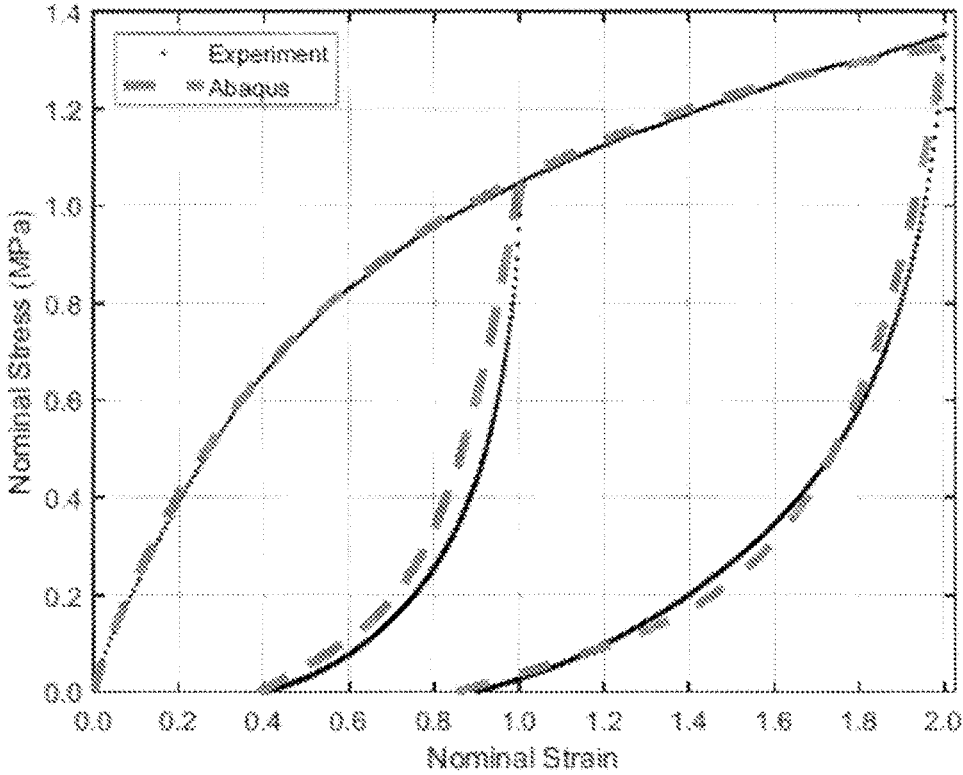
FIG. 58B illustrates the nominal stress versus strain curve comparison between the experimental and numerical prediction for e-PTFE material.

The samples were then immediately unloaded, and the grips were returned to the 15 mm gauge length at the same rate. The amount of immediately recoverable deformation was denoted by the point of return to zero stress. The sample was then removed from the machine grips and allowed to recover viscoelastically. Prior to the start of the test, the gauge length between the grip edges was also marked with a marker. After removal from the testing machine, the amount of strain in the sample was tracked by measuring the distance between these marks. The permanent set (i.e. final nominal strain) was measured 24 hours after the end of the unloading step. The calibration results for two cycles of uniaxial tension to different levels of peak strain and subsequent unloading to the permanent plastically deformed state, including an approximate Mullin's damage model, are shown in FIGS. 58A-58B. Numerical uniaxial test sequence used for material model calibration to e-PTFE experimental data. Contours in FIG. 58A illustrate the equivalent plastic strain field over each configuration in the deformation sequence. Additionally, the elastoplastic hardening curve is given in TABLE 4 (e-PTFE multilinear elastoplastic hardening curve (yield stress, $\sigma_y$, vs. equivalent plastic strain)) and the parameters associated with the Ogden-Roxburgh Mullins damage model are shown in TABLE 5 (e-PTFE Mullin's damage model parameters).

TABLE 4

| $\epsilon_p$ | $\sigma_y$ [MPa] |
|---|---|
| 0.0000 | 0.0507 |
| 0.3365 | 2.1000 |
| 0.6419 | 4.0554 |
| 6.4185 | 41.0480 |

TABLE 5

| F | m [N – mm] | 13 |
| --- | --- | --- |
| 1.223 | 0 | 0.785 |

Figure 59:
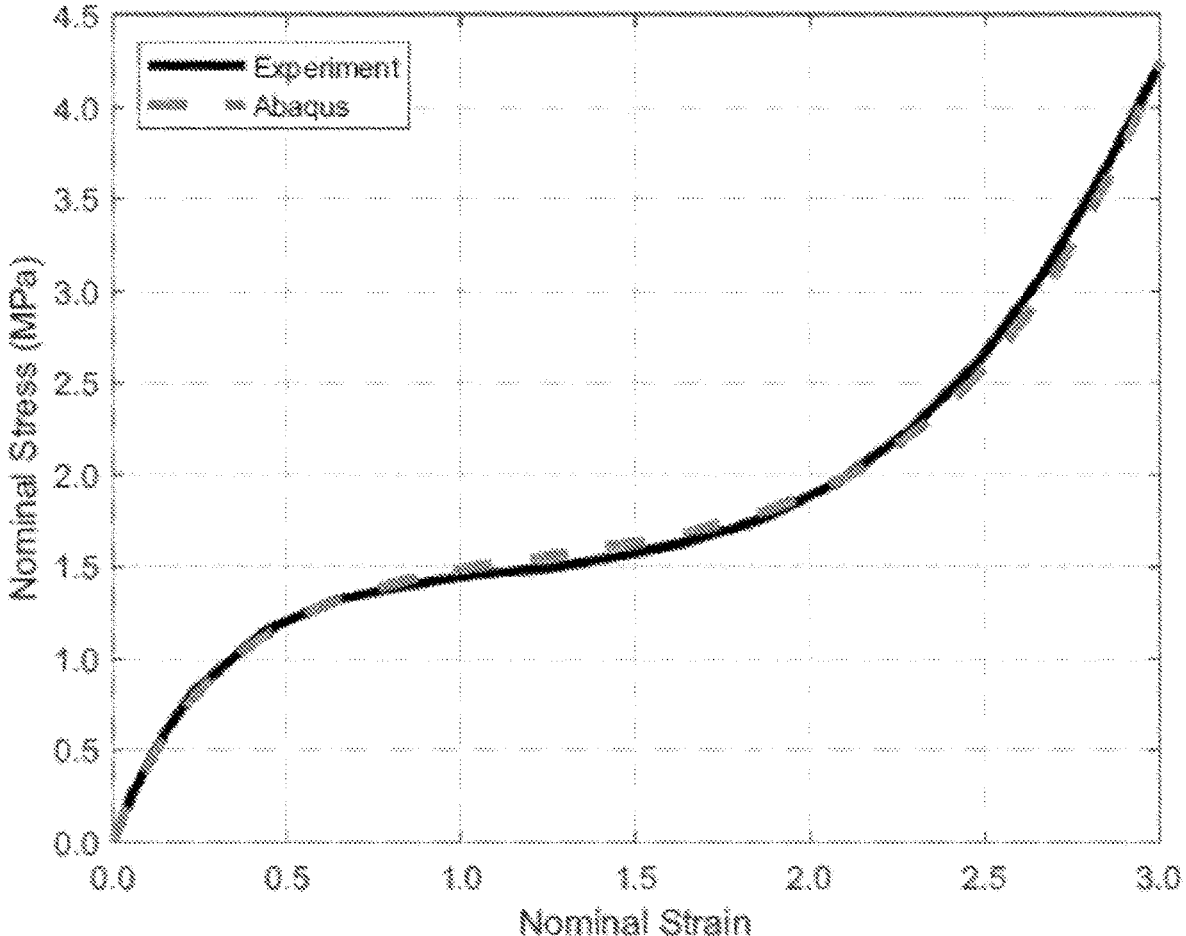
FIG. 59 illustrates the hyperelastic model calibration result for Carbothane.

Carbothane™ polymeric glue, Since the polymeric glue, Carbothane™, exhibits very little plastic deformation in the strain range of interest, we omit the elastoplastic physics and approximate the glue region mechanical response with an Ogden type hyperelastic model including two series terms (i.e. Equation A.2). A uniaxial tension experiment similar to that described in the previous subsection was conducted in order to calibrate this material model. To prepare the material samples, pellets of Carbothane™ AC-4075A were dissolved in N,N-Dimethylacetamide (DMAc, 99.5%, ACROS Organics, Fair Lawn, New Jersey) to create a viscous solution. After the dissipation of bubbles (approximately 24 hours), the polymer solution was cast onto a flat plate and then dried in an oven for 1 hour at 80° C. and ambient pressure. The resulting polymer film was cut into individual specimens for testing, and the thicknesses of the specimens were measured using a digital thickness gauge (Mitutoyo 547-526S, Mitutoyo Corporation, Tokyo, Japan). Material model calibration results are illustrated in FIG. 59 with corresponding parameters provided in Table 6 below. Note that the material is assumed to be incompressible.

TABLE 6

| $\mu_1$ [MPa] | $\alpha_1$ | $\mu_2$ [MPa] | $\alpha_2$ | $D_1$[l/MPa] | $D_2$[1/MPa] |
| --- | --- | --- | --- | --- | --- |
| 8.2(10–4) | 8.06 | 1.66 | –1.55 | 0.00 | 0.000 |

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Accordingly, nothing contained herein should be understood as limiting the scope of the disclosure. It is also understood that the terminology used herein is for the purpose of describing particular embodiments only, and is not intended to be limiting. Where a range of values is provided, it is understood that each intervening value between the upper and lower limit of that range and any other stated or intervening value in that stated range, is encompassed within the disclosed subject matter.

What is claimed is:

1. A transcatheter dilatable valve tube prosthesis comprising:
   a tubular member capable of plastic deformation from a first dimension to a second dimension;
   a valve component comprising a plurality of leaflets, the valve component capable of expansion from the first dimension to the second dimension, the valve component secured to an interior portion of the tubular member by an elastomeric glue at two circumferential portions defining an annular cavity therein, wherein the elastomeric glue is provided inside the annular cavity; and
   an expandable stent positioned in the annular cavity between the valve component and the tubular member and embedded in the elastomeric glue inside the annular cavity.

2. The transcatheter dilatable valve tube prosthesis of claim 1, wherein the tubular member is fabricated of expanded polytetrafluoroethylene (ePTFE).

3. The transcatheter dilatable valve tube prosthesis of claim 1 wherein the first dimension is a diameter of about 12 mm and the second dimension is a diameter of about 24 mm.

4. The transcatheter dilatable valve tube prosthesis of claim 1, wherein the plurality of leaflets define a height of coaptation, length of the leaflet free edge, shape of the leaflet free edge, and radial and circumferential curvatures of the leaflet, wherein one or more of the height of coaptation, length of the leaflet free edge, shape of the leaflet free edge, and radial and circumferential curvatures of the leaflet at the first dimension and the second dimension are sufficient to maintain of the integrity of the valve component.

5. The transcatheter dilatable valve tube prosthesis of claim 1, wherein the valve component comprises a sheet of ePTFE.

6. The transcatheter dilatable valve tube prosthesis of claim 1, wherein the expandable stent comprises one or more struts defining a strut width (W) and strut thickness (T) and a number of circumferential patterns (NCP), selected from a set of parameters (X) comprising strut width range, strut thickness range, number of circumferential patterns (NCP) range and stent material;
   wherein the strut width (W) and strut thickness (T) are determined by
      computing performance metrics comprising standard deviation of the descon dimension of the tubular conduit following plastic deformation (Dstddev), the peak radial force exerted by the stent to expand the tubular conduit (RF($\chi$), the Goodman metric for high cycle fatigue failure protection of the stent (GF($\chi$)) and the hydrostatic criterion for ductile failure prediction of the stent (DF($\chi$));
      constructing a surrogate model using the computed performance metrics to obtain a plurality of sets of Pareto-opitmal designs over all parameters ($\chi$); and
      identifying the strut width (W) and strut thickness (T) by optimizing a normalized aggregate objection function with equal weighing of performance metrics.

7. The transcatheter dilatable valve tube prosthesis of claim 6, wherein the strut width range is between 0.4 mm and 0.8 mm.

8. The transcatheter dilatable valve tube prosthesis of claim 6, wherein the strut thickness range is between 0.4 mm and 0.8 mm.

9. The transcatheter dilatable valve tube prosthesis of claim 6, wherein the number of circumferential patterns (NCP) range is between 6 and 9 patterns.

10. The transcatheter dilatable valve tube prosthesis of claim 6, wherein computing performance metrics comprises simulating the expansion of the stent by a balloon inserted in the stent.

11. The transcatheter dilatable valve tube prosthesis of claim 6, wherein constructing a surrogate model using the computed performance metrics to obtain a plurality of sets of Pareto-opitmal designs over all parameters ($\chi$) comprising minimizing the performance metrics over the parameters ($\chi$).

12. The transcatheter dilatable valve tube prosthesis of claim 1, wherein the valve component comprises a top terminal edge, a bottom terminal edge, and a middle portion extending between the top terminal edge and the bottom terminal edge, and the valve component is secured to the interior portion of the tubular member via the top terminal edge and via the bottom terminal edge, and the annular cavity is defined between the top terminal edge and the bottom terminal edge.

13. The transcatheter dilatable valve tube prosthesis of claim 1, wherein the transcatheter dilatable valve tube prosthesis in the first dimension is functional with valve competency and the transcatheter dilatable valve tube prosthesis in the second dimension is functional with valve competency.

14. A system for installation of a transcatheter dilatable valve tube prosthesis comprising:
  a transcatheter dilatable valve tube prosthesis comprising
    a tubular member capable of plastic deformation from a first dimension to a second dimension;
    a valve component comprising a plurality of leaflets, the valve component capable of expansion from the first dimension to the second dimension, the valve component secured to an interior portion of the tubular member by an elastomeric glue at two circumferential portions defining an annular cavity therein, wherein the elastomeric glue is provided inside the annular cavity; and
    an expandable stent positioned in the annular cavity between the valve component and the tubular member and embedded in the elastomeric glue inside the annular cavity; and
  a balloon catheter insertable into the transcatheter dilatable valve tube prosthesis to expand the tubular member and the valve component from the first dimension to the second dimension.

15. The system of claim 14 wherein the tubular member is fabricated of expanded polytetrafluoroethylene (ePTFE).

16. The system of claim 14 wherein the first dimension is a diameter of about 12 mm and the second dimension is a diameter of about 24 mm.

17. The system of claim 14, wherein the leaflets define a height of coaptation, length of the leaflet free edge, shape of the leaflet free edge, and radial and circumferential curvatures of the leaflet, wherein one or more of the height of coaptation, length of the leaflet free edge, shape of the leaflet free edge, and radial and circumferential curvatures of the leaflet at the first dimension and the second dimension are sufficient to maintain of the integrity of the valve component.

18. The system of claim 14, wherein the valve component comprises a sheet of ePTFE.

19. A method of installing a transcatheter dilatable valve tube prosthesis in the body conduit of a patient comprising:
  providing a transcatheter dilatable valve tube prosthesis comprising a tubular member capable of plastic deformation from a dimension to a second dimension; a valve component comprising a plurality of leaflets, the valve component capable of expansion from the first dimension to the second dimension, the valve component secured to an interior portion of the tubular member by an elastomeric glue at two circumferential portions defining an annular cavity therein, wherein the elastomeric glue is provided inside the annular cavity; and an expandable stent positioned in the annular cavity between the valve component and the tubular member and embedded in the elastomeric glue inside the annular cavity;
  inserting the transcatheter dilatable valve tube prosthesis into the body conduit of the patient;
  securing the transcatheter dilatable valve tube prosthesis;
  inserting a balloon catheter into the transcatheter dilatable valve tube prosthesis; and expanding the balloon catheter, thereby expanding the tubular member from the first dimension to the second dimension.

20. The method of claim 19, wherein providing a transcatheter dilatable valve tube prosthesis comprises providing the tubular member fabricated of expanded polytetrafluoroethylene (ePTFE).

21. The method of claim 19, wherein expanding the balloon catheter, comprises expanding the first dimension of about 12 mm to the second dimension of about 24 mm.

22. The method of claim 19, wherein the plurality of leaflets define a height of coaptation, wherein the height of coaptation at the first dimension and the second dimension is sufficient to maintain of the integrity of the valve component.

23. The method of claim 19, wherein providing a transcatheter dilatable valve tube prosthesis comprises providing the valve component comprising a sheet of ePTFE.

24. A method of installing a transcatheter dilatable valve tube prosthesis in the body conduit of a patient comprising:
  providing a transcatheter dilatable valve tube prosthesis comprising a tubular member capable of plastic deformation from a dimension to a second dimension; a valve component comprising a plurality of leaflets, the valve component capable of expansion from the first dimension to the second dimension, the valve component secured to an interior portion of the tubular member by an elastomeric glue at two circumferential portions defining an annular cavity therein, wherein the elastomeric glue is provided inside the annular cavity; and an expandable stent positioned in the annular cavity between the valve component and the tubular member and embedded in the elastomeric glue inside the annular cavity;
  wherein the expandable stent comprises one or more struts defining a strut width (W) and strut thickness (T) and a number of circumferential patterns (NCP), selected from a set of parameters ($\chi$) comprising strut width range, strut thickness range, number of circumferential patterns (NCP) range and stent material;
  wherein the strut width (W) and strut thickness (T) are determined by
    computing performance metrics comprising standard deviation of the descon dimension of the tubular conduit following plastic deformation (Dstddev), the peak radial force exerted by the stent to expand the tubular conduit (RF($\chi$), the Goodman metric for high cycle fatigue failure protection of the stent (GF($\chi$)) and the hydrostatic criterion for ductile failure prediction of the stent (DF($\chi$));
    constructing a surrogate model using the computed performance metrics to obtain a plurality of sets of Pareto-opitmal designs over all parameters ($\chi$); and
    identifying the strut width (W) and strut thickness (T) by optimizing a normalized aggregate objection function with equal weighing of performance metrics;
  inserting the transcatheter dilatable valve tube prosthesis into the body conduit of the patient;
  securing the transcatheter dilatable valve tube prosthesis;
  inserting a balloon catheter into the transcatheter dilatable valve tube prosthesis; and
  expanding the balloon catheter, thereby expanding the tubular member from the first dimension to the second dimension.

25. The method of claim 24, wherein the strut width range is between 0.4 mm and 0.8 mm.

26. The method of claim 24, wherein the strut thickness range is between 0.4 mm and 0.8 mm.

27. The method of claim 24, wherein the number of circumferential patterns (NCP) range is between 6 and 9 patterns.

28. The method of claim 24, wherein computing performance metrics comprises simulating the expansion of the stent by a balloon inserted in the stent.

29. The method of claim 24, wherein constructing a surrogate model using the computed performance metrics to obtain a plurality of sets of Pareto-opitmal designs over all parameters ($\chi$) comprising minimizing the performance metrics over the parameters ($\chi$).

* * * * *